(12) United States Patent
Uehira et al.

(10) Patent No.: US 6,660,465 B2
(45) Date of Patent: Dec. 9, 2003

(54) YELLOW COUPLER AND SILVER HALIDE COLOR PHOTOGRAPHIC LIGHTSENSITIVE MATERIAL CONTAINING THE SAME

(75) Inventors: Shigeki Uehira, Minami-Ashigara (JP); Kiyoshi Takeuchi, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/157,066

(22) Filed: May 30, 2002

(65) Prior Publication Data

US 2003/0104324 A1 Jun. 5, 2003

(30) Foreign Application Priority Data

Jun. 1, 2001 (JP) ........................................ 2001-167153

(51) Int. Cl.[7] .............................. G03C 1/08; G03C 7/26; G03C 7/32

(52) U.S. Cl. ........................ 430/557; 430/543; 430/544; 430/955; 430/957

(58) Field of Search ................................. 430/543, 557, 430/544, 955, 957

(56) References Cited

U.S. PATENT DOCUMENTS

| | | | |
|---|---|---|---|
| 4,326,024 A | 4/1982 | Kobayashi et al. | |
| 5,213,958 A | 5/1993 | Motoki et al. | |
| 5,427,902 A | 6/1995 | Shimura et al. | |
| 6,057,087 A | 5/2000 | Welter et al. | |

FOREIGN PATENT DOCUMENTS

| EP | 1246006 A2 * | 10/2002 | ............ G03C/7/36 |
|---|---|---|---|
| JP | 60-203943 | 10/1985 | |

* cited by examiner

*Primary Examiner*—Geraldine Letscher
(74) *Attorney, Agent, or Firm*—Sughrue Mion, PLLC

(57) ABSTRACT

A compound represented by the following formula (I) to (VII):

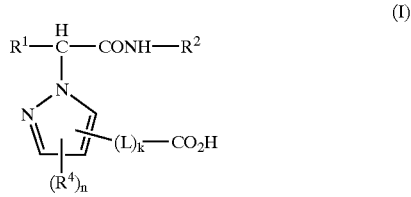

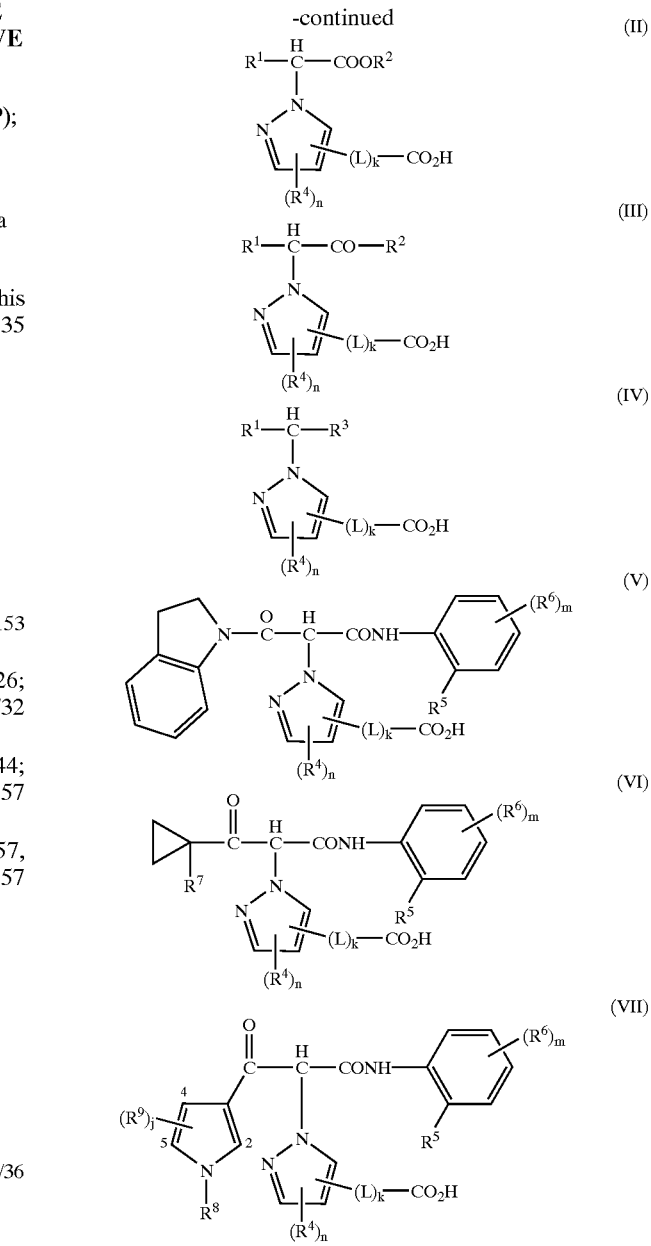

In the formulas, $R^1$ represents an acyl group, cyano group, nitro group, aryl group, heterocyclic residue, alkoxycarbonyl group, aryloxycarbonyl group, carbamoyl group, sulfamoyl group, alkylsulfonyl group, or arylsulfonyl group, which may be substituted, or a cyano or nitro group; $R^2$ represents an alkyl group, aryl group or heterocyclic residue, which may be substituted; $R^3$ represents an aryl group or heterocyclic residue, each of which may be substituted; $R^4$, $R^6$ and $R^9$ represent a substituent; $R^5$, $R^7$ and $R^8$ represent a hydrogen atom or substituent; n represents an integer of 0 to 2, wherein when n is 2, a plurality of $R^4$'s may be the same or different; L represents a divalent linking group; and k represents an integer of 0 or more, wherein when k is 2 or more, a plurality of L's may be the same or different.

4 Claims, No Drawings

YELLOW COUPLER AND SILVER HALIDE COLOR PHOTOGRAPHIC LIGHTSENSITIVE MATERIAL CONTAINING THE SAME

CROSS-REFERENCE TO RELATED APPLICATIONS

This application is based upon and claims the benefit of priority from the prior Japanese Patent Application No. 2001-167153, filed Jun. 1, 2001, the entire contents of which are incorporated herein by reference.

BACKGROUND OF THE INVENTION

1. Field of the Invention

The present invention relates to a dye-forming coupler that forms an azomethine dye by coupling reaction with an oxidant of a developing agent, and to a silver halide photographic lightsensitive material containing the coupler.

2. Description of the Related Art

In a silver halide photographic lightsensitive material (hereinafter it may be simply referred to as "lightsensitive material") in subtractive color processes, a color image is formed by dyes of three primary colors of yellow, magenta and cyan. In an existent color photography using a p-phenylenediamine color developing agent, acyl acetanilide-type compounds are used as an yellow coupler. However, a hue of the yellow dye obtained from these couplers is reddish, and if this is illustrated using an absorption curve the absorption curve of the couplers only drops gently toward the longer wavelength side after its peak, or in other words, the curve does not drop sharply toward the longer wavelength side after its peak. Thus, it is difficult to obtain a yellow hue of high purity. Further, it has the problem that the molar extinction coefficient of the dye is small, and thus a large quantity of couplers and silver halide are required to obtain a desired color density, which increases the film thickness of the lightsensitive material and reduces sharpness of a color image obtained. Furthermore, the dye is ready to decompose under conditions of high temperature and high humidity, or under conditions of light irradiation, and has a problem in the image storability after development, and thus is required to be improved.

To solve these problems, the acy and anilide groups have been improved, and recently, 1-alkylcyclopropanecarbonylacetanilide compounds described in Jpn. Pat. Appln. KOKAI Publication No. (hereinafter referred to as "JP-A-") 4-218042, a malonediamide-type coupler described in JP-A-5-11416, and pyrrole-2-yl or -3-yl or indole-2-ylcarbonyl or -3-yl carbonylacetanilide couplers described in EP's 953870A1, 953871A1, 953872A1, 953873A1, 953874A1, and 953875A1, for example, have been proposed as a coupler obtained by improving a conventional acyl acetanilides. Dyes generated from these couplers have been improved in the hue and molar extinction coefficient in comparison with a conventional one. However, the color generation property of the couplers are low, and thus the structures of the couplers are very complicated to improve the low color generation property. Therefore, synthesizing the couplers is difficult, and the route becomes long, which increases the costs of the couplers, and causes a problem in practical use.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF SUMMARY OF THE INVENTION

Therefore, the object of the present invention is to provide a dye-forming coupler with high color generation property, which can be prepared with a shorter process and at a low cost, and provide a silver halide color photographic lightsensitive material containing such a coupler.

As a result of diligent researches, the inventors of the present invention have found couplers represented by the following formulae (I)–(VII) solves the above problems. Specifically, the present invention provides yellow couplers represented by the following formulae (I)–(IV):

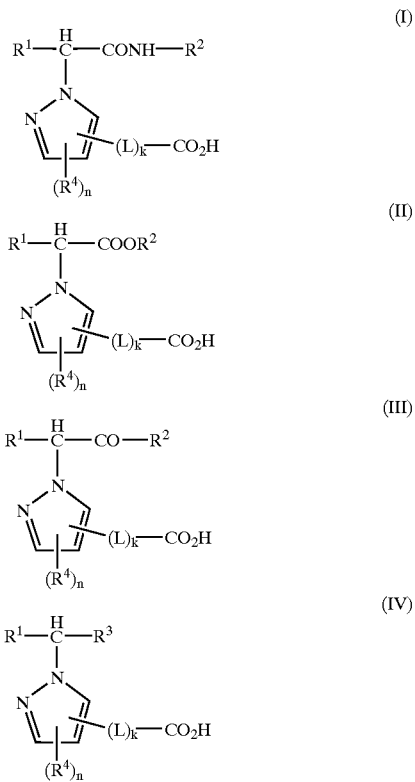

In the formulae, $R^1$ represents an acyl group, cyano group, nitro group, aryl group, heterocyclic residue, alkoxycarbonyl group, aryloxycarbonyl group, carbamoyl group, sulfamoyl group, alkylsulfonyl group, or arylsulfonyl group, each of which may have a substituent. $R^2$ represents an alkyl group, aryl group or heterocyclic residue, each of which may have a substituent. $R^3$ represents an aryl group or heterocyclic residue, each of which may have a substituent. $R^4$ represents a substituent. n represents an integer of 0 to 2. If n is 2, a plurality of $R^4$'s may be the same or different from each other. L represents a divalent linking group. k represents an integer of 0 or more, and if k is 2 or more, a plurality of L's may be the same linking groups or may be different from each other.

(2) Further, the present invention provides a dye-forming coupler represented by the following formula (V):

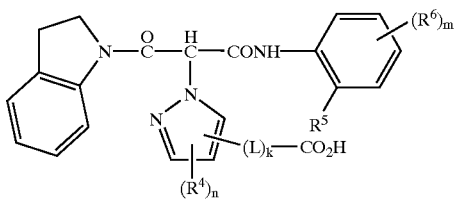

(V)

In the formula, $R^4$ represents a substituent. n represents an integer of 0 to 2. If n is 2, a plurality of $R^4$'s may be the same or different from each other. $R^5$ represents a hydrogen atom or substituent. $R^6$ represents a substituent. m represents an integer of 0 to 4, and if m is 2 or more, a plurality of $R^6$'s may be the same or different from each other, and two of them may be bonded together to form a ring. L represents a divalent linking group. k represents an integer of 0 or more, and if k is 2 or more, a plurality of L's may be the same or different from each other.

(3) Still further, the present invention provides a yellow coupler represented by formula (VI):

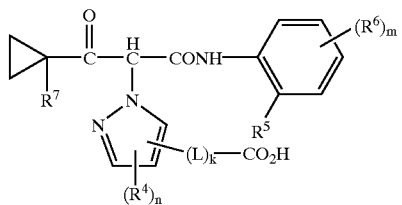

(VI)

In the formula, $R^4$ represents a substituent. n represents an integer of 0 to 2. If n is 2 or more, a plurality of $R^4$'s may be the same or different from each other. $R^6$ represents a substituent. $R^5$ and $R^7$ independently represents a hydrogen atom or substituent. m represents an integer of 0 to 4. If m is 2 or more, a plurality of $R^6$'s may be the same or different from each other, and two of them may be bonded together to form a ring. L represents a divalent linking group. k represents an integer of 0 or more. If k is 2 or more, a plurality of L's may be the same or different from each other.

(4) Still further, the present invention provides a yellow coupler represented by formula (VII):

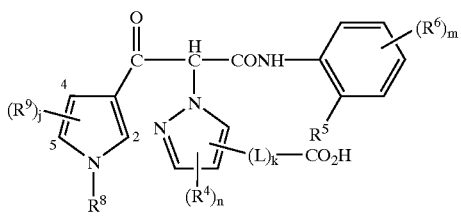

(VII)

In the formula, $R^4$ represents a substituent. n represents an integer of 0 to 2. If n is 2 or more, a plurality of $R^4$'s may be the same or different from each other. $R^6$ and $R^9$ independently represents a substituent. $R^5$ and $R^8$ independently represents a hydrogen atom or substituent. m represents an integer of 0 to 4. If m is 2 or more, a plurality of $R^6$'s may be the same or different from each other, and two of them may be bonded together to form a ring. L represents a divalent linking group. k represents an integer of 0 or more. If k is 2 or more, a plurality of L's may be the same or different from each other. j represents an integer of 3 or less. If j is 2 or more, a plurality of $R^9$'s may be the same or different from each other, and two of them may be bonded together to form a ring.

(5) Further, the present invention provides a silver halide color photographic lightsensitive material containing at least one of the yellow couplers represented by the formulae (I) to (VII) described in the above items (1) to (4).

DETAILED DESCRIPTION OF THE INVENTION

The compounds (also referred to as "dye-forming couplers" in the present specification) represented by the formulae (I)–(IV) of the present invention will be described in detail.

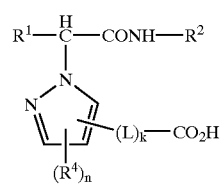

(I)

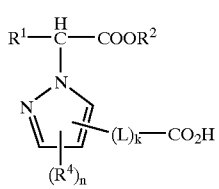

(II)

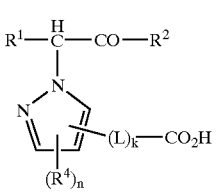

(III)

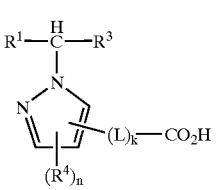

(IV)

In the formulae, $R^1$ is an acyl group, aryl group, heterocyclic residue, alkoxycarbonyl group, aryloxycarbonyl group, carbamoyl group, sulfamoyl group, alkylsulfonyl group, or arylsulfonyl group, each of which may have a substituent, or a cyano group or nitro group. Examples of the substituent which $R^1$ may have are halogen atom, alkyl group (including cycloalkyl group, and bicycloalkyl group), alkenyl group (including cycloalkenyl group, and bicycloalkenyl group), alkynyl group, aryl group, heterocyclic group, cyano group, hydroxyl group, nitro group, carboxyl group, alkoxy group, aryloxy group, silyloxy group, heterocyclic oxy group, acyloxy group, carbamoyloxy group, alkoxycarbonyloxy group, aryloxycarbonyloxy group, amino group (including alkylamino group and anilino group), acylamino group, aminocarbonylamino group, alkoxycarbonylamino group, aryloxycarbonylamino group, sulfamoylamino group, alkyl and arylsulfonylamino groups, mercapto group, alkylthio group, arylthio group, heterocyclic thio group, sulfamoyl group, sulfo group, alkyl and arylsulfinyl groups, alkyl and aryl sulfonyl groups, acyl group, aryloxycarbonyl group, alkoxycarbonyl group, carbamoyl group, aryl and heterocyclic azo groups, imide group, phosphino group, phosphinyl group, phosphinyloxy group, phosphinylamino group, and silyl group.

The above substituents may be further substituted by substituents being the above substituents. Further, two of such substituents on $R^1$ may be bonded together to form a ring.

Examples of $R^1$ will now be further described.

Examples of $R^1$ are an acyl group (preferably a formyl group, a substituted or unsubstituted alkylcarbonyl group having 2 to 30 carbon atoms, and a substituted or unsubstituted arylcarbonyl group having 7 to 30 carbon atoms, such as acetyl, pivaloyl, 2-chloroacetyl, stearoyl, benzoyl, and p-n-octyloxyphenylcarbonyl), aryl group (preferably a substituted or unsubstituted aryl group having 6 to 30 carbon atoms, such as phenyl, p-tolyl, naphthyl, m-chlorophenyl, and o-hexadecanoylaminophenyl), heterocyclic group (preferably a 5- to 7-membered substituted or unsubstituted, saturated or unsaturated, aromatic or non-aromatic, and monocyclic or condensed heterocyclic group, more preferably a heterocyclic group whose ring forming atoms are selected from a carbon atom, nitrogen atom and sulfur atom, and which has at least one hetero atom of any one of nitrogen atom, oxygen atom and sulfur atom, and further preferably 5- or 6-membered aromatic heterocyclic group having 3 to 30 carbon atoms, such as 2-furyl, 2-thienyl, 2-pyridyl, 4-pyridil, 2-pyrimidinyl, 2-benzothiazolyl, quinazolinon-2-yl, and 1,2,4-benzothiadiazine-1,1-dioxide-3-yl), alkoxycarbonyl group (preferably a substituted or unsubstituted alkoxycarbonyl group having 2 to 30 carbon atoms, such as methoxycarbonyl, ethoxycarbonyl, t-butoxycarbonyl, and n-octadecyloxycarbonyl), aryloxycarbonyl group (preferably a substituted or unsubstituted aryloxycarbonyl group having 7 to 30 carbon atoms, such as phenoxycarbonyl, o-chlorophenoxycarbonyl, m-nitrophenoxycarbonyl, and p-t-butylphenoxycarbonyl), carbamoyl group (preferably a substituted or unsubstituted carbamoyl having 1 to 30 carbon atoms, such as carbamoyl, N-methylcarbamoyl, N,N-dimethylcarbamoyl, N,N-di-n-octylcarbamoyl, N-(methylsulfonyl)carbamoyl), sulfamoyl group (preferably a substituted or unsubstituted sulfamoyl group having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N-(N'-phenylcarbamoyl)sulfamoyl), alkyl and arylsulfonyl group (preferably a substituted or unsubstituted alkylsulfonyl group having 1 to 30 carbon atoms, and a substituted or unsubstituted arylsulfonyl group having 6 to 30 carbon atoms, such as methylsulfonyl, ethylsulfonyl, phenylsulfonyl, p-methylphenylsulfonyl), cyano group and nitro group.

Examples of substituents which $R^1$ may have will now be further described.

Examples of the substituents are halogen atom (e.g., chlorine atom, bromine atom, and iodine atom), alkyl group (e.g., straight-chain or branched, and substituted or unsubstituted alkyl group, preferably an alkyl group having 1 to 30 carbon atoms, such as methyl, ethyl, n-propyl, isopropyl, t-butyl, n-octyl, eicosyl, 2-chloroethyl, 2-cyanoethyl, 2-ethylhexyl, 3-(2,4-di-t-amylphenoxy)propyl), cycloalkyl group (preferably a substituted or unsubstituted cycloalkyl group having 3 to 30 carbon atoms, such as cyclohexyl, cyclopentyl, and 4-n-dodecylcyclohexyl, polycycloalkyl group which is a group of a polycyclic structure such as bicycloalkyl group (preferably a substituted or unsubstituted bicycloalkyl group having 5 to 30 carbon atoms, such as bicyclo[1,2,2]heptane-2-yl, and bicyclo[2,2,2]octane-3-yl) and tricycloalkyl. Preferably monocyclic alkyl group and bicycloakyl group, and especially preferably a monocyclic alkyl group.), alkenyl group (straight-chain or branched, and substituted or unsubstituted alkenyl group, preferably an alkenyl group having 2 to 30 carbon atoms, such as vinyl, allyl, prenyl, geranyl and oleyl), cycloalkenyl group (preferably a substituted or unsubstituted cycloalkenyl group having 3 to 30 carbon atoms, such as 2-cyclopentene-1-yl, 2-cyclohexene-1-yl), polycycloalkenyl group such as bicycloalkenyl group (preferably a substituted or unsubstituted bicycloalkenyl group having 5 to 30 carbon atoms, such as bicyclo[2,2,1]hept-2-ene-1-yl, and bicyclo[2,2,2]oct-2-ene-4-yl), and tricycloalkenyl group, and monocyclic alkenyl group is especially preferable.), alkinyl group (preferably a substituted or unsubstituted alkinyl group having 2 to 30 carbon atoms, such as ethinyl, propargyl, and trimethylsilylethinyl group), aryl group (preferably a substituted or unsubstituted aryl group having 6 to 30 carbon atoms, such as phenyl, p-tolyl, naphthyl, m-chlorophenyl, o-hexadecanoylaminophenyl), heterocyclic group (preferably a 5- to 7-membered substituted or unsubstituted, saturated or unsaturated, aromatic or nonaromatic, monocyclic or condensed heterocyclic group, more preferably a heterocyclic group whose ring-forming atoms are selected from carbon atom, nitrogen atom or sulfur atom, and which has at least one hetero atom of any of nitrogen atom, oxygen atom and sulfur atom, further preferably a 5- or 6-membered aromatic heterocyclic group having 3 to 30 carbon atoms, such as 2-furyl, 2-thienyl, 2-pyridyl, 4-pyridyl, 2-pyrimidinyl, and 2-benzothiazolyl), cyano group, hydroxyl group, nitro group, carboxyl group, alkoxy group (preferably a substituted or unsubstituted alkoxy group having 1 to 30 carbon atoms, such as methoxy, ethoxy, isopropoxy, t-butoxy, n-octyloxy, and 2-methoxyethoxy), aryloxy group (preferably a substituted or unsubstituted aryloxy group having 6 to 30 carbon atoms, such as phonoxy, 2-methylphenoxy, 2,4-di-t-amylphenoxy, 4-t-butylphenoxy, 3-nitrophenoxy, and 2-tetradecanoylaminophenoxy), silyloxy group (preferably a silyloxy group having 3 to 20 carbon atoms, such as trimethylsilyloxy and t-butyldimethylsilyloxy), heterocyclic oxy group (preferably a substituted or unsubstituted heterocyclic oxy group having 2 to 30 carbon atoms, in which a heterocyclic portion is preferably the heterocyclic portion explained with respect to the heterocyclic group, such as 1-phenyltetrazole-5-oxy and 2-tetrahydropyranyloxy), acyloxy group (preferably a formyloxy group, substituted or unsubstituted alkylcarbonyloxy group having 2 to 30 carbon atoms, and substituted or unsubstituted arylcarbonyloxy group having 7 to 30 carbon atoms, such as acetyloxy, pivaloyloxy, stearoyloxy, benzoyloxy, and p-methoxyphenylcarbonyloxy), carbamoyloxy group (preferably a substituted or unsubstituted carbamoyloxy group having 1 to 30 carbon atoms, such as N,N-dimethylcarbamoyloxy, N,N-diethylcarbamoyloxy, morpholinocarbonyloxy, N,N-di-n-octylaminocarbonyloxy, and N-n-octylcarbamoyloxy), alkoxycarbonyloxy group (preferably a substituted or unsubstituted alkoxycarbonyloxy group having 2 to 30 carbon atoms, such as methoxycarbonyloxy, ethoxycarbonyloxy, t-butoxycarbonyloxy, and n-octylcarbonyloxy), aryloxycarbonyloxy (preferably a substituted or unsubstituted aryloxycarbonyloxy group having 7 to 30 carbon atoms, such as phenoxycarbonyloxy, p-methoxyphenoxycarbonyloxy, and p-n-hexadecyloxyphenoxycarbonyloxy), amino group (preferably an amino group, a substituted or unsubstituted alkylamino group having 1 to 30 carbon atoms, substituted or unsubstituted arylamino group having 6 to 30 carbon atoms, and heterocyclic amino group having 0 to 30 carbon atoms, such as amino, methylamino, dimethylamino, anilino, N-methylanilino, diphenylamino, and N-1,3,5-triazine-2-ylamino), acylamino group (preferably formylamino group, substituted or unsubstituted alkylcarbonylamino group having 2 to 30 carbon atoms, and substituted or unsubstituted arylcarbonylamino group having 7 to 30 carbon atoms, such as acetylamino, pivaloylamino, lauroylamino, benzoylamino, and 3,4,5-tri-n-octyloxyphenylcarbonylamino), aminocarbonylamino group (preferably a substituted or unsubstituted aminocarbonylamino group having 1 to 30 carbon atoms, such as carbamoylamino, N,N-dimethylaminocarbonylamino, N,N-diethylaminocarbonylamino, and morpholinocarbonylamino), alkoxycarbonylamino (preferably a substituted or unsubstituted alkoxycarbonylamino group having 2 to 30 carbon atoms, such as methoxycarbonylamino, ethoxycarbonylamino, t-butoxycarbonylamino, n-octadecyloxycarbonylamino, and N-methyl-methoxycarbonylamino), aryloxycarbonylamino group (preferably a substituted or unsubstituted aryloxycarbonylamino group having 7 to 30 carbon atoms, such as phenoxycarbonylamino, p-chlorophenoxycarbonylamino, and m-n-octyloxyphenoxycarbonylamino), sulfamoylamino group (preferably a substituted or unsubstituted sulfamoylamino group having 0 to 30 carbon atoms, such as sulfamoylamino, N,N-dimethylaminosulfonylamino, and N-n-octylaminosulfonylamino), alkyl and arylsulfonylamino groups (preferably a substituted or unsubstituted alkylsulfonylamino group having 1 to 30 carbon atoms, and substituted or unsubstituted arylsulfonylamino group having 6 to 30 carbon atoms, such as methylsulfonylamino, butylsulfonylamino, phenylsulfonylamino, 2,3,5-trichlorophenylsulfonylamino, and p-methylphenylsulfonylamino), mercapto group, alkylthio group (preferably a substituted or unsubstituted alkylthio group having 1 to 30 carbon atoms, such as methylthio, ethylthio, n-hexadecylthio), arylthio group (preferably a substituted or unsubstituted arylthio group having 6 to 30 carbon atoms, such as phenylthio, p-chlorophenylthio, and m-methoxyphenylthio), heterocyclic thio group (preferably a substituted or unsubstituted heterocyclic thio group having 2 to 30 carbon atoms, in which a heterocyclic portion is preferably the heterocyclic portion explained with respect to the heterocyclic group, such as 2-benzothiazolylthio, and 1-phenyltetrazole-5-ylthio), sulfamoyl group (preferably a substituted or unsubstituted sulfamoyl group having 0 to 30 carbon group, such as N-ethylsulfamoyl, N-(3-dodecyloxypropyl)sulfamoyl, N,N-dimethylsulfamoyl, N-acetylsulfamoyl, N-benzoylsulfamoyl and N-(N'-phenylcarbamoyl) sulfamoyl), sulfo group, alkyl and arylsulfinyl groups (preferably a substituted or unsubstituted alkylsulfinyl group having 1 to 30 carbon atoms, and arylsulfinyl group having 6 to 30 carbon atoms, such as methylsulfinyl, ethylsulfinyl, phenylsulfinyl, and p-methylphenylsulfinyl), alkyl and arylsulfonyl groups (preferably a substituted or unsubstituted alkylsulfonyl group having 1 to 30 carbon atoms, and a substituted or unsubstituted arylsulfonyl group having 6 to 30 carbon atoms, such as methylsulfonyl, ethylsulfonyl, phenylsulfonyl, and p-methylphenylsulfonyl), acyl group (preferably a formyl group, substituted or unsubstituted alkylcarbonyl group having 2 to 30 carbon atoms, and substituted or unsubstituted arylcarbonyl group having 7 to 30 carbon atoms, such as acetyl, pivaloyl, 2-chloroacetyl, stearoyl, benzoyl, and p-n-octyloxyphenylcarbonyl), aryloxycarbonyl group (preferably a substituted or unsubstituted aryloxycarbonyl group having 7 to 30 carbon atoms, such as phenoxycarbonyl, o-chlorophenoxycarbonyl, m-nitrophenoxycarbonyl, and p-t-butylphenoxycarbonyl), alkoxycarbonyl group (preferably a substituted or unsubstituted alkoxycarbonyl group having 2 to 30 carbon atoms, such as methoxycarbonyl, ethoxycarbonyl, t-butoxycarbonyl, and n-octadecyloxycarbonyl), carbamoyl group (preferably a substituted or unsubstituted carbamoyl having 1 to 30 carbon atoms, such as carbamoyl, N-methylcarbamoyl, N,N-dimethylcarbamoyl, N,N-di-n-octylcarbamoyl, and N-(methylsulfonyl)carbamoyl), aryl and heterocyclic azo groups (preferably a substituted or unsubstituted aryl azo group having 6 to 30 carbon atoms, and a substituted or unsubstituted heterocyclic azo group having 3 to 30 carbon atoms (in which a heterocyclic portion is preferably the heterocyclic portion explained with respect to the heterocyclic group), such as phenylazo, p-chlorophenylazo, and 5-ethylthio-1,3,4-thiadiazole-2-ylazo), imide group (preferably a substituted or unsubstituted imide group having 2 to 30 carbon atoms, such as N-succinimide, and N-phthalimide), phosphino group (preferably a substituted or unsubstituted phosphino group, such as dimethylphosphino, diphenylphosphino, and methylphenoxyphosphino), phosphinyl group (preferably a substituted or unsubstituted phosphinyl group having 0 to 30 carbon atoms, such as phosphinyl, dioctyloxyphosphinyl, and diethoxyphosphinyl), phosphinyloxy group (preferably a substituted or unsubstituted phosphinyloxy group having 2 to 30 carbon atoms, such as diphenoxyphosphinyloxy, and dioctyl oxyphosphinyloxy), phosphinylamino group (preferably a substituted or unsubstituted phosphinuylamino group having 2 to 30 carbon atoms, such as dimethoxyphosphinylamino, and dimethylaminophosphinylamino), silyl group (preferably a substituted or unsubstituted silyl group having 0 to 30 carbon atoms, such as trimethylsilyl, t-butyldimethylsilyl, and phenyldimethylsilyl).

With respect to functional groups having a hydrogen atom among the above functional groups, the hydrogen atom may be removed and substituted by the above groups. Examples of such functional groups are alkylcarbonylaminosulfonyl group, arylcarbonylaminosulfonyl group, alkylsulfonylaminocarbonyl group, and arylsulfonylaminocarbonyl group, specifically, methylsulfonylaminocarbonyl, p-methylphenylsulfonylaminocarbonyl, acetylaminosulfonyl, and benzoylaminosulfonyl group.

$R^1$ is preferably an acyl group, carbamoyl group, aryl group or heterocyclic residue, each of which may have a substituent, more preferably an acyl group carbamoyl group or heterocyclic residue, each of which may have a substituent, and much more preferably an acyl group or carbamoyl group, each of which may have a substituent, and especially preferably, a substituted carbamoyl group.

In the formulae (I) to (IV), $R^2$ is an alkyl group, aryl group or heterocyclic residue, each of which may have a substituent. Examples of substituents which these groups may have are the examples of substituents which $R^1$ may have.

$R^3$ is an aryl group or heterocyclic residue, each of which may have a substituent, preferably a heterocyclic residue. Further, examples of substituents which these groups may have are the examples of substituents which $R^1$ may have.

$R^4$ is a substituent, and examples thereof are the examples of the substituents which $R^1$ may have. Further, if n is 2, a plurality of $R^4$'s may represent the same substituent as each other, or may represent substituents different from each other.

To immobilize a coupler in the photosensitive material, the total number of carbon atoms, including substituents, of at least one of $R^1$, $R^2$, $R^3$ and $R^4$ is preferably 8 to 50, and more preferably 10 to 40.

L represents a divalent linking group. Examples of L are an alkylene group such as methylene group and ethylene group, arylene group such as phenylene group, heterocyclic group, oxygen atom, nitrogen atom, sulfur atom, carbonyl group, sulfonyl group, phosphorus atom, phosphonyl group, and boron atom. Preferably L is an alkylene group, more preferably a methylene group or ethylene group, and most preferably a methylene group.

Further, k is an integer of 0 or more, and if k is 2 or more, each L may represent the same linking group or may be different from each other. Preferably k is 0 to 5, more preferably 0 to 2, further preferably 0 or 1, and most preferably 0.

In the present invention, the couplers represented by the formula (I) are preferable, among the couplers represented by formulae (I) to (IV). Further preferably, in the formula (I), $R^1$ is an alkylcarbonyl group, arylcarbonyl group, heterocyclic carbonyl group, carbamoyl group, alkoxycarbonyl group, or heterocyclic residue, and more preferably $R^1$ is an alkylcarbonyl group, heterocyclic carbonyl group or carbamoyl group. Still more preferable couplers are those represented by formulae (V) to (VII) to be described below, and especially preferable couplers are those represented by the formula (V).

Next, compounds (also referred to as "dye-forming couplers" in the present specification) represented by the formula (V) of the present invention will now be described in detail.

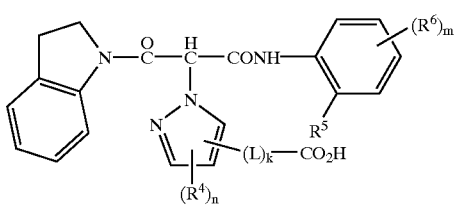
(V)

In the formula (V), each of $R^4$, L, k and n represents the same one stated with respect to the formulae (I) to (IV), and their preferable ranges are the same as those in the formulae (I) to (IV).

$R^5$ represents a hydrogen atom or substituent. Examples of the substituent are the substituents mentioned as examples of the substituents that $R^1$ may have. Preferably $R^5$ is a halogen atom, alkyl group, alkoxy group, aryloxy group, alkoxycarbonyl group, aryloxycarbonyl group, carbamoyl group, sulfamoyl group, acylamino group, or alkyl and arylsulfonylamino group, more preferably a halogen atom, alkyl group, alkoxy group, or aryloxy group, further preferably a halogen atom or alkoxy group, and most preferably an alkoxy group.

$R^6$ represents a substituent. Examples of the substituent are the substituents mentioned as examples of the substituent that $R^1$ may have. Preferably $R^6$ is a halogen atom, alkyl group, alkoxy group, aryloxy group, alkoxycarbonyl group, aryloxycarbonyl group, carbamoyl group, sulfamoyl group, acylamino group, or alkyl and arylsulfonylamino group. m represents an integer of 0 to 4, and if m is 2 or more, a plurality of $R^6$'s may represent the same substituent or different substituents, and two of them may bind together to form a ring.

Next, the compound (also refereed to as a dye-forming coupler in the present specification) represented by formula (VI) of the invention will be described.

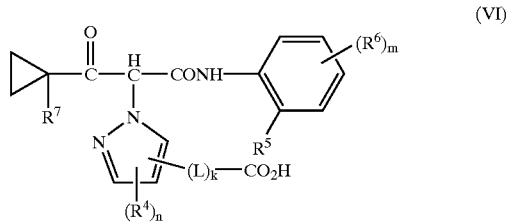
(VI)

In the formula (VI), $R^4$, $R^5$, $R^6$, L, k and n have the same meanings as those mentioned for the formula (V), respectively, and preferable scopes thereof are also the same.

$R^7$ represents a hydrogen atom or substituent. Examples of the substituent are the substituents mentioned as examples of the substituent that $R^1$ may have. Preferably, $R^7$ is a hydrogen atom, alkyl group, alkoxy group, or aryloxy group. More preferably, $R^7$ is an alkyl group.

Next, the compound (also refereed to as a dye-forming coupler in the present specification) represented by formula (VII) of the invention will be described.

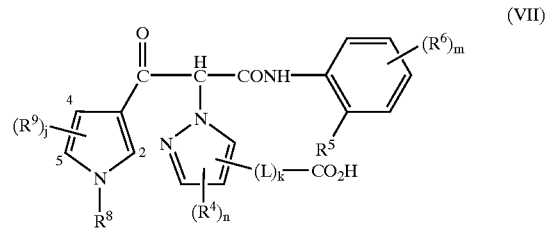
(VII)

In the formula (VII), $R^4$, $R^5$, $R^6$, L, k and n have the same meanings as those mentioned for the formula (V), respectively, and preferable scopes thereof are also the same.

$R^8$ represents a hydrogen atom or substituent. Examples of the substituent are the substituents mentioned as examples of the substituent that $R^1$ may have. Preferably, $R^8$ is an alkyl group or aryl group. More preferably, $R^8$ is an alkyl group.

$R^9$ represents a substituent. Examples of the substituent are the substituents mentioned as examples of the substituent that $R^1$ may have. Preferably, $R^9$ is an alkyl group, acyl group, halogen atom, carbonyl group, alkoxy group, carbonamide group, carbamoyl group, heterocyclic group, or aryl group. More preferably, $R^9$ is an aryl group.

When $R^9$ is present as a substituent at 2- or 5-position of the azole ring, $R^9$ may form a ring together with $R^8$.

j represents an integer of 0 or more and 3 or less. If j is 2 or more, a plurality of $R^9$'s may be the same or different from each other, and two of them may be bonded together to form a ring.

Preferred examples of couplers represented by the formulae (I) to (VII) of the present invention will be described below. However, the present invention is not limited to them.

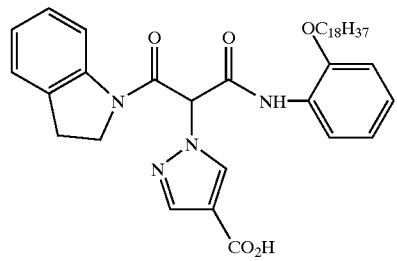
(1)

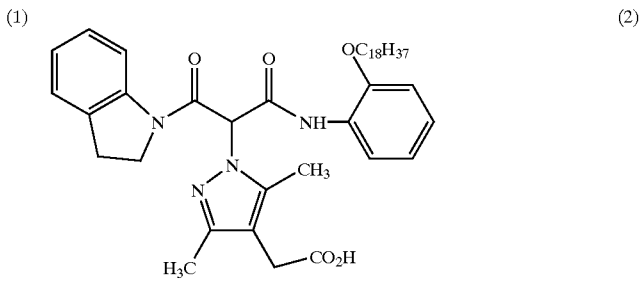
(2)

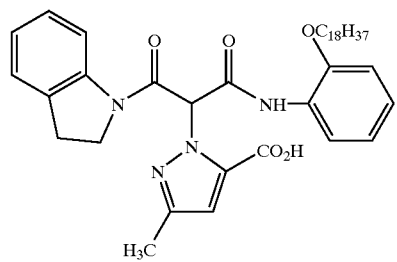
(3)

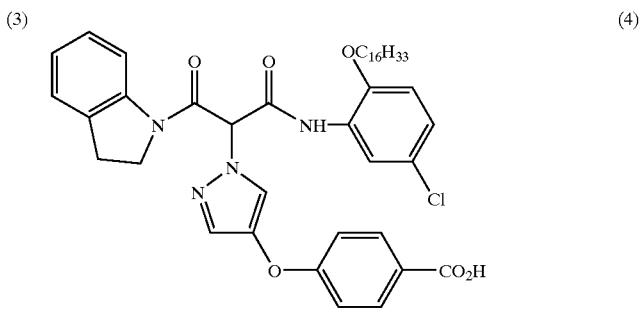
(4)

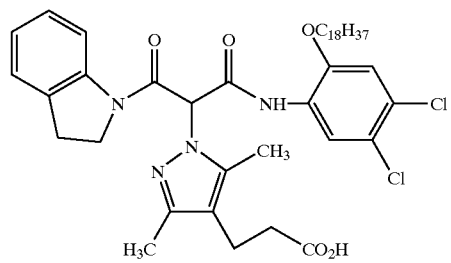
(5)

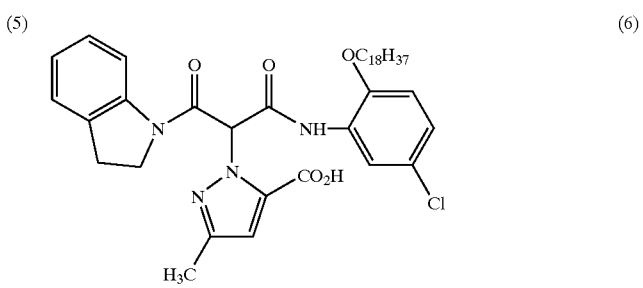
(6)

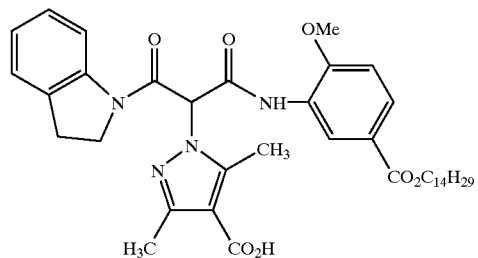

(7)

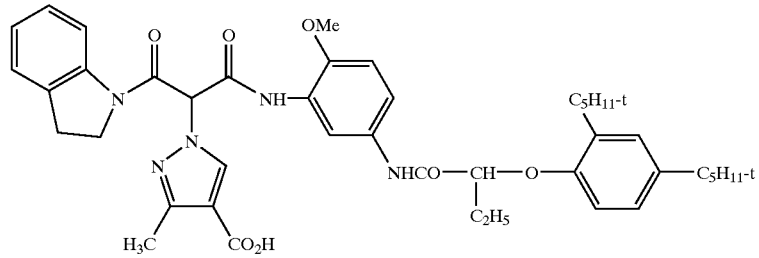

(8)

-continued
(9)
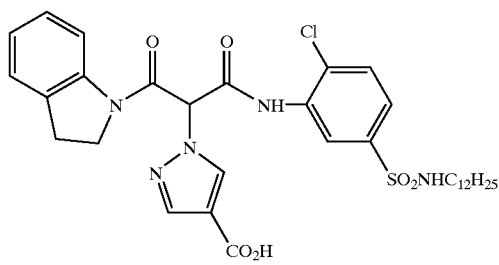
(10)
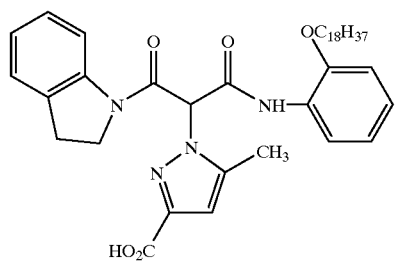
(11)
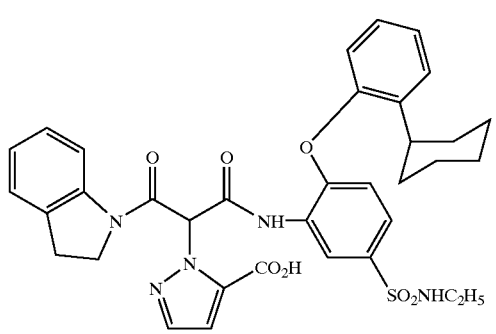
(12)
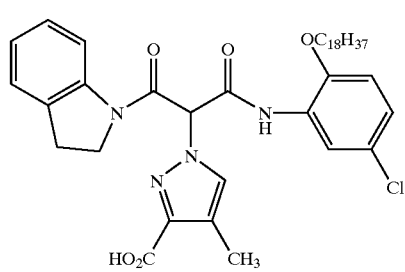
(13)
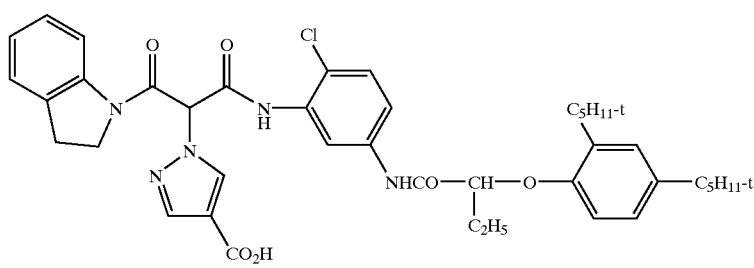
(14)
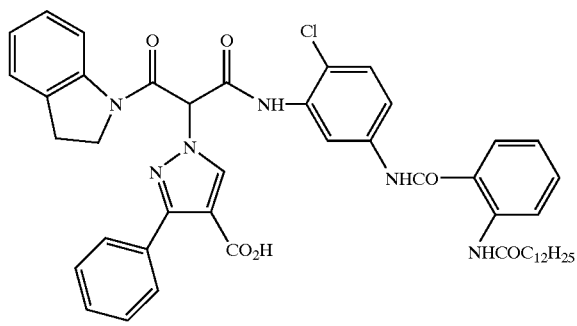
(15)
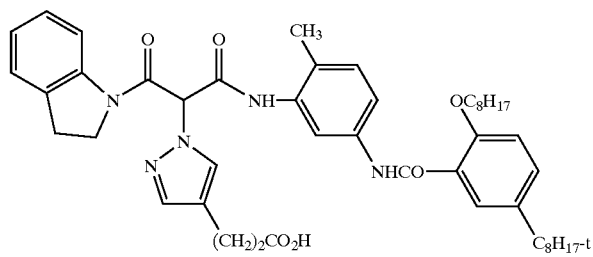
(16)
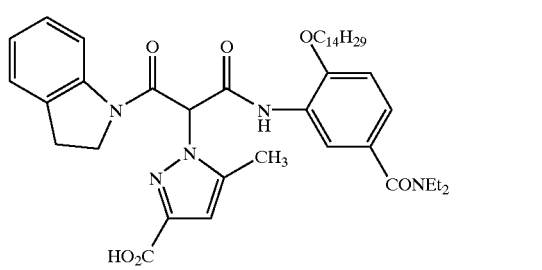
(17)
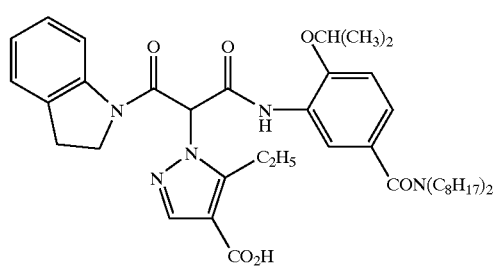

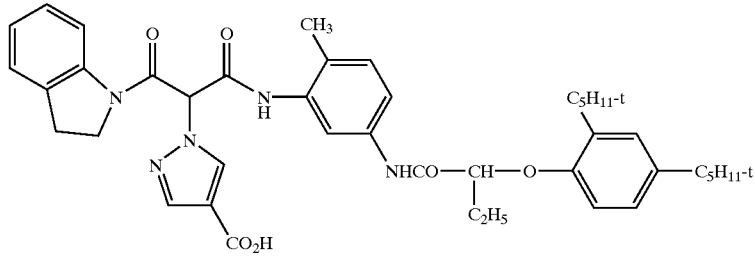
(18)
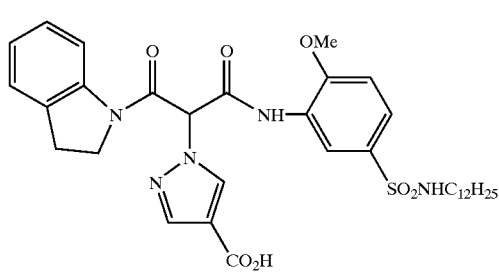
(19)
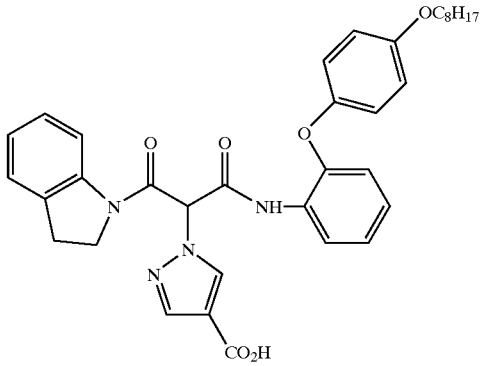
(20)
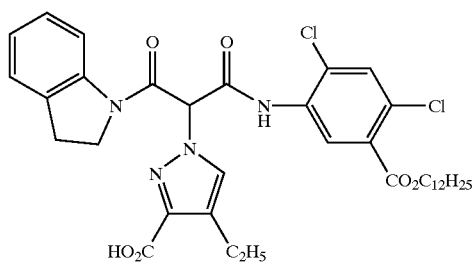
(21)
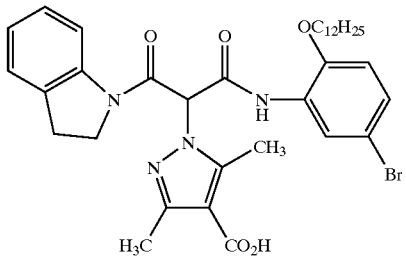
(22)
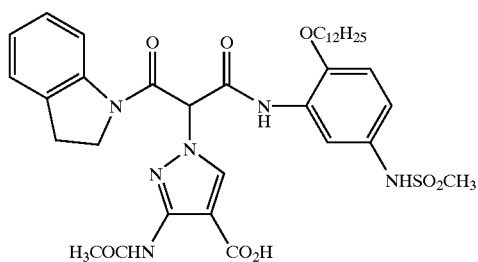
(23)
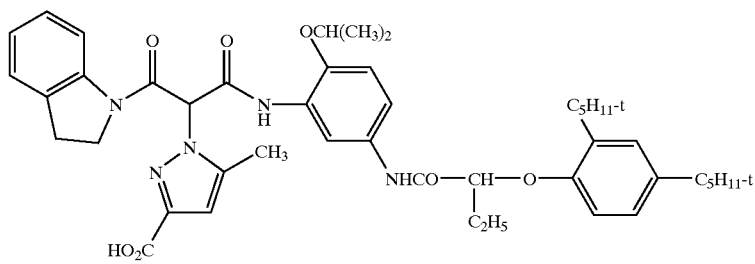
(24)

(25)
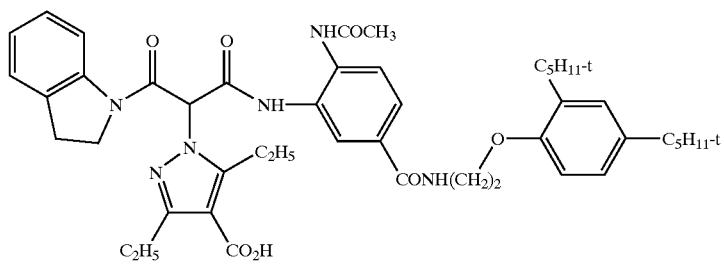
(26)
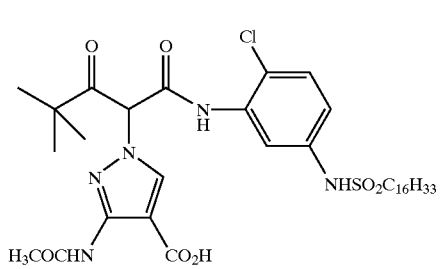
(27)
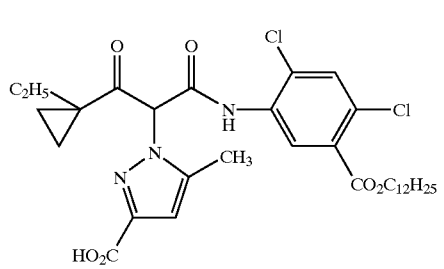
(28)
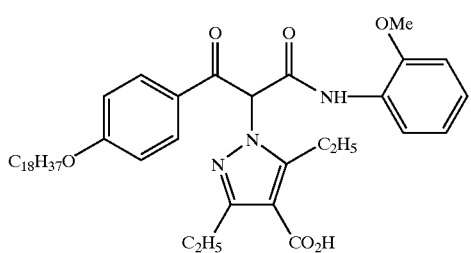
(29)
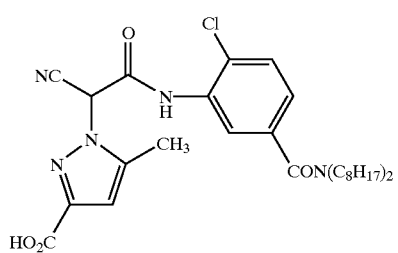
(30)
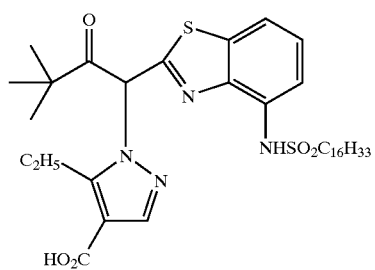
(31)
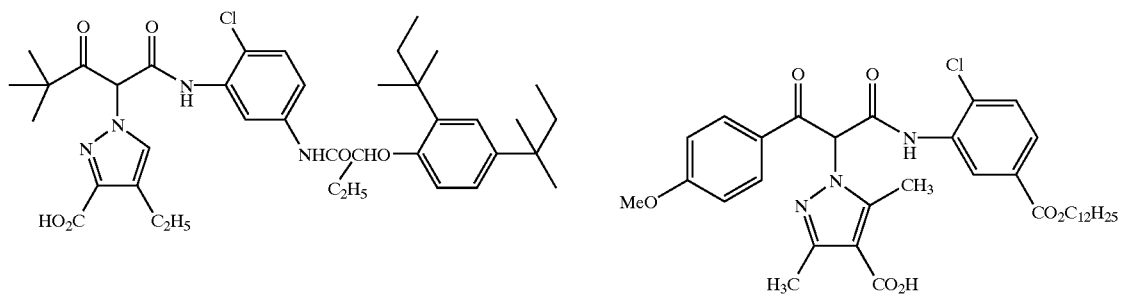
(32)
(33)
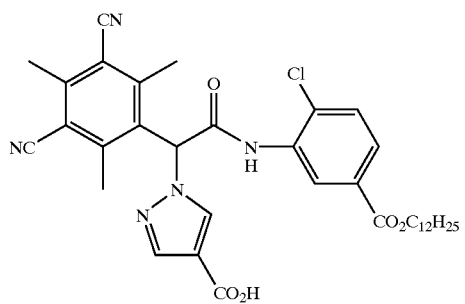

(34)
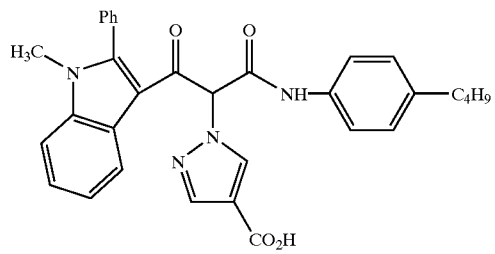
(35)
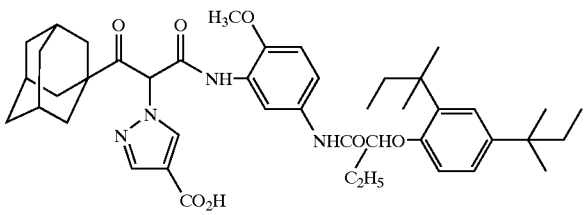
(36)
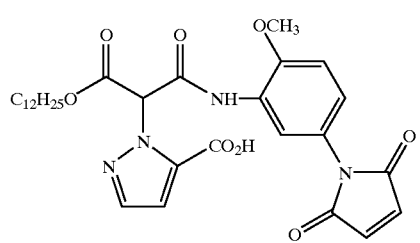
(37)
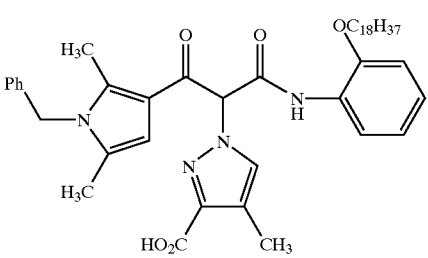
(38)
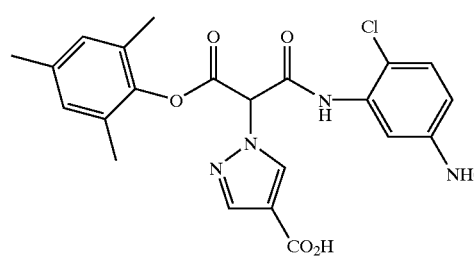
(39)
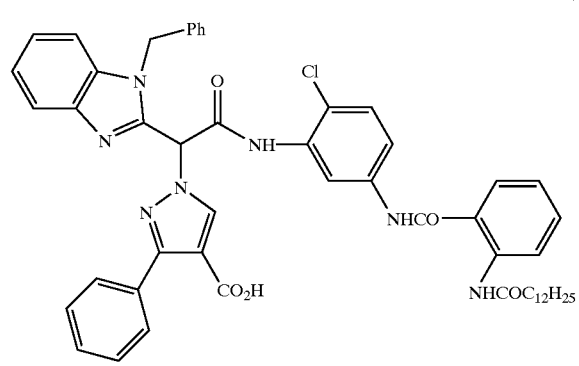
(40)
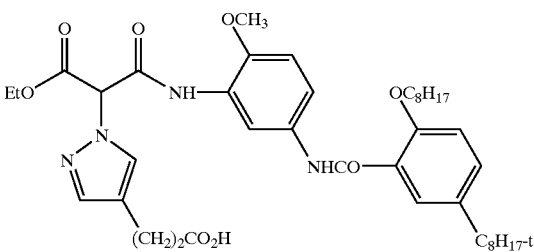
(41)
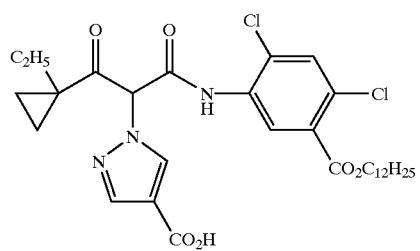
(42)
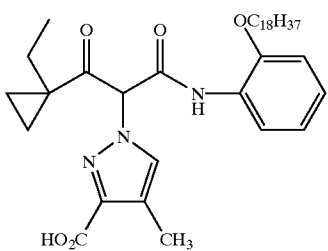

-continued
(43)
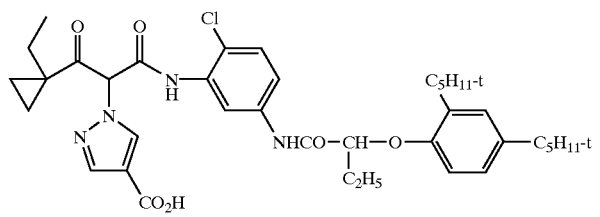
(44)
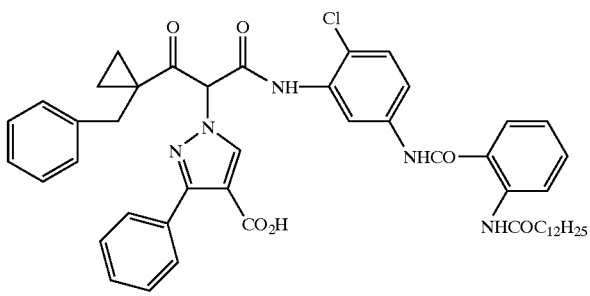
(45)
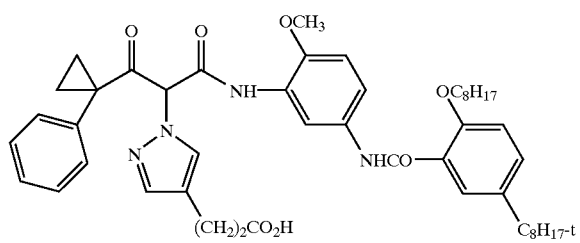
(46)
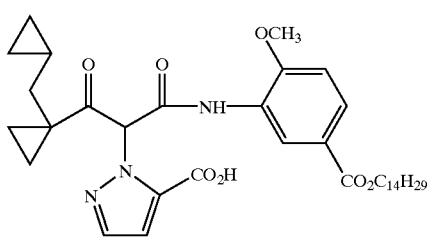
(47)
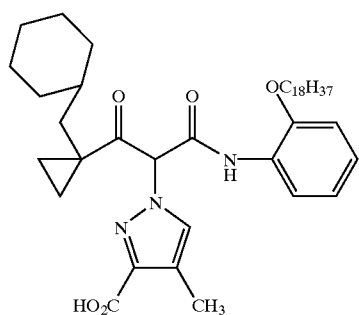
(48)
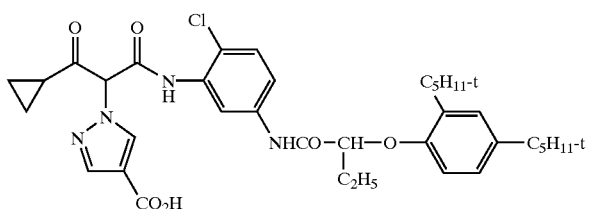
(49)
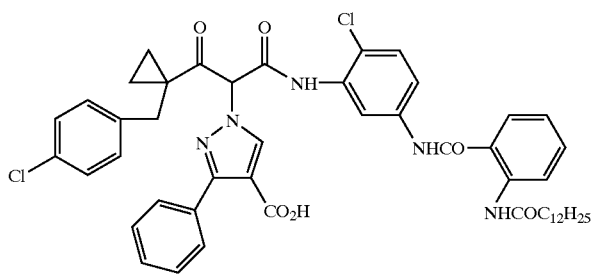
(50)
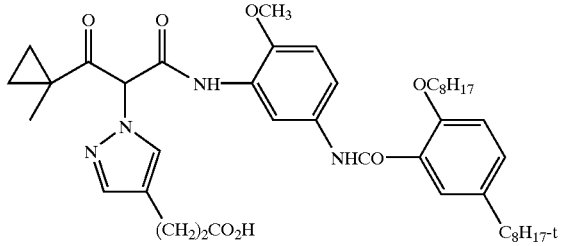
(51)
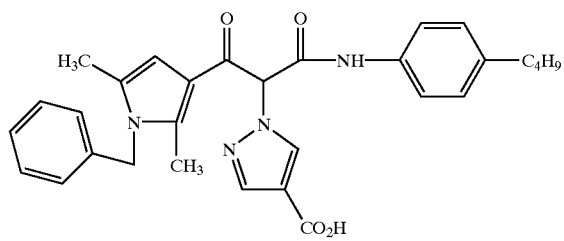
(52)
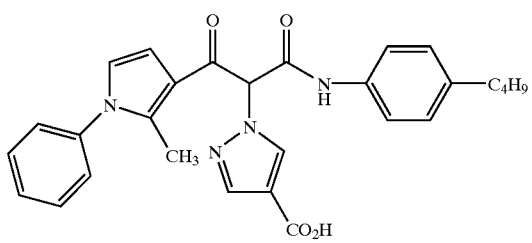

-continued
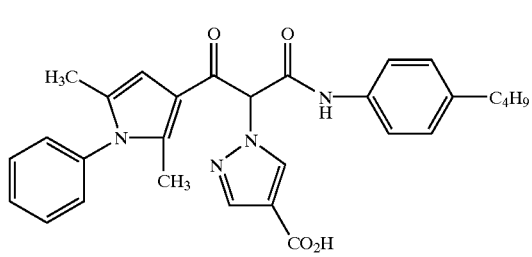
(53)
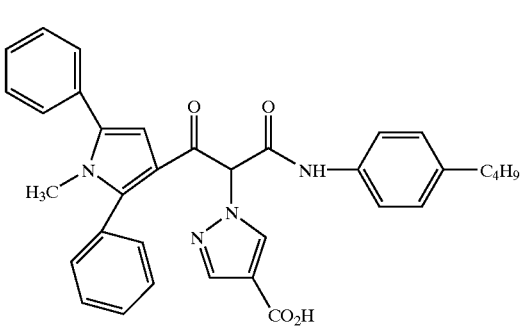
(54)
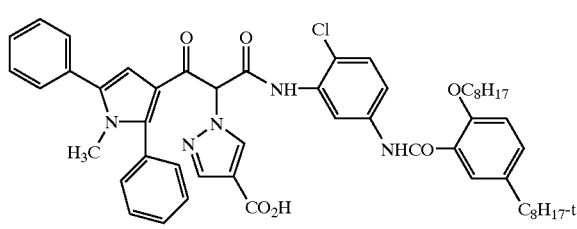
(55)
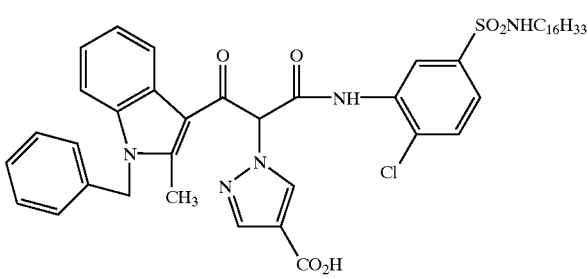
(56)
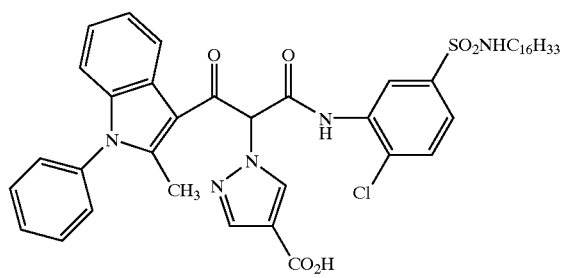
(57)
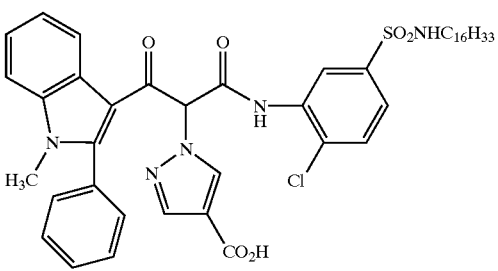
(58)
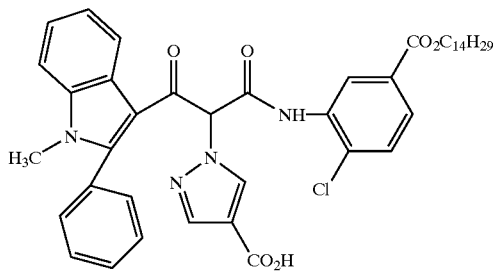
(59)
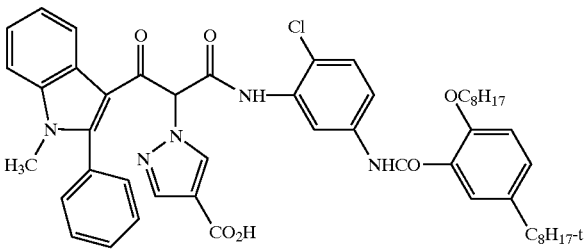
(60)

In the following description, if the above compounds (also referred to as "dye-forming couplers") are cited, they are indicated as "Coupler (X)" with respective parenthesized numbers "(x)" assigned to them.

The following are specific synthesis examples of compounds represented by the above formulae (I) to (VII).

Synthesis Example 1

Synthesis of Coupler (1)

Coupler (1) was synthesized by the following route:

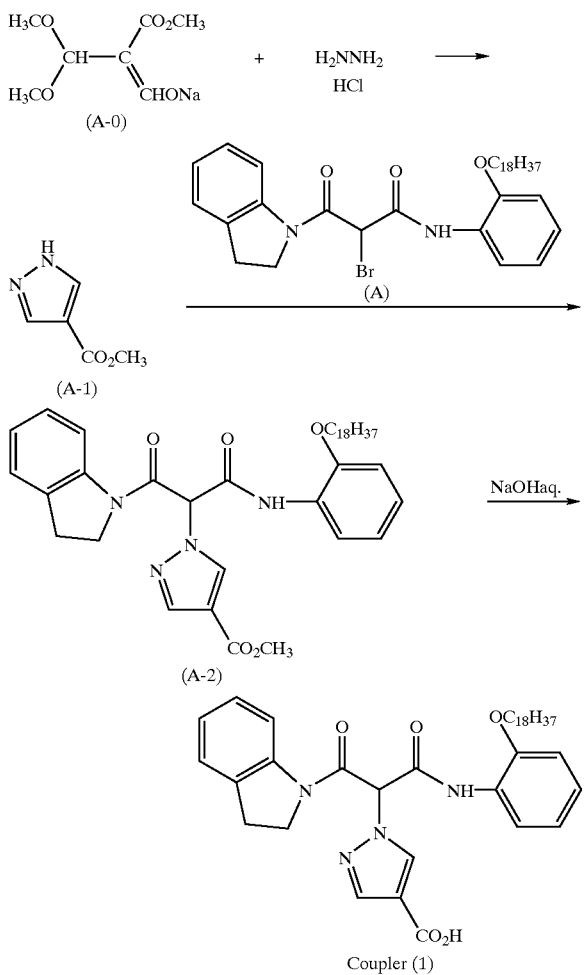

27.4 g of hydrazine hydrochloride was added to 1.0 liter (hereinafter also referred to as "L") of methyl alcohol solution containing 83.4 g of compound (A-0) (purity 95%), and stirred at room temperature overnight. Then, 400 milliliter (hereinafter also referred to as "mL") of water and 800 mL of ethyl ether were added thereto, and insoluble was filtered out. The filtrate was extracted with ethyl ether, and dried with anhydrous magnesium sulfate, and thereafter the solvent was evaporated under reduced pressure. Then, acetonitrile was used to crystallize 40.0 g of compound (A-1) therefrom.

4.5 mL of 1,8-diazabicyclo[5.4.0]-7-undecene was added to 50 mL of N,N-dimethylacetamide solution containing 3.4 g of compound (A-1). 6 mL of N,N-dimethylacetamide containing 6.3 g of compound (A) synthesized according to the method described in JP-A-5-11416 was dropped into the solution. After completion of dropping, the solution was stirred overnight at room temperature. Ethyl acetate and water were added to the solution to separate the solution, and an organic layer was washed with diluted aqueous hydrochloric acid, and brine. After the organic layer was dried with anhydrous magnesium sulfate, the solvent was evaporated under reduced pressure, and a mixed solvent of ethyl acetate and hexane was used to crystallize 6.1 g of compound (A-2) therefrom.

27 mL of 2N sodium hydroxide aqueous solution was added to a mixed solution of 20 mL of tetrahydrofuran and 55 mL of methyl alcohol containing 6.1 g of compound (A-2). The solution was stirred for 3 hours at 50° C. Then, the solution was neutralized by a diluted aqueous hydrochloric acid, and separated by adding ethyl acetate thereto. After an organic layer was dried with anhydrous magnesium sulfate, the solvent was evaporated under reduced pressure, and a mixed solvent of ethyl acetate and hexane was used to crystallize 5.3 g of Coupler (1) therefrom.

Synthesis Example 2

Synthesis of Coupler (2)

Coupler (2) was synthesized by the following route:

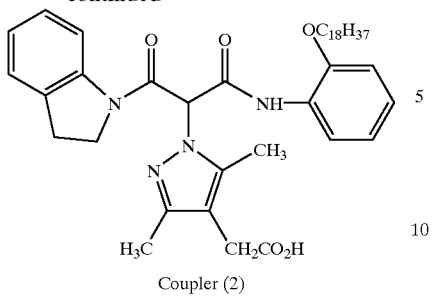

Coupler (2)

24.0 g of sodium hydride (60%) was stirred in a hexane, and the hexane was removed. 400 mL of tetrahydrofuran was added thereto and cooled by ice, and then 50 mL of tetrahydrofuran solution containing 50.0 g of acetylacetone was dropped into the mixture, and the mixture was stirred for 1 hour. Then, 50 mL of tetrahydrofuran solution containing 52.0 mL of ethyl α-bromoacetate was dropped into the mixture, and after dropping, the temperature of the mixture was gradually raised to room temperature. After being stirred for 4 hours, the mixture was poured into brine, and the resultant solution was separated with ethyl acetate and water. After an organic layer was dried with anhydrous magnesium sulfate, the solvent was evaporated under reduced pressure to obtain 69.9 g of oily compound (B-1).

14.5 g of hydrazine monohydrate was slowly added to 170 mL of ethyl alcohol solution containing 50 g of compound (B-1) under being cooled by ice. The temperature of the solution was raised to room temperature, and the solution was stirred overnight. The solution was separated by adding ethyl acetate and water, and an organic layer was washed with brine. The organic layer was dried with anhydrous magnesium sulfate, and then the solvent was evaporated under reduced pressure to obtain 44.6 g of oily compound (B-2).

6.7 mL of 1,8-diazabicyclo[5.4.0]-7-undecene was added to 100 mL of N,N-dimethylacetamide solution containing 7.6 g of compound (B-2). 10 mL of N,N-dimethylacetamide containing 9.4 g of the compound (A) was dropped into the solution. After completion of dropping, the solution was stirred overnight at room temperature. Ethyl acetate and water were added to the solution to separate the solution, and an organic layer was washed with diluted aqueous hydrochloric acid, and brine. After the organic layer was dried with anhydrous magnesium sulfate, the solvent was evaporated under reduced pressure, and a mixed solvent of ethyl acetate and hexane was used to crystallize 9.7 g of compound (B-3) therefrom.

30.0 mL of 2N sodium hydroxide aqueous solution was added to a mixed solution of 30 mL of tetrahydrofuran and 80 mL of methyl alcohol containing 7.2 g of compound (B-3). The solution was stirred for 3 hours at 50° C. Then, the solution was neutralized by a diluted hydrochloric acid solution, and ethyl acetate was added thereto for separation. After an organic layer was dried with anhydrous magnesium sulfate, the solvent was evaporated under reduced pressure, and a mixed solvent of ethyl acetate and hexane was used to crystallize 6.0 g of Coupler (2) therefrom.

Synthesis Example 3

Synthesis of Coupler (3)

Coupler (3) was synthesized by the following route:

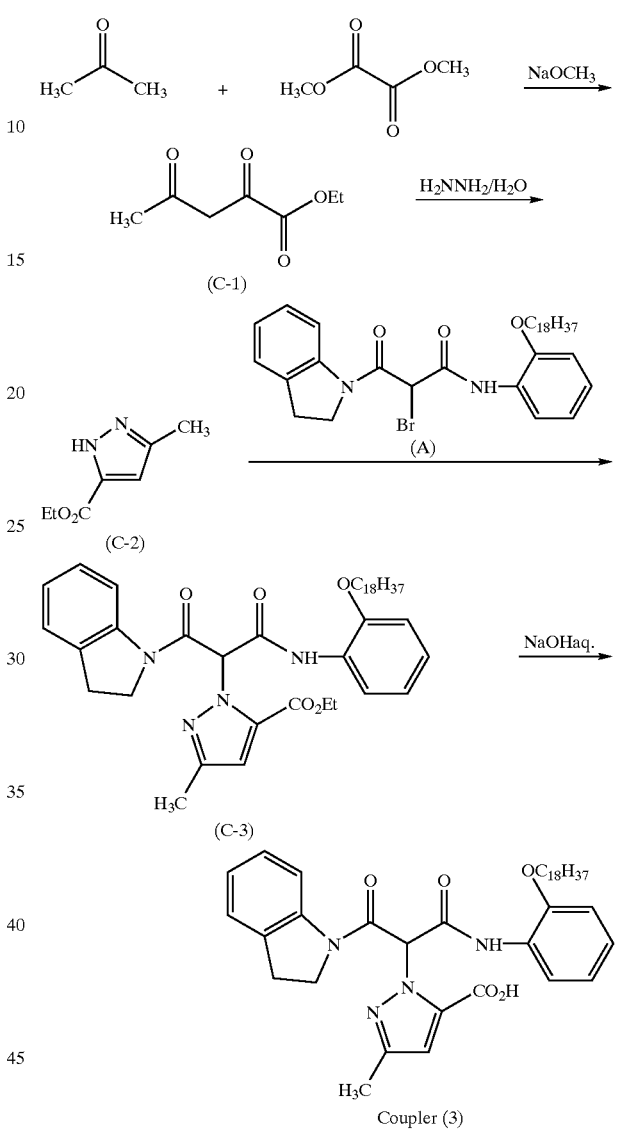

Coupler (3)

8.5 mL of acetone and 13.7 g of dimethyl oxalate were gradually added to 100 mL of methyl alcohol solution containing 9.41 g of sodium methoxide, and the solution was stirred for 3 hours while being heated under reflux. Then, the solution was cooled to room temperature, and thereafter concentrated under reduced pressure. After the mixture was changed to be acidic by diluted aqueous hydrochloric acid, extracted with ethyl acetate, and the organic layer was washed with brine. The organic layer was dried with anhydrous magnesium sulfate, then the solvent was evaporated under reduced pressure, and a mixed solvent of ethyl alcohol and hexane was used to crystallize 33.3 g of compound (C-1) therefrom.

10.5 g of hydrazine monohydrate was slowly added to 110 mL of ethyl alcohol solution containing 33.3 g of compound (C-1) while being cooled by ice. The temperature of the solution was raised to room temperature, and the solution was stirred overnight. The solution was separated by adding ethyl acetate and water, and an organic layer was washed with brine. After the organic layer was dried with anhydrous magnesium sulfate, the solvent was evaporated under reduced pressure, and a mixed solvent of ethyl acetate and hexane was used to crystallize 30.0 g of compound (C-2) therefrom.

6.7 mL of 1,8-diazabicyclo[5.4.0]-7-undecene was added to 100 mL of N,N-dimethylacetamide solution containing 6.9 g of compound (C-2). 10 mL of N,N-dimethylacetamide containing 9.4 g of the compound (A) was dropped into the solution. After completion of dropping, the solution was stirred overnight at room temperature. Ethyl acetate and water were added to the solution to separate the solution, and an organic layer was washed with diluted aqueous hydrochloric acid, and brine. After the organic layer was dried with anhydrous magnesium sulfate, the solvent was evaporated under reduced pressure to obtain 8.9 g of oily compound (C-3) therefrom.

30.0 mL of 2N sodium hydroxide aqueous solution was added to a mixed solution of 30 mL of tetrahydrofuran and 80 mL of methyl alcohol containing 7.0 g of compound (C-3). The solution was stirred for 3 hours at 50° C. Then, the solution was neutralized by a diluted aqueous hydrochloric acid, and separated by adding ethyl acetate thereto. After an organic layer was dried with anhydrous magnesium sulfate, the solvent was evaporated under reduced pressure, and a mixed solvent of ethyl acetate and hexane was used to crystallize 5.7 g of Coupler (3) therefrom.

Synthesis Example 4

Synthesis of Coupler (41)

Coupler (41) was synthesized by the following rout:

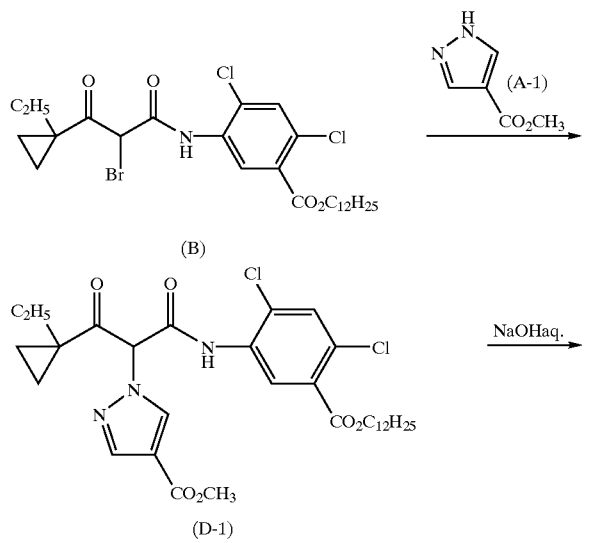

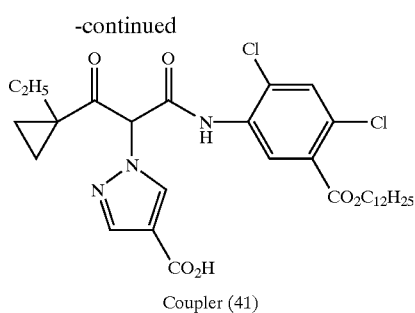

Coupler (41)

4.5 mL of 1,8-diazabicyclo[5.4.0]-7-undecene was added to 50 mL of N,N-dimethylacetamide solution containing 3.4 g of compound (A-1). 6 mL of N,N-dimethylacetamide containing 8.9 g of compound (B) synthesized according to the method described in JP-A-4-218042 was dropped into the solution. After the completion of dropping, the solution was stirred overnight at room temperature. Ethyl acetate and water were added to separate the solution, and an organic layer was washed with diluted aqueous hydrochloric acid and brine. After the organic layer was dried with anhydrous magnesium sulfate, the solvent was evaporated under reduced pressure, and a mixed solvent of ethyl acetate and hexane was used to crystallize 7.6 g of compound (D-1).

30 mL of 2N sodium hydroxide aqueous solution was added to a mixed solution of 20 mL of hetrahydrofuran and 55 mL of methyl alcohol containing 6.4 g of compound (D-1). The solution was stirred for 3 hours at 50° C. The solution was neutralized by diluted aqueous hydrochloric acid, and separated by adding ethyl acetate thereto. After an organic layer was dried with anhydrous magnesium sulfate, the solvent was evaporated under reduced pressure, and a mixed solvent of ethyl acetate and hexane was used to crystallize 4.5 g of coupler (41).

Synthesis Example 5

Synthesis of Coupler (51)

Coupler (51) was synthesized by the following rout:

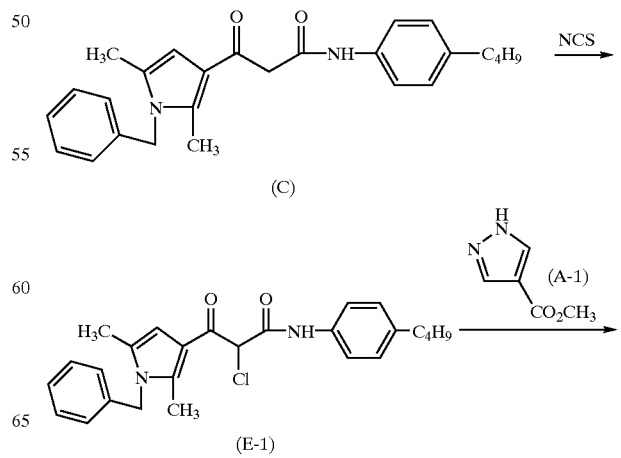

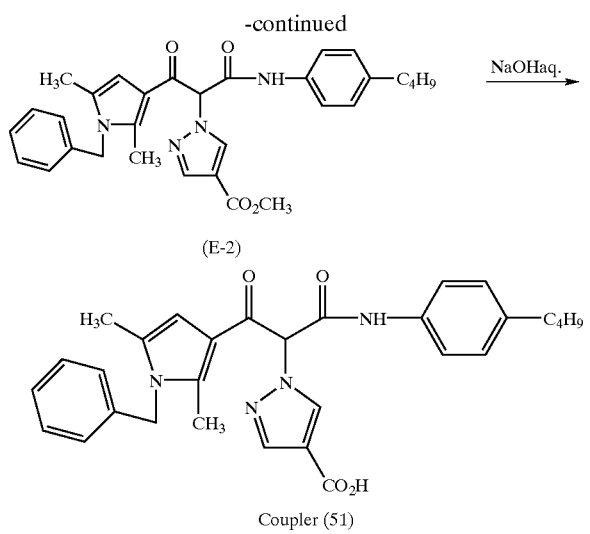

(E-2)

Coupler (51)

4.0 g of N-chlorosuccinimide (abbreviated to NCS) was added to 200 mL of dichloromethane containing 12.1 g of compound (C) synthesized according to the method described in U.S. Pat. No. 6,057,087, and stirred for 2 hours at room temperature. Ethyl acetate and water were added to separate the solution, and an organic layer was washed with diluted aqueous hydrochloric acid and brine. After the organic layer was dried with anhydrous magnesium sulfate, the solvent was evaporated under reduced pressure to obtain compound (E-1) as a crude product.

9.0 mL of 1,8-diazabicyclo[5.4.0]-7-undecene was added to 100 mL of N,N-dimethylacetamide solution containing 7.6 g of compound (A-1). 20 mL of N,N-dimethylacetamide containing compound (E-1) was added to this solution. After completion of dropping, the temperature was raised up to 70° C., and stirred for 4 hours. Ethyl acetate and water were added to separate the solution, and an organic layer was washed with diluted aqueous hydrochloric acid and brine. After the organic layer was dried with anhydrous magnesium sulfate, the solvent was evaporated under reduced pressure, and a mixed solvent of ethyl acetate and hexane was used to crystallize 10.2 g of compound (E-2).

30 mL of 2N sodium hydroxide aqueous solution was added to a mixed solution of 20 mL of hetrahydrofuran and 55 mL of methyl alcohol containing 7.9 g of compound (E-2). The solution was stirred for 3 hours at 50° C. The solution was neutralized by diluted aqueous hydrochloric acid, and separated by adding ethyl acetate thereto. After an organic layer was dried with anhydrous magnesium sulfate, the solvent was evaporated under reduced pressure, and a mixed solvent of ethyl acetate and hexane was used to crystallize 5.0 g of coupler (51).

(Silver halide photographic lightsensitive material)

The lightsensitive material of the present invention is a silver halide photographic lightsensitive material made by forming at least one lightsensitive layer on a support, in which at least one of said lightsensitive layer contains a dye-forming coupler which is a compound represented by the formulae (I) to (IV) or the formula (V), and the coupler is contained in a hydrophilic colloidal layer made of conventional gelatin binder. A general lightsensitive material can be formed by coating at least one blue-sensitive silver halide emulsion layer, at least one green-sensitive silver halide emulsion layer, and at least one red-sensitive silver halide emulsion layer, which are lightsensitive emulsion layers (lightsensitive layers), on a support. The layers may be coated in any order. Further, an infrared-sensitive silver halide emulsion layer can be used instead of one of the lightsensitive emulsion layers. It is possible to perform color reproduction of subtractive color process, by making each of these lightsensitive emulsion layers contain a silver halide emulsion having sensitivity to its wavelength range, and a coupler which forms dye having a complementary color relationship with light to which the emulsion is sensitive. However, a structure may be adopted in which the lightsensitive emulsion layer and the hue generated by the coupler contained therein have no relation as described above.

The dye forming couplers represented by the formulae (I) to (IV) or the formula (V) may be contained in any of the lightsensitive emulsion layers. The couplers are preferably contained in a blue-sensitive silver halide emulsion layer or green-sensitive silver halide emulsion layer, and especially preferably in a blue-sensitive silver halide emulsion layer.

The dye-forming couplers represented by the formulae (I) to (IV) or the formula (V) are mainly useful as yellow couplers or magenta couplers in the case of being used in combination with a color developing agent of p-phenylenediamines, and in particular useful as yellow couplers. Therefore, if the silver halide photographic lightsensitive material of the present invention uses p-phenylenediamines as its color developing agent, a dye forming coupler represented by the formulae (I) to (IV) or the formula (V) is preferably contained in a layer for generating yellow color or magenta color, and especially preferably contained in a layer for generating yellow color. Further, the dye-forming couplers represented by the formulae (I) to (IV) or the formula (V) are useful as dye-forming couplers which provide dyes of various hues in systems using color developing agents other than p-phenylenediamines.

In the silver halide photographic lightsensitive material of the present invention, $1 \times 10^{-3}$ to 1 mol of the coupler per mol of silver halide is preferably added, and more preferably $2 \times 10^{-3}$ to $3 \times 10^{-1}$ mol per mol of silver halide.

The couplers can be introduced into the lightsensitive material by various publicly-known dispersion methods. Preferable method is an oil-in-water dispersion method in which a coupler is dissolved in a high-boiling organic solvent (used in combination with a low-boiling organic solvent if necessary), the solution is dispersed by emulsification in an aqueous gelatin solution, and the dispersion is added to a silver halide emulsion. Examples of the high-boiling solvent used in the oil-in-water dispersion method are described, for example, in JP-A's-5-313327, 5-323539, 5-323541, 6-258803 and 8-262662, and U.S. Pat. No. 2,322, 027. Practical examples of steps, effects, and impregnating latexes of a latex dispersion method as one polymer dispersion method are described in, e.g., U.S. Pat. No. 4,199,363, West German Patent Application (OLS) Nos. 2,541,274 and 2,541,230, Jpn. Pat. Appln. KOKOKU Publication No. (hereinafter referred to as JP-B-) 53-41091, and EP029104. Further, dispersion using an organic solvent-soluble polymer is described in PCT International Publication WO88/00723, and JP-A-5-150420. The polymer is preferably methacrylate or acrylamide polymers, and especially preferably acrylamide polymers in respect of image fastness.

The term "high-boiling" indicates a boiling point of 175° C. or more under normal pressure.

Examples of the high-boiling solvent usable in the present invention are described in U.S. Pat. No. 2,322,027, etc. Specific examples of high-boiling organic solvents having a boiling point of 175° C. or more under normal pressure are phthalic acid esters (e.g., dibutyl phthalate, dicyclohexyl phthalate, di-2-ethylhexyl phthalate, decyl phthalate, bis(2,4-di-tert-amylphenyl)phthalate, bis(2,4-di-tert-amylphenyl) phthalate, and bis(1,1-diethylpropyl)phthalate), esters of phosphoric acid and phosphonic acid (e.g., triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, and di-2-ethylhexylphenyl phosphate), benzoic acid esters (e.g., 2-ethylhexyl benzoate, dodecyl benzoate, and 2-ethylhexyl-p-hydroxy benzoate), amides (e.g., N,N-diethyldodecanamide, N,N-diethyllaurylamide, and N-tetradecylpyrrolidone), sulfonamides (e.g., N-butylbenzenesulfonamide), alcohols or phenols (e.g., isostearyl alcohol and 2,4-di-tert-amylphenol), aliphatic carbonic acid esters (e.g., bis(2-ethylhexyl) sebacate, dioctyl azelate, glycerol tributyrate, isostearyl lactate, and trioctyl citrate), aniline derivatives (e.g., N,N-dibutyl-2-butoxy-5-tert-octylaniline), hydrocarbons (e.g., paraffin, dodecylbenzene, and diisopropylnaphthalene), and chlorinated paraffins. In particular, phosphoric esters and the hydrogen-donating compounds described in JP-A's-6-258803 and 8-262662 are excellent in respect of hue, and can be preferably used.

Further, to reduce loads on environments, EP-969320A1 or EP-969321A1 are preferably used instead of phthalic acid esters. In addition to them, tributyl citrate and pentaglycerin triester can be used.

Although the dielectric constant of the high-boiling organic solvent varies according to the object, it is preferably 2.0 to 7.0, and more preferably 3.0 to 6.0.

The weight ratio of a high-boiling organic solvent to a coupler of the invention, is preferably 0 to 10, and more preferably, 0 to 4.

As a co-solvent, it is also possible to use an organic solvent, e.g., ethyl acetate, butyl acetate, ethyl propionate, methylethylketone, cyclohexanone, 2-ethoxyethyl acetate, and dimethylformamide, having a boiling point of 30° C. or more, preferably 50° C. to about 160° C.

From the viewpoint of improvement in aging stability during storage in a state of emulsified dispersion, and inhibition of change in photographic property and improvement in aging stability as a final coating composition made by being mixed with an emulsion, all or a part of the co-solvent can be removed from the emulsified dispersion according to necessity, by means of reduced-pressure distillation, noodle washing or ultrafiltration.

An average grain size (diameter) of lipophilic fine-grain dispersion obtained as described above is preferably 0.001 to 1.0 μm, more preferably 0.05 to 0.30 μm, and most preferably 0.08 to 0.20 μm. The average grain size can be measured by using a Coulter submicron grain analyzer model N4 (manufactured by Coulter Electronics Company), etc. A large average grain size of the lipophilic fine-grain dispersion is apt to cause problems such as decrease of the color formation efficiency of the coupler, and deterioration of gloss of the surface of the lightsensitive material. A too small grain size raises viscosity of the dispersion, which makes it difficult to handle at the time of manufacturing.

The use amount, in a weight ratio, of the lipophilic fine-grain dispersion comprising couplers of the present invention to the dispersion medium is preferably 2 to 0.1 with respect to dispersion medium, and more preferably 1.0 to 0.2. As the dispersion medium, gelatin is representative, and hydrophilic polymer such as polyvinyl alcohol can be used. The lipophilic fine-grain dispersion can contain various compounds according to its object, along with the coupler of the present invention.

In the lightsensitive material used in the present invention, at least one red-sensitive layer, green sensitive layer and blue-sensitive layer may be provided on a support. A typical example is a silver halide photographic lightsensitive material having at least one lightsensitive layer comprising a plurality of silver halide emulsion layers, which have substantially the same color sensitivity, but different in speed, on a support. The lightsensitive layer is a unit lightsensitive layer having color sensitivity to any one of blue light, green light and red light. In a multi-layer silver halide color photographic lightsensitive material, generally unit lightsensitive layers are arranged in the order of red-sensitive layer, green-sensitive layer, and blue-sensitive layer from the support. However, according to its object, the above order of arrangement may be reversed, and an order of arrangement in which color-sensitive layers of the same color is interposed with a color-sensitive layer of a different color. A non-lightsensitive layer may be provided between the silver halide lightsensitive layers, and as a top layer and a bottom layer. Such layers may contain couplers described below, DIR compounds and a color mixing prevention agent. In the plurality of silver halide emulsion layers constituting each unit lightsensitive layer, as described in DE 1,121,470 or GB 923,045, the disclosures of which are incorporated herein by reference, two layers consisting of a high-speed emulsion layer and a low-speed emulsion layer are arranged such that the speeds sequentially decrease toward the support. Further, as described in JP-A's-57-112751, 62-200350, 62-206541 and 62-206543, the disclosures of which are incorporated herein by reference, a low-speed emulsion layer may be disposed on the side distant from the support, and a high-speed emulsion layer on the side close to the support.

As specific examples of the order of arrangement, the layers can be arranged in the order of low-speed blue-sensitive layer (BL)/high-speed blue-sensitive layer (BH)/high-speed green sensitive layer (GH)/low-speed green sensitive layer (GL)/high-speed red-sensitive layer (RH)/low-speed red-sensitive layer (RL) from the side most distant from the support, the order of BH/BL/GL/GH/RH/RL, or BH/BL/GH/GL/RL/RH, etc.

Further, as described in JP-B-55-34932, the disclosure of which is incorporated herein by reference, they can be arranged in the order of blue-sensitive layers/GH/RH/GL/RL from the side most distant from the support. Furthermore, as described in JP-A's-56-25738 and 62-63936, the disclosures of which are incorporated herein by reference, they can be arranged in the order of blue-sensitive layers/GL/RL/GH/RH from the side most distant from the support.

Further, as described in JP-B-49-15495, the disclosure of which is incorporated herein by reference, an arrangement can be used in which three layers having different speeds are arranged such that the sensitivity gradually decreases toward the support. In the arrangement, a silver halide emulsion layer having the highest speed is arranged as an upper layer, silver halide emulsion layer having speed lower than the sensitivity of the upper layer as a middle layer, and silver halide emulsion layer having speed further lower than that of the middle layer as a lower layer.

Also in the case where a lightsensitive layer is formed of three layers having different speeds, as described in JP-A-59-202464, the disclosure of which is incorporated herein by reference, the layers sensitive to the same color may be arranged in the order of medium-speed emulsion layer/high-speed emulsion layer/low-speed emulsion layer from the side distant from the support.

Besides, they may be arranged in the order of high-speed emulsion layer/low-speed emulsion layer/medium-speed emulsion layer, or low-speed emulsion layer/medium-speed emulsion layer/high-speed emulsion layer.

Further, also in the case where a lightsensitive layer unit is formed of four or more layers, the layer arrangement may be changed as described above.

Furthermore, interlayer-inhibiting effect is preferably used as means for improving color reproduction. It is preferable that the weight-averaged wavelength ($\lambda_{-R}$) of spectral sensitivity distribution of interlayer effect exerted on the red-sensitive silver halide emulsion layer (if there are a plurality of red-sensitive layers, on the whole plural layers) from other silver halide emulsion layers in a region of 500 nm to 600 nm meets the relationship: 500 nm$<\lambda_{-R}\leq$560 nm, that the weight-averaged wavelength ($\lambda_G$) of spectral sensitivity distribution of the green-sensitive silver halide emulsion layer (if there are plural green layers, the whole plural layers) meets the relationship: 520 nm$<\lambda_G\leq$580 nm, and that the weight-average sensitivity wavelength, $\lambda_G$ and $\lambda_{-R}$ meet the relationship: $\lambda_G-\lambda_{-R}\geq$5 nm.

The spectral sensitizer and solid disperse dye used herein can be those described in JP-A-11-305396, the disclosure of which is incorporated herein by reference. The above weight-averaged wavelength of spectral sensitivity distribution of interlayer effect exerted on the red-sensitive silver halide emulsion layer from other layer can be obtained by the methods described in JP-A-11-305396.

The silver halide photographic lightsensitive material used in the present invention preferably contains at least one compound which reacts with a developing agent in an oxidized form obtained by development to thereby release a development inhibitor or a precursor thereof. For example, use can be made of DIR (development inhibitor-releasing) couplers, and a coupler capable of releasing DIR-hydroquinone or a coupler capable of releasing DIR hydroquinone or a precursor thereof.

Although, for example, the size and configuration of silver halide grains for use in the layer capable of exerting an interlayer effect on the red-sensitive layer are not particularly limited, it is preferred to use so-called tabular grains of high aspect ratio, a monodisperse emulsion having uniform grain size, or silver iodobromide grains having an iodine layer structure. Further, to extend an exposure latitude, it is preferred to mix two or more kinds of emulsions whose grain sizes are different from each other.

Although the donor layer capable of exerting the interlayer effect on the red-sensitive layer may be provided by coating on any position on the support, it is preferred that the donor layer be provided by coating at a position which is closer to the support than the blue-sensitive layer and which is more remote from the support than the red-sensitive layer. It is further preferred that the donor layer be positioned closer to the support than the yellow filter layer.

It is more preferred that the donor layer capable of exerting the interlayer effect on the red-sensitive layer be provided at a position which is closer to the support than the green-sensitive layer and which is more remote from the support than the red-sensitive layer. The donor layer is most preferably arranged at a position neighboring to a side of the green-sensitive layer close to the support. The terminology "neighboring" used herein means that an intermediate layer or any other thing is not interposed therebetween.

There may be a plurality of layers capable of exerting the interlayer effect on the red-sensitive layer. These layers may be positioned so that they neighbor to each other or are apart from each other.

The emulsion for use in the lightsensitive material of the present invention may be any of the surface latent image type in which latent images are mainly formed on the surface, the internal latent image type in which latent images are formed in the internal portion of grains and the type in which latent images exist in both the surface and the internal portion of grains. However, it is requisite that the emulsion be a negative type. The emulsion of the internal latent image type may specifically be, for example, a core/shell internal-latent-image type emulsion described in JP-A-63-264740, the disclosure of which is incorporated herein by reference, whose productive process is described in JP-A-59-133542. The thickness of the shell of this emulsion, although varied depending on development processing, etc., is preferably in the range of 3 to 40 nm, more preferably 5 to 20 nm.

The silver halide emulsion is generally subjected to physical ripening, chemical sensitization and spectral sensitization before use. Additives employed in these steps are described in RD Nos. 17643, 18716 and 307105. Positions where the description is made are listed in the following table.

With respect to the lightsensitive material of the present invention, at least two emulsions which are different from each other in at least one of the characteristics of the grain size, grain size distribution, halogen composition, grain configuration and speed of lightsensitive silver halide emulsion, can be mixed together and used in one layer.

It is preferred that silver halide grains having a grain surface fogged as described in U.S. Pat. No. 4,082,553, silver halide grains having a grain internal portion fogged as described in U.S. Pat. No. 4,626,498 and JP-A-59-214852, the disclosures of which are incorporated herein by reference, and colloidal silver be used in lightsensitive silver halide emulsion layers and/or substantially non-lightsensitive hydrophilic colloidal layers. The expression "silver halide grains having a grain surface or grain internal portion fogged" refers to silver halide grains which can be developed uniformly (non-imagewise) irrespective of the unexposed or exposed zone of lightsensitive material. The process for producing them is described in U.S. Pat. No. 4,626,498 and JP-A-59-214852. The silver halides constituting internal nuclei of core/shell silver halide grains having a grain internal portion fogged may have different halogen composition. Any of silver chloride, silver chlorobromide, silver iodobromide and silver chloroiodobromide can be used as the silver halide having a grain surface or grain internal portion fogged. The average grain size of these fogged silver halide grains is preferably in the range of 0.01 to 0.75 $\mu$m, especially preferably 0.05 to 0.6 $\mu$m. With respect to grain configuration, although both regular grains and a polydisperse emulsion can be used, monodispersity (at least 95% of the weight or number of silver halide grains have grain sizes falling within ±40% of the average grain size) is preferred.

In the present invention, it is preferred to use nonlight-sensitive fine grain silver halide. The expression "nonlight-sensitive fine grain silver halide" refers to silver halide fine grains which are not sensitive to light at the time of imagewise exposure for obtaining dye image and which are substantially not developed at the time of development processing thereof. Those not fogged in advance are preferred. The fine grain silver halide has a silver bromide content of 0 to 100 mol %, and, if necessary, may contain silver chloride and/or silver iodide. Preferably, silver iodide is contained in an amount of 0.5 to 10 mol %. The average grain size (average of equivalent circle diameter of projected area) of fine grain silver halide is preferably in the range of 0.01 to 0.5 μm, more preferably 0.02 to 0.2 μm.

The fine grain silver halide can be prepared by the same process as used in the preparation of common lightsensitive silver halide. It is not needed to optically sensitize the surface of silver halide grains. Further, a spectral sensitization thereof is also unnecessary. However, it is preferred to add known stabilizers such as triazoles, azaindenes, benzothiazoliums and mercapto compounds and zinc compounds thereto prior to the addition thereof to a coating liquid. Colloidal silver can be contained in the fine grain silver halide grain-containing layer.

The above various additives can be used in the lightsensitive material according to the present technology, to which other various additives can also be added in conformity with the object.

These additives are described in detail in Research Disclosure Item 17643 (December 1978), Item 18716 (November 1979) and Item 308119 (December 1989), the disclosures of which are incorporated herein by reference. A summary of the locations where they are described will be listed in the following table.

| Types of additives | RD17643 | RD18716 | RD308119 |
|---|---|---|---|
| 1 Chemical-sensitizers | page 23 | page 648 right column | page 996 |
| 2 Sensitivity increasing agents | | page 648 right column | |
| 3 Spectral sensitizers, super-sensitizers | pages 23–24 | page 648, right column to page 649, right column | page 996, right column to page 998, right column |
| 4 Brighteners | page 24 | | page 998 right column |
| 5 Antifoggants, and stabilizers | pages 24–25 | page 649 right column | page 998, right column to page 1000, right column |
| 6 Light absorbents, filter dyes, ultraviolet absorbents | pages 25–26 | page 649, right column to page 650, left column | page 1003, left column to page 1003, right column |
| 7 Stain-preventing agents | page 25, right column | page 650, left to right columns | page 1002, right column |
| 8 Dye image stabilizers | page 25 | | page 1002, right column |
| 9 Film hardeners | page 26 | page 651, left column | page 1004, right column to page 1005, left column |
| 10 Binders | page 26 | page 651, left column | page 1003, right column to page 1004, right column |
| 11 Plasticizers, lubricants | page 27 | page 650, right column | page 1006, left to right columns |
| 12 Coating aids, surfactants | pages 26–27 | page 650, right column | page 1005, left column to page 1006, left column |
| 13 Antistatic agents | page 27 | page 650, right column | page 1006, right column to page 1007, left column |
| 14 Matting agents | | | page 1008, left column to page 1009, left column. |

In the lightsensitive material of the present invention, various dye-forming couplers can be used in combination with the couplers represented by the formulae (I) to (VII) of the present invention. The following couplers are especially preferable.

Yellow couplers: couplers represented by formulas (I) and (II) in EP No. 502,424A; couplers represented by formulas (1) and (2) in EP No. 513,496A (in particular, Y-28 on page 18); a coupler represented by formula (I) in claim 1 of EP No. 568,037A; a coupler represented by general formula (I) in column 1, lines 45 to 55, in U.S. Pat. No. 5,066,576; a coupler represented by general formula (I) in paragraph 0008 of JP-A-4-274425; couplers described in claim 1 on page 40 in EP No. 498,381A1 (in particular, D-35 on page 18); couplers represented by formula (Y) on page 4 in EP No. 447,969A1 (in particular, Y-1 (page 17) and Y-54 (page 41)); and couplers represented by formulas (II) to (IV) in column 7, lines 36 to 58, in U.S. Pat. No. 4,476,219 (in particular, II-17, II-19 (column 17), and II-24 (column 19)), the disclosures of the above documents disclosing the yellow couplers are incorporated herein by reference.

Magenta couplers: JP-A-3-39737 (L-57 (page 11, lower right column), L-68 (page 12, lower right column), and L-77 (page 13, lower right column); [A-4]-63 (page 134), and [A-4]-73 and -75 (page 139) in EP No. 456,257; M-4 and -6 (page 26), and M-7 (page 27) in EP No. 486,965; M-45 (page 19) in EP No. 571,959A; (M-1) (page 6) in JP-A-5-204106; and M-22 in paragraph 0237 of JP-A-4-362631, the disclosures of the above documents disclosing the magenta couplers are incorporated herein by reference.

Cyan couplers: CX-1, CX-3, CX-4, CX-5, CX-11, CX-12, CX-14, and CX-15 (pages 14 to 16) in JP-A-4-204843; C-7 and C-10 (page 35), C-34 and C-35 (page 37), and (I-1) and (I-17) (pages 42 and 43) in JP-A-4-43345; and couplers represented by general formulas (Ia) and (Ib) in claim 1 of JP-A-6-67385, the disclosures of the above documents disclosing the cyan couplers are incorporated herein by reference.

Polymer couplers: P-1 and P-5 (page 11) in JP-A-2-44345, the disclosure of which is incorporated herein by reference.

Couplers for forming a colored dye with a proper diffusibility are preferably those described in U.S. Pat. No. 4,366,237, GB No. 2,125,570, EP No. 96,873B, and DE No. 3,234,533, the disclosures of which are incorporated herein by reference.

As couplers for correcting the unnecessary absorption of a colored dye, preferred use is made of, yellow colored cyan couplers represented by formulas (CI), (CII), (CIII), and (CIV) described on page 5 in EP No. 456,257A1 (in particular, YC-86 on page 84); yellow colored magenta couplers ExM-7 (page 202), Ex-1 (page 249), and EX-7 (page 251) described in EP No. 456,257A1; magenta colored cyan couplers CC-9 (column 8) and CC-13 (column 10) described in U.S. Pat. No. 4,833,069; (2) (column 8) in U.S. Pat. No. 4,837,136; and colorless masking couplers represented by formula (A) in claim 1 of WO No. 92/11575 (in particular, compound examples on pages 36 to 45), the disclosures of all the documents disclosing the couplers for correcting the unnecessary absorption of a colored dye are incorporated herein by reference.

Examples of compounds (including a coupler) which react with a developing agent in an oxidized form to thereby release a photographically useful compound residue are as follows. Development inhibitor-releasing compounds: compounds represented by formulas (I), (II), (III), and (IV) on page 11 of EP No. 378,236A1 (in particular, T-101 (page 30), T-104 (page 31), T-113 (page 36), T-131 (page 45), T-144 (page 51), and T-158 (page 58)); a compound represented by formula (I) on page 7 of EP No. 436,938A2 (in particular, D-49 (page 51)); a compound represented by formula (1) in EP No. 568,037A (in particular, (23) (page 11)); and compounds represented by formulas (I), (II), and (III) on pages 5 and 6 of EP No. 440,195A2 (in particular, I-(1) on page 29). Bleaching accelerator-releasing compounds: compounds represented by formulas (I) and (I') on page 5 of EP No. 310,125A2 (in particular, (60) and (61) on page 61); and compounds represented by formula (I) in claim 1 of JP-A-6-59411 (in particular, (7) (page 7)). Ligand-releasing compounds: compounds represented by LIG-X described in claim 1 of U.S. Pat. No. 4,555,478 (in particular, compounds in column 12, lines 21 to 41). Leuco dye-releasing compounds: compounds 1 to 6 in columns 3 to 8 of U.S. Pat. No. 4,749,641. Fluorescent dye-releasing compounds: compounds represented by COUP-DYE in claim 1 of U.S. Pat. No. 4,774,181 (in particular, compounds 1 to 11 in columns 7 to 10). Development accelerator or fogging agent-releasing compounds: compounds represented by formulas (1), (2), and (3) in column 3 of U.S. Pat. No. 4,656,123 (in particular, (I-22) in column 25); and ExZK-2 on page 75, lines 36 to 38, in EP No. 450,637A2. Compounds which release a group that does not function as a dye unless it splits off: compounds represented by formula (I) in claim 1 of U.S. Pat. No. 4,857,447 (in particular, Y-1 to Y-19 in columns 25 to 36).

Preferable examples of additives other than couplers are as follows.

Dispersion mediums of an oil-soluble organic compound: P-3, P-5, P-16, P-19, P-25, P-30, P-42, P-49, P-54, P-55, P-66, P-81, P-85, P-86, and P-93 (pages 140 to 144) in JP-A-62-215272. Impregnating latexes of an oil-soluble organic compound: latexes described in U.S. Pat. No. 4,199,363. Scavengers of developing agent in an oxidized form: compounds represented by formula (I) in column 2, lines 54 to 62, in U.S. Pat. No. 4,978,606 (in particular, I-(1), I-(2), I-(6), and I-(12) (columns 4 and 5)), and formulas in column 2, lines 5 to 10, in U.S. Pat. No. 4,923,787 (in particular, compound 1 (column 3)). Stain inhibitors: formulas (I) to (III) on page 4, lines 30 to 33, in particular I-47, I-72, III-1, and III-27 (pages 24 to 48) in EP No. 298321A. Discoloration inhibitors: A-6, A-7, A-20, A-21, A-23, A-24, A-25, A-26, A-30, A-37, A-40, A-42, A-48, A-63, A-90, A-92, A-94, and A-164 (pages 69 to 118) in EP No. 298,321A; II-1 to III-23, in particular III-10, in columns 25 to 38 of U.S. Pat. No. 5,122,444; I-1 to III-4, in particular II-2, on pages 8 to 12 in EP No. 471,347A; and A-1 to A-48, in particular A-39 and A-42, in columns 32 to 40 of U.S. Pat. No. 5,139,931. Materials which reduce the use amount of a color enhancer or a color amalgamation inhibitor: I-1 to II-15, in particular I-46, on pages 5 to 24 in EP No. 411,324A. Formalin scavengers: SCV-1 to SCV-28, in particular SCV-8, on pages 24 to 29 in EP No. 477,932A. Film hardeners: H-1, H-4, H-6, H-8, and H-14 on page 17 in JP-A-1-214845; compounds (H-1 to H-54) represented by formulas (VII) to (XII) in columns 13 to 23 of U.S. Pat. No. 4,618,573;, compounds (H-1 to H-76), in particular H-14, represented by formula (6) on page 8, lower right column, in JP-A-2-214852; and compounds described in claim 1 of U.S. Pat. No. 3,325,287. Development inhibitor precursors: P-24, P-37, and P-39 (pages 6 and 7) in JP-A-62-168139; and compounds described in claim 1, in particular 28 and 29 in column 7, of U.S. Pat. No. 5,019,492. Antiseptic agents and mildewproofing agents; I-1 to III-43, in particular II-1, II-9, II-10, II-18, and III-25, in columns 3 to 15 of U.S. Pat. No. 4,923,790. Stabilizers and antifoggants: I-1 to (14), in particular I-1, I-60, (2), and (13), in columns 6 to 16 of U.S. Pat. No. 4,923,793; and compounds 1 to 65, particularly compound 36, in columns 25 to 32 of U.S. Pat. No. 4,952,483. Chemical sensitizers: triphenylphosphine, selenide, and compound 50 in JP-A-5-40324. Dyes: a-1 to b-20, in particular a-1, a-12, a-18, a-27, a-35, a-36, and b-5, on pages 15 to 18 and V-1 to V-23, in particular V-1, on pages 27 to 29 in JP-A-3-156450; F-I-1 to F-II-43, in particular F-I-11 and F-II-8, on pages 33 to 55 in EP No. 445,627A; III-1 to III-36, in particular III-1 and III-3, on pages 17 to 28 in EP No. 457,153A; microcrystalline dispersions of Dye-1 to Dye-124 on pages 8 to 26 in WO No. 88/04794; compounds 1 to 22, in particular compound 1, on pages 6 to 11 in EP No. 319,999A; compounds D-1 to D-87 (pages 3 to 28) represented by formulas (1) to (3) in EP No. 519,306A; compounds 1 to 22 (columns 3 to 10) represented by formula (I) in U.S. Pat. No. 4,268,622; and compounds (1) to (31) (columns 2 to 9) represented by formula (I) in U.S. Pat. No. 4,923,788. UV absorbents: compounds (18b) to (18r) and 101 to 427 (pages 6 to 9) represented by formula (1) in JP-A-46-3335; compounds (3) to (66) (pages 10 to 44) represented by formula (I) and compounds HBT-1 to HBT-10 (page 14) represented by formula (III) in EP No. 520,938A; and compounds (1) to (31) (columns 2 to 9) represented by formula (1) in EP No. 521,823A.

The present invention can be applied to various color lightsensitive materials such as color negative films for general purposes or cinemas, color reversal films for slides and TV, color paper, color positive films and color reversal paper. Moreover, the present invention is suitable to lens equipped film units described in JP-B-2-32615 and Jpn. Utility Model Appln. KOKOKU Publication No. 3-39784.

Supports which can be suitably used in the present invention are described in, e.g., RD. No. 17643, page 28; RD. No. 18716, from the right column of page 647 to the left column of page 648; and RD. No. 307105, page 879.

In the lightsensitive material of the present invention, the total film thickness from the lightsensitive silver halide layer nearest to the support to the surface of the photographic lightsensitive material is preferably 24 $\mu$m or less, and more preferably 22 $\mu$m or less. Film swelling speed $T_{1/2}$ is preferably 30 sec or less, and more preferably 20 sec or less. The film swelling speed $T_{1/2}$ is defined as the time that, when the saturation film thickness means 90% of the maximum swollen film thickness realized by the processing in a color developing solution at 30° C. for 3 min 15 sec, spent for the film thickness to reach ½ of the saturation film thickness.

The film thickness means one measured under moisture conditioning at 25° C. and at a relative humidity of 55% (two days). The film swelling speed $T_{1/2}$ can be measured by using a swellometer described in A. Green et al., Photogr. Sci. Eng., Vol. 19, No. 2, pp. 124 to 129. The film swelling speed $T_{1/2}$ can be regulated by adding a film hardening agent to gelatin as a binder or by changing aging conditions after coating. The swelling ratio preferably ranges from 150 to 400%. The swelling ratio can be calculated from the maximum swollen film thickness measured under the above conditions in accordance with the formula:

(maximum swollen film thickness−film thickness)/film thickness.

In the lightsensitive material of the present invention, hydrophilic colloid layers (called "back layers") having a total dried film thickness of 2 to 20 $\mu$m are preferably formed on the side opposite to the side having emulsion layers. The back layers preferably contain the above light absorbent, filter dye, ultraviolet absorbent, antistatic agent, film hardener, binder, plasticizer, lubricant, coating aid and surfactant. The swelling ratio of the back layers is preferably 150% to 500%.

The lightsensitive material of the present invention can be developed by conventional methods described in RD. No. 17643, pages 28 and 29; RD. No. 18716, page 651, left to right columns; and RD No. 307105, pages 880 and 881.

The color negative film processing solution for use in the present invention will be described below.

The compounds listed from page 9, right upper column, line 1 to page 11, left lower column, line 4 of JP-A-4-121739 can be used in the color developing solution for use in the present invention. Preferred color developing agents for use in especially rapid processing are
2-methyl-4-[N-ethyl-N-(2-hydroxyethyl)amino]aniline,
2-methyl-4-[N-ethyl-N-(3-hydroxypropyl)amino]aniline and
2-methyl-4-[N-ethyl-N-(4-hydroxybutyl)amino]aniline.

These color developing agents are preferably used in an amount of 0.01 to 0.08 mol, more preferably 0.015 to 0.06 mol, and much more preferably 0.02 to 0.05 mol per liter (L) of the color developing solution. The replenisher of the color developing solution preferably contains the color developing agent in an amount corresponding to 1.1 to 3 times the above concentration, and more preferably 1.3 to 2.5 times the above concentration.

Hydroxylamine can widely be used as preservatives of the color developing solution. When enhanced preserving properties are required, it is preferred to use hydroxylamine derivatives having substituents for example, alkyl, hydroxyalkyl, sulfoalkyl and carboxyalkyl groups, examples of which include N,N-di(sulfoehtyl)hydroxylamine, monomethylhydroxylamine, dimethylhydroxylamine, monoethylhydroxylamine, diethylhydroxylamine and N,N-di(carboxyethyl)hydroxylamine. Of these, N,N-di(sulfoehtyl)hydroxylamine is especially preferred. Although these may be used in combination with the hydroxylamine, it is preferred that one or at least two members thereof be used in place of the hydroxylamine.

The preservatives are preferably used in an amount of 0.02 to 0.2 mol, more preferably 0.03 to 0.15 mol, and most preferably 0.04 to 0.1 mol per liter of the color developing solution. The replenisher of the color developing solution preferably contains the preservative in an amount corresponding to 1.1 to 3 times the concentration of the mother liquor (processing tank solution) as in the color developing agent.

Sulfites are used as tarring preventives for the color developing agent in an oxidized form in the color developing solution. Each sulfite is preferably used in the color developing solution in an amount of 0.01 to 0.05 mol, more preferably 0.02 to 0.04 mol per liter, and is preferably used in the replenisher in an amount corresponding to 1.1 to 3 times the above concentration.

The pH value of the color developing solution preferably ranges from 9.8 to 11.0, more preferably from 10.0 to 10.5. That of the replenisher is preferably set at 0.1 to 1.0 higher than the above value. Common buffers such as carbonate, phosphonate, sulfosalicylate and borate are used for stabilizing the above pH value.

Although the amount of the replenisher of the color developing solution preferably ranges from 80 to 1300 mL per $m^2$ of the lightsensitive material, it is desired that the amount be smaller from the viewpoint of reducing environmental pollution load. Specifically, the amount of the replenisher more preferably ranges from 80 to 600 mL, most preferably from 80 to 400 mL.

Although the bromide ion concentration of the color developing solution generally ranges from 0.01 to 0.06 mol per liter, it is preferred that the above concentration be set at 0.015 to 0.03 mol per liter for inhibiting fog while maintaining sensitivity to thereby improve discrimination and for bettering graininess. When the bromide ion concentration is set so as to fall within the above range, the replenisher preferably contains bromide ion in a concentration as calculated by the following formula. However, when C is negative, it is preferred that no bromide ion be contained in the replenisher.

$$C=A-W/V$$

wherein
C: bromide ion concentration of the color developing replenisher (mol/L),
A: target bromide ion concentration of the color developing solution (mol/L),
W: amount of bromide ion leached from the lightsensitive material into the color developing solution when a color development of 1 $m^2$ of the lightsensitive material has been carried out (mol), and
V: amount of color developing replenisher supplied per $m^2$ of the lightsensitive material (L).

Development accelerators such as pyrazolidones represented by 1-phenyl-3-pyrazolidone and 1-phenyl-2-methyl-2-hydroxymethyl-3-pyrazolidone and thioether compounds represented by 3,6-dithia-1,8-octanediol are preferably used for means for enhancing sensitivity when the amount of the replenisher has been reduced or when a high bromide ion concentration has been set.

Compounds and processing conditions described on page 4, left lower column, line 16 to page 7, left lower column, line 6 of JP-A-4-125558 can be applied to the processing solution having bleaching capability for use in the present invention.

Bleaching agents having redox potentials of at least 150 mV are preferably used. Specifically, suitable examples thereof are those described in JP-A-5-72694 and JP-A-5-173312, and especially suitable examples thereof are 1,3-diaminopropanetetraacetic acid, and ferric complex salts of Example 1 compounds listed on page 7 of JP-A-5-173312.

For improving the biodegradability of the bleaching agent, it is preferred that ferric complex salts of compounds listed in JP-A's-4-251845, and 4-268552, EP Nos. 588289, and 591934 and JP-A-6-208213 be used as the bleaching agent. The concentration of the above bleaching agent preferably ranges from 0.05 to 0.3 mol per liter of the solution having bleaching capability, and it is especially preferred that a design be made at 0.1 to 0.15 mol per liter for reducing the discharge to the environment. When the solution having bleaching capability is a bleaching solution, a bromide is preferably incorporated therein in an amount of 0.2 to 1 mol, more preferably 0.3 to 0.8 mol per liter.

Each component is incorporated in the replenisher of the solution having bleaching capability fundamentally in a concentration calculated by the following formula. This enables holding the concentration of the mother liquor constant.

$$C_R = C_T \times (V_1 + V_2)/V_1 + C_P$$

$C_R$: concentration of each component in the replenisher,
$C_T$: concentration of the component in the mother liquor (processing tank solution),
$C_P$: component concentration consumed during processing,
$V_1$: amount of replenisher having bleaching capability supplied per $m^2$ of lightsensitive material (mL), and
$V_2$: amount carried from previous bath by 1 $m^2$ of lightsensitive material (mL).

In addition, a pH buffer is preferably incorporated in the bleaching solution, and it is especially preferred to incorporate a dicarboxylic acid of low odor such as succinic acid, maleic acid, malonic acid, glutaric acid or adipic acid. It is also preferred to use common bleaching accelerators listed in JP-A-53-95630, RD No. 17129 and U.S. Pat. No. 3,893,858.

The bleaching solution is preferably replenished with 50 to 1000 mL, more preferably 80 to 500 mL, and much more preferably 100 to 300 mL, of a bleaching replenisher per $m^2$ of the lightsensitive material. Further, the bleaching solution is preferably aerated.

Compounds and processing conditions described on page 7, left lower column, line 10 to page 8, right lower column, line 19 of JP-A-4-125558 can be applied to a processing solution having fixing capability.

For enhancing the fixing velocity and preservability, it is especially preferred to incorporate compounds represented by the general formulae (I) and (II) of JP-A-6-301169 either individually or in combination in the processing solution having fixing capability. Further, the use of p-toluenesulfinic salts and sulfinic acids listed in JP-A-1-224762 is preferred from the viewpoint of enhancing the preservability.

Although the incorporation of an ammonium as a cation in the solution having bleaching capability or solution having fixing capability is preferred from the viewpoint of enhancing the bleach ability, it is preferred that the amount of ammonium be reduced or brought to nil from the viewpoint of minimizing environmental pollution.

Conducting jet agitation described in JP-A-1-309059 is especially preferred in the bleach, bleach-fix and fixation steps.

The amount of replenisher supplied in the bleach-fix or fixation step is in the range of 100 to 1000 mL, preferably 150 to 700 mL, and especially preferably 200 to 600 mL, per $m^2$ of the lightsensitive material.

Silver is preferably recovered by installing any of various silver recovering devices in an in-line or off-line mode in the bleach-fix or fixation step. In-line installation enables processing with the silver concentration of the solution lowered, so that the amount of replenisher can be reduced. It is also suitable to conduct an off-line silver recovery and recycle residual solution for use as a replenisher.

The bleach-fix and fixation steps can each be constructed by a plurality of processing tanks. Preferably, the tanks are provided with cascade piping and a multistage counterflow system is adopted. A 2-tank cascade structure is generally effective from the viewpoint of a balance with the size of the developing machine. The ratio of processing time in the former-stage tank to that in the latter-stage tank is preferably in the range of 0.5:1 to 1:0.5, more preferably 0.8:1 to 1:0.8.

From the viewpoint of enhancing the preservability, it is preferred that a chelating agent which is free without forming any metal complex be present in the bleach-fix and fixing solutions. Biodegradable chelating agents described in connection with the bleaching solution are preferably used as such a chelating agent.

Descriptions made on page 12, right lower column, line 6 to page 13, right lower column, line 16 of JP-A-4-125558 mentioned above can preferably be applied to water washing and stabilization steps. In particular, with respect to stabilizing solutions, the use of azolylmethylamines described in EP Nos. 504,609 and 519,190 and N-methylolazoles described in JP-A-4-362943 in place of formaldehyde, and the dimerization of magenta coupler into a surfactant solution not containing an image stabilizer such as formaldehyde are preferred from the viewpoint of protecting working environment.

Further, stabilizing solutions described in JP-A-6-289559 can preferably be used for reducing the adhesion of refuse to a magnetic recording layer applied to the lightsensitive material.

The replenishing amount of water washing and stabilizing solutions is preferably in the range of 80 to 1000 mL, more preferably 100 to 500 mL, and much more preferably 150 to 300 mL, per $m^2$ of the lightsensitive material from the viewpoint that water washing and stabilizing functions are ensured and that the amount of waste solution is reduced to contribute to environment protection. In the processing with the above replenishing amount, any of known mildewproofing agents such as thiabenzazole, 1,2-benzoisothiazolin-3-one and 5-chloro-2-methylisothiazolin-3-one and antibiotics such as gentamicin is preferably added, or water deionized by the use of, for example, an ion exchange resin is preferably used, for preventing the breeding of bacteria and mildew. The use of deionized water in combination with a mildewproofing agent and an antibiotic is more effective than individual uses.

With respect to the solution placed in the water washing or stabilizing solution tank, it is also preferred that the replenishing amount be reduced by conducting a reverse osmosis membrane treatment as described in JP-A's-3-46652, 3-53246, 3-55542, 3-121448 and 3-126030. A low-pressure reverse osmosis membrane is preferably used in the above treatment.

In the processing of the present invention, it is especially preferred that an evaporation correction of processing solution be carried out as disclosed in JIII (Japan Institute of Invention and Innovation) Journal of Technical Disclosure No. 94-4992. In particular, the method in which a correction is effected with the use of information on the temperature and humidity of developing machine installation environment in accordance with Formula 1 on page 2 thereof is preferred. Water for use in the evaporation correction is preferably harvested from the washing replenishing tank. In that instance, deionized water is preferably used as the washing replenishing water.

Processing agents set forth on page 3, right column, line 15 to page 4, left column, line 32 of the above journal of technical disclosure are preferably used in the present invention. Film processor described on page 3, right column, lines 22 to 28 thereof is preferably used as the developing machine in the processing of the present invention.

Specific examples of processing agents, automatic developing machines and evaporation correction schemes preferably employed in carrying out the present invention are described on page 5, right column, line 11 to page 7, right column, last line of the above journal of technical disclosure.

The processing agent for use in the present invention may be supplied in any form, for example, a liquid agent with the same concentration as in use or concentrated one, granules, powder, tablets, a paste or an emulsion. For example, a liquid agent stored in a container of low oxygen permeability is disclosed in JP-A-63-17453, vacuum packed powder or granules in JP-A's-4-19655 and 4-230748, granules containing a water soluble polymer in JP-A-4-221951, tablets in JP-A-51-61837 and JP-A-6-102628 and a paste processing agent in PCT National Publication 57-500485. Although any of these can be suitably used, from the viewpoint of easiness in use, it is preferred to employ a liquid prepared in the same concentration as in use in advance.

The container for storing the above processing agent is composed of, for example, any one or a mixture of polyethylene, polypropylene, polyvinyl chloride, polyethylene terephthalate and nylon. A selection is made in accordance with the required level of oxygen permeability. A material of low oxygen permeability is preferably used for storing an easily oxidized liquid such as a color developing solution, which is, for example, polyethylene terephthalate or a composite material of polyethylene and nylon. It is preferred that each of these materials be used in the container at a thickness of 500 to 1500 μm so that the oxygen permeability therethrough is 20 mL/m²·24 hrs·atm or less.

The processing solution for color reversal film to be employed in the present invention will be described below.

With respect to the processing for color reversal film, detailed descriptions are made in Public Technology No. 6 (Apr. 1, 1991) issued by Aztek, page 1, line 5 to page 10, line 5 and page 15, line 8 to page 24, line 2, any of which can be preferably applied thereto.

In the color reversal film processing, an image stabilizer is added to a conditioning bath or a final bath. Examples of suitable image stabilizers include formalin, formaldehyde sodium bisulfite and N-methylolazoles. Formaldehyde sodium bisulfite and N-methylolazoles are preferred from the viewpoint of working environment. Among the N-methylolazoles, N-methyloltriazole is especially preferred. The contents of descriptions on color developing solution, bleaching solution, fixing solution and washing water made in connection with the processing of color negative films are also preferably applicable to the processing of color reversal films.

Processing agent E-6 available from Eastman Kodak and processing agent CR-56 available from Fuji Photo Film Co., Ltd. can be mentioned as preferred color reversal film processing agents including the above feature.

The magnetic recording layer preferably used in the present invention will be described below.

The magnetic recording layer preferably used in the present invention is obtained by coating a support with a water-base or organic solvent coating liquid having magnetic material grains dispersed in a binder.

The magnetic material grains for use in the present invention can be composed of any of ferromagnetic iron oxides such as $\gamma Fe_2O_3$, Co coated $\gamma Fe_2O_3$, Co coated magnetite, Co containing magnetite, ferromagnetic chromium dioxide, ferromagnetic metals, ferromagnetic alloys, Ba ferrite of hexagonal system, Sr ferrite, Pb ferrite and Ca ferrite. Of these, Co coated ferromagnetic iron oxides such as Co coated $\gamma Fe_2O_3$ are preferred. The configuration thereof may be any of acicular, rice grain, spherical, cubic and plate shapes. The specific surface area is preferably at least 20 m²/g, more preferably at least 30 m²/g in terms of $S_{BET}$.

The saturation magnetization (σs) of the ferromagnetic material preferably ranges from $3.0 \times 10^4$ to $3.0 \times 10^5$ A/m, especially preferably from $4.0 \times 10^4$ to $2.5 \times 10^5$ A/m. The ferromagnetic material grains may have their surface treated with silica and/or alumina or an organic material. Further, the magnetic material grains may have their surface treated with a silane coupling agent or a titanium coupling agent as described in JP-A-6-161032. Still further, use can be made of magnetic material grains having their surface coated with an organic or inorganic material as described in JP-A's-4-259911 and 5-81652.

The binder for use in the magnetic material grains can be composed of any of natural polymers (e.g., cellulose derivatives and sugar derivatives), acid-, alkali- or bio-degradable polymers, reactive resins, radiation curable resins, thermosetting resins and thermoplastic resins listed in JP-A-4-219569 and mixtures thereof. The Tg of each of the above resins ranges from −40 to 300° C. and the weight average molecular weight thereof ranges from 2 thousand to 1 million. For example, vinyl copolymers, cellulose derivatives such as cellulose diacetate, cellulose triacetate, cellulose acetate propionate, cellulose acetate butyrate and cellulose tripropionate, acrylic resins and polyvinylacetal resins can be mentioned as suitable binder resins. Gelatin is also a suitable binder resin. Of these, cellulose di(tri)acetate is especially preferred. The binder can be cured by adding an epoxy, aziridine or isocyanate crosslinking agent. Suitable isocyanate crosslinking agents include, for example, isocyanates such as tolylene diisocyanate, 4,4'-diphenylmethane diisocyanate, hexamethylene diisocyanate and xylylene diisocyanate, reaction products of these isocyanates and polyalcohols (e.g., reaction product of 3 mol of tolylene diisocyanate and 1 mol of trimethylolpropane), and polyisocyanates produced by condensation of these isocyanates, as described in, for example, JP-A-6-59357.

The method of dispersing the magnetic material in the above binder preferably comprises using a kneader, a pin type mill and an annular type mill either individually or in combination as described in JP-A-6-35092. Dispersants listed in JP-A-5-088283 and other common dispersants can be used. The thickness of the magnetic recording layer ranges from 0.1 to 10 μm, preferably 0.2 to 5 μm, and more preferably from 0.3 to 3 μm. The weight ratio of magnetic material grains to binder is preferably in the range of 0.5:100 to 60:100, more preferably 1:100 to 30:100. The coating amount of magnetic material grains ranges from 0.005 to 3 g/m², preferably from 0.01 to 2 g/m², and more preferably from 0.02 to 0.5 g/m². The transmission yellow density of the magnetic recording layer is preferably in the range of 0.01 to 0.50, more preferably 0.03 to 0.20, and most preferably 0.04 to 0.15.

The magnetic recording layer can be applied to the back of a photographic support in its entirety or in striped pattern by coating or printing. The magnetic recording layer can be applied by the use of, for example, an air doctor, a blade, an air knife, a squeeze, an immersion, reverse rolls, transfer rolls, a gravure, a kiss, a cast, a spray, a dip, a bar or an extrusion. Coating liquids set forth in JP-A-5-341436 are preferably used.

The magnetic recording layer may also be provided with, for example, lubricity enhancing, curl regulating, antistatic, sticking preventive and head polishing functions, or other functional layers may be disposed to impart these functions. An abrasive of grains whose at least one member is nonspherical inorganic grains having a Mohs hardness of at least 5 is preferred. The nonspherical inorganic grains are preferably composed of fine grains of any of oxides such as aluminum oxide, chromium oxide, silicon dioxide, and titanium dioxide; carbides such as silicon carbide and titanium carbide; and diamond. These abrasives may have their surface treated with a silane coupling agent or a titanium coupling agent. The above grains may be added to the magnetic recording layer, or the magnetic recording layer may be overcoated with the grains (e.g., as a protective layer or a lubricant layer). The binder which is used in this instance can be the same as mentioned above and, preferably, the same as the that of the magnetic recording layer. The lightsensitive material having the magnetic recording layer is described in U.S. Pat. Nos. 5,336,589, 5,250,404, 5,229,259 and 5,215,874 and EP No. 466,130.

The polyester support preferably used in the present invention will be described below. Particulars thereof together with the below mentioned lightsensitive material, processing, cartridge and working examples are specified in JIII Journal of Technical Disclosure No. 94-6023 (issued by Japan Institute of Invention and Innovation on Mar. 15, 1994). The polyester for use in the present invention is prepared from a diol and an aromatic dicarboxylic acid as essential components. Examples of suitable aromatic dicarboxylic acids include 2,6-, 1,5-, 1,4- and 2,7-naphthalenedicarboxylic acids, terephthalic acid, isophthalic acid and phthalic acid, and examples of suitable diols include diethylene glycol, triethylene glycol, cyclohexanedimethanol, bisphenol A and other bisphenols. The resultant polymers include homopolymers such as polyethylene terephthalate, polyethylene naphthalate and polycyclohexanedimethanol terephthalate. Polyesters containing 2,6-naphthalenedicarboxylic acid in an amount of 50 to 100 mol. % are especially preferred. Polyethylene 2,6-naphthalate is most preferred.

The average molecular weight thereof ranges from approximately 5,000 to 200,000. The Tg of the polyester for use in the present invention is at least 50° C., preferably at least 90° C.

The polyester support is subjected to heat treatment at a temperature of from 40° C. to less than Tg, preferably from Tg minus 20° C. to less than Tg, in order to suppress curling. The heat treatment may be conducted at a temperature held constant within the above temperature range or may be conducted while cooling. The period of heat treatment ranges from 0.1 to 1500 hr, preferably 0.5 to 200 hr. The support may be heat treated either in the form of a roll or while being carried in the form of a web. The surface form of the support may be improved by rendering the surface irregular (e.g., coating with conductive inorganic fine grains of $SnO_2$, $Sb_2O_5$, etc.). Moreover, a scheme is desired such that edges of the support are knurled so as to render only the edges slightly high, thereby preventing photographing of core sections. The above heat treatment may be carried out in any of stages after support film formation, after surface treatment, after back layer application (e.g., application of an antistatic agent or a lubricant) and after undercoating application. The heat treatment is preferably performed after antistatic agent application.

An ultraviolet absorber may be milled into the polyester. Light piping can be prevented by milling, into the polyester, dyes and pigments commercially available as polyester additives, such as Diaresin produced by Mitsubishi Chemical Industries, Ltd. and Kayaset produced by NIPPON KAYAKU CO., LTD.

In the present invention, a surface treatment is preferably conducted for bonding a support and a lightsensitive material constituting layer to each other. The surface treatment is, for example, a surface activating treatment such as chemical treatment, mechanical treatment, corona discharge treatment, flame treatment, ultraviolet treatment, high frequency treatment, glow discharge treatment, active plasma treatment, laser treatment, mixed acid treatment or ozone oxidation treatment. Of these surface treatments, ultraviolet irradiation treatment, flame treatment, corona treatment and glow treatment are preferred.

The subbing method will be described below. The substratum may be composed of either a single layer or at least two layers. As the binder for the substratum, there can be mentioned not only copolymers prepared from monomers, as starting materials, selected from vinyl chloride, vinylidene chloride, butadiene, methacrylic acid, acrylic acid, itaconic acid and maleic anhydride but also polyethyleneimine, an epoxy resin, a grafted gelatin, nitrocellulose and gelatin. Resorcin or p-chlorophenol is used as a support swelling compound. A gelatin hardener such as a chromium salt (e.g., chrome alum), an aldehyde (e.g., formaldehyde or glutaraldehyde), an isocyanate, an active halogen compound (e.g., 2,4-dichloro-6-hydroxy-S-triazine), an epichlorohydrin resin or an active vinyl sulfone compound can be used in the subbing layer. Also, $SiO_2$, $TiO_2$, inorganic fine grains or polymethyl methacrylate copolymer fine grains (0.01 to 10 $\mu$m) may be incorporated therein as a matting agent.

Further, an antistatic agent is preferably used in the present invention. Examples of suitable antistatic agents include carboxylic acids and carboxylic salts, sulfonic acid salt containing polymers, cationic polymers and ionic surfactant compounds.

Most preferred as the antistatic agent are fine grains of at least one crystalline metal oxide selected from among ZnO, $TiO_2$, $SnO_2$, $Al_2O_3$, $In_2O_3$, $SiO_2$, MgO, BaO, $MoO_3$ and $V_2O_5$ having a volume resistivity of $10^7$ $\Omega$·cm or less, preferably $10^5$ $\Omega$·cm or less, and having a grain size of 0.001 to 1.0 $\mu$m or a composite oxide thereof (Sb, P, B, In, S, Si, C, etc.) and fine grains of sol form metal oxides or composite oxides thereof.

The content thereof in the lightsensitive material is preferably in the range of 5 to 500 mg/m$^2$, more preferably 10 to 350 mg/m$^2$. The ratio of amount of conductive crystalline oxide or composite oxide thereof to binder is preferably in the range of 1/300 to 100/1, more preferably 1/100 to 100/5.

It is preferred that the lightsensitive material of the present invention have lubricity. The lubricant containing layer is preferably provided on both the lightsensitive layer side and the back side. Preferred lubricity ranges from 0.25 to 0.01 in terms of dynamic friction coefficient. The measured lubricity is a value obtained by conducting a carriage on a stainless steel ball of 5 mm in diameter at 60 cm/min (25° C., 60% RH). In this evaluation, value of approximately the same level is obtained even when the opposite material is replaced by the lightsensitive layer surface.

The lubricant which can be used in the present invention is, for example, a polyorganosiloxane, a higher fatty acid amide, a higher fatty acid metal salt or an ester of higher fatty acid and higher alcohol. Examples of suitable polyorganosiloxanes include polydimethylsiloxane, polydiethylsiloxane, polystyrylmethylsiloxane and polymethylphenylsiloxane. The lubricant is preferably added to the back layer or the outermost layer of the emulsion layer. Especially, polydimethylsiloxane and an ester having a long chain alkyl group are preferred.

A matting agent is preferably used in the lightsensitive material of the present invention. Although the matting agent may be used on the emulsion side or the back side indiscriminately, it is especially preferred that the matting agent be added to the outermost layer of the emulsion side. The matting agent may be soluble in the processing solution or insoluble in the processing solution, and it is preferred to use the soluble and insoluble matting agents in combination. For example, polymethyl methacrylate, poly(methyl methacrylate/methacrylic acid=9/1 or 5/5 in molar ratio) and polystyrene grains are preferred. The grain size thereof preferably ranges from 0.8 to 10 μm. Narrow grain size distribution thereof is preferred, and it is desired that at least 90% of the whole number of grains be included in the range of 0.9 to 1.1 times the average grain size. Moreover, for enhancing the mat properties, it is preferred that fine grains of 0.8 μm or less be simultaneously added, which include, for example, fine grains of polymethyl methacrylate (0.2 μm), poly(methyl methacrylate/methacrylic acid 9/1 in molar ratio, 0.3 μm), polystyrene (0.25 μm) and colloidal silica (0.03 μm).

The film patrone employed in the present invention will be described below. The main material composing the patrone for use in the present invention may be a metal or a synthetic plastic.

Examples of preferable plastic materials include polystyrene, polyethylene, polypropylene and polyphenyl ether. The patrone for use in the present invention may contain various types of antistatic agents and can preferably contain, for example, carbon black, metal oxide grains, nonionic, anionic, cationic or betaine type surfactants and polymers. Such an antistatic patrone is described in JP-A's-1-312537 and 1-312538. The resistance thereof at 25° C. in 25% RH is preferably $10^{12}$ Ω or less. The plastic patrone is generally molded from a plastic having carbon black or a pigment milled thereinto for imparting light shielding properties. The patrone size may be the same as the current size 135, or for miniaturization of cameras, it is advantageous to decrease the diameter of the 25 mm cartridge of the current size 135 to 22 mm or less. The volume of the case of the patrone is preferably 30 cm$^3$ or less, more preferably 25 cm$^3$ or less. The weight of the plastic used in each patrone or patrone case preferably ranges from 5 to 15 g.

The patrone for use in the present invention may be one capable of feeding a film out by rotating a spool. Further, the patrone may be so structured that a film front edge is accommodated in the main frame of the patrone and that the film front edge is fed from a port part of the patrone to the outside by rotating a spool shaft in a film feeding out direction. These are disclosed in U.S. Pat. Nos. 4,834,306 and 5,226,613. The photographic film for use in the present invention may be a generally so termed raw stock having not yet been developed or a developed photographic film. The raw stock and the developed photographic film may be accommodated in the same new patrone or in different patrones.

The color photographic lightsensitive material of the present invention is suitably used as a negative film for Advanced Photo System (hereinafter referred to as "AP system"). It is, for example, one obtained by working the film into AP system format and accommodating the same in a special purpose cartridge, such as NEXIA A, NEXIA F or NEXIA H (sequentially, ISO 200/100/400) produced by Fuji Photo Film Co., Ltd. (hereinafter referred to as "Fuji Film"). This cartridge film for AP system is charged in a camera for AP system such as Epion series, e.g., Epion 300Z, produced by Fuji Film and put to practical use. Moreover, the color photographic lightsensitive material of the present invention is suitable to a lens equipped film, such as Fuji Color Utsurundesu Super Slim (Quick Snap) produced by Fuji Film.

The thus photographed film is printed through the following steps in a minilabo system:

(1) acceptance (receiving an exposed cartridge film from a customer),
(2) detaching (transferring the film from the above cartridge to an intermediate cartridge for development),
(3) film development,
(4) re-attaching (returning the developed negative film to the original cartridge),
(5) printing (continuous automatic printing of C/H/P three type print and index print on color paper (preferably, Super FA8 produced by Fuji Film)), and
(6) collation and delivery (collating the cartridge and index print with ID number and delivering the same with prints).

The above system is preferably Fuji Film Minilabo Champion Super FA-298/FA-278/FA-258/FA-238 or Fuji Film Digital Labo System Frontier. Film processor of the Minilabo Champion is, for example, FP922AL/FP562B/FP562B, AL/FP362B/FP362B, AL, and recommended processing chemical is Fuji Color Just It CN-16L or CN-16Q. Printer processor is, for example, PP3008AR/PP3008A/PP1828AR/PP1828A/PP1258AR/PP1258A/PP72 8AR/PP728A, and recommended processing chemical thereof is Fuji Color Just It CP-47L or CP-40FAII.

In the Frontier System, use is made of scanner & image processor SP-1000 and laser printer & paper processor LP-1000P or Laser Printer LP-1000W. Fuji Film DT200/DT100 and AT200/AT100 are preferably used as detacher in the detaching step and as re-attacher in the reattaching step, respectively.

The AP system can be enjoyed by photo joy system whose center unit is Fuji Film digital image work station Aladdin 1000. For example, developed AP system cartridge film is directly charged in Aladdin 1000, or negative film, positive film or print image information is inputted with the use of 35 mm film scanner FE-550 or flat head scanner PE-550 therein, and obtained digital image data can easily be worked and edited. The resultant data can be outputted as prints by current labo equipment, for example, by means of digital color printer NC-550AL based on photofixing type thermal color printing system or Pictrography 3000 based on laser exposure thermal development transfer system or through a film recorder. Moreover, Aladdin 1000 is capable of directly outputting digital information to a floppy disk or Zip disk or outputting it through a CD writer to CD-R.

On the other hand, at home, photographs can be enjoyed on TV only by charging the developed AP system cartridge film in photoplayer AP-1 manufactured by Fuji Film. Charging it in Photoscanner AS-1 manufactured by Fuji Film enables continuously feeding image information into a personal computer at a high speed. Further, Photovision FV-10/FV-5 manufactured by Fuji Film can be utilized for inputting a film, print or three-dimensional object in a personal computer. Still further, image information recorded on a floppy disk, Zip disk, CD-R or a hard disk can be enjoyed by conducting various workings on the personal computer by the use of Fuji Film Application Soft Photofactory. Digital color printer NC-2/NC-2D based on photofixing type thermal color printing system, manufactured by Fuji Film, is suitable for outputting high-quality prints from a personal computer.

Fuji Color Pocket Album AP-5 Pop L, AP-1 Pop L, AP-1 Pop KG or Cartridge File 16 is preferably employed for storing the developed AP system cartridge film.

EXAMPLE

The present invention will now be specifically explained by Examples, but the present invention is not limited to them.

Comparative Example-1

(Preparation of Sample 101)

(1) Preparation of Triacetylcellulose Film

Triacetylcellulose was dissolved (13% by weight) by a common solution casting process in dichloromethane/methanol=92/8 (weight ratio), and triphenyl phosphate and biphenyldiphenyl phosphate in a weight ratio of 2:1, which are plasticizers, were added to the resultant solution so that the total amount of the plasticizers was 14% to the triacetylcellulose. Then, a triacetylcellulose film was made by a band process. The thickness of the support after drying was 97 μm.

(2) Components of Undercoat Layer

The two surfaces of the triacetylcellulose film were subjected to undercoating treatment. Numbers represent weight contained per liter of an undercoat solution.

The two surfaces of the triacetylcellulose film were subjected to corona discharge treatment before undercoating treatment.

| | |
|---|---|
| Gelatin | 10.0 g |
| Salicylic acid | 0.5 g |
| Glycerin | 4.0 g |
| Acetone | 700 mL |
| Methanol | 200 mL |
| Dichloromethane | 80 mL |
| Formaldehyde | 0.1 mg |
| Water to make | 1.0 L |

(3) Coating of Back Layers

One surface of the undercoated support was coated with the following back layers.

| 1st layer | |
|---|---|
| Binder: acid-processed gelatin (isoelectric point: 9.0) | 1.00 g |
| Polymeric latex: P-2 (average grain size: 0.1 μm) | 0.13 g |
| Polymeric latex: P-3 (average grain size: 0.2 μm) | 0.23 g |
| Ultraviolet absorbent U-1 | 0.030 g |
| Ultraviolet absorbent U-3 | 0.010 g |
| Ultraviolet absorbent U-4 | 0.020 g |
| High-boiling organic solvent Oil-2 | 0.030 g |
| Surfactant W-3 | 0.010 g |
| Surfactant W-6 | 3.0 mg |
| 2nd layer | |
| Binder: acid-processed gelatin (isoelectric point: 9.0) | 3.10 g |
| Polymeric latex: P-2 (average grain size: 0.2 μm) | 0.11 g |
| Ultraviolet absorbent U-1 | 0.030 g |
| Ultraviolet absorbent U-3 | 0.010 g |
| Ultraviolet absorbent U-4 | 0.020 g |
| High-boiling organic solvent Oil-2 | 0.030 g |
| Surfactant W-3 | 0.010 g |
| Surfactant W-6 | 3.0 mg |
| Dye D-2 | 0.10 g |
| Dye D-10 | 0.12 g |
| Potassium sulfate | 0.25 g |
| Calcium chloride | 0.5 mg |
| Sodium hydroxide | 0.03 g |
| 3rd layer | |
| Binder: acid-processed gelatin (isoelectric point: 9.0) | 3.30 g |
| Surfactant W-3 | 0.020 g |
| Potassium sulfate | 0.30 g |
| Sodium hydroxide | 0.03 g |
| 4th layer | |
| Binder: lime-processed gelatin (isoelectric point: 5.4) | 1.15 g |
| 1:9 copolymer of methacrylic acid and methylmethacrylate (average grain size: 2.0 μm) | 0.040 g |
| 6:4 copolymer of methacrylic acid and methylmethacrylate (average grain size: 2.0 μm) | 0.030 g |
| Surfactant W-3 | 0.060 g |
| Surfactant W-2 | 7.0 mg |
| Hardener H-1 | 0.23 g |

(4) Coating of Photosensitive Emulsion Layers

Sample 101 was made by coating photosensitive emulsion layers presented below on the side opposite, against the support, to the side having the back layers. Numbers represent addition amounts per $m^2$ of the coating surface. Note that the effects of added compounds are not restricted to the described purposes.

| 1st layer: Antihalation layer | | |
|---|---|---|
| Black colloidal silver | | 0.25 g |
| Gelatin | | 2.40 g |
| Ultraviolet absorbent U-1 | | 0.15 g |
| Ultraviolet absorbent U-3 | | 0.15 g |
| Ultraviolet absorbent U-4 | | 0.10 g |
| Ultraviolet absorbent U-5 | | 0.10 g |
| High-boiling organic solvent Oil-1 | | 0.10 g |
| High-boiling organic solvent Oil-2 | | 0.10 g |
| High-boiling organic solvent Oil-5 | | 0.010 g |
| Dye D-4 | | 1.0 mg |
| Dye D-8 | | 2.5 mg |
| Fine crystal solid dispersion of dye E-1 | | 0.05 g |
| 2nd layer: Interlayer | | |
| Gelatin | | 0.50 g |
| Compound Cpd-A | | 0.2 mg |
| Compound Cpd-K | | 3.0 mg |
| Compound Cpd-M | | 0.030 g |
| Ultraviolet absorbent U-6 | | 6.0 mg |
| High-boiling organic solvent Oil-3 | | 0.010 g |
| High-boiling organic solvent Oil-4 | | 0.010 g |
| High-boiling organic solvent Oil-7 | | 2.0 mg |
| Dye D-7 | | 4.0 mg |
| 3rd layer: Interlayer | | |
| Yellow colloidal silver | | 0.020 g |
| Silver iodobromide emulsion whose surface and interior are previously fogged (cubic, average silver iodide content: 1 mol %, equivalent sphere average grain size: 0.06 μm) | silver | 0.010 g |
| Gelatin | | 0.60 g |
| Compound Cpd-D | | 0.020 g |
| High-boiling organic solvent Oil-3 | | 0.010 g |
| High-boiling organic solvent Oil-8 | | 0.010 g |
| 4th layer: Low-speed red-sensitive emulsion layer | | |
| Emulsion A | silver | 0.10 g |
| Emulsion B | silver | 0.15 g |
| Emulsion C | silver | 0.15 g |
| Gelatin | | 0.80 g |
| Coupler C-1 | | 0.15 g |
| Coupler C-2 | | 7.0 mg |
| Coupler C-10 | | 3.0 mg |
| Coupler C-11 | | 2.0 mg |
| Ultraviolet absorbent U-3 | | 0.010 g |
| Compound Cpd-I | | 0.020 g |
| Compound Cpd-D | | 3.0 mg |
| Compound Cpd-J | | 2.0 mg |
| High-boiling organic solvent Oil-10 | | 0.030 g |
| Additive P-1 | | 5.0 mg |

-continued

5th layer: Medium-speed red-sensitive emulsion layer

| | | |
|---|---|---|
| Emulsion C | silver | 0.15 g |
| Emulsion D | silver | 0.15 g |
| Gelatin | | 0.70 g |
| Coupler C-1 | | 0.15 g |
| Coupler C-2 | | 7.0 mg |
| Coupler C-10 | | 3.0 mg |
| Compound Cpd-D | | 3.0 mg |
| Ultraviolet absorbent U-3 | | 0.010 g |
| High-boiling organic solvent Oil-10 | | 0.030 g |
| Additive P-1 | | 7.0 mg |

6th layer: High-speed red-sensitive emulsion layer

| | | |
|---|---|---|
| Emulsion E | silver | 0.15 g |
| Emulsion F | silver | 0.20 g |
| Gelatin | | 1.50 g |
| Coupler C-1 | | 0.60 g |
| Coupler C-2 | | 0.015 g |
| Coupler C-3 | | 0.030 g |
| Coupler C-10 | | 5.0 mg |
| Ultraviolet absorbent U-1 | | 0.010 g |
| Ultraviolet absorbent U-2 | | 0.010 g |
| High-boiling organic solvent Oil-6 | | 0.030 g |
| High-boiling organic solvent Oil-9 | | 0.020 g |
| High-boiling organic solvent Oil-10 | | 0.050 g |
| Compound Cpd-D | | 5.0 mg |
| Compound Cpd-K | | 1.0 mg |
| Compound Cpd-F | | 0.030 g |
| Compound Cpd-L | | 1.0 mg |
| Additive P-1 | | 0.010 g |
| Additive P-4 | | 0.030 g |

7th layer: Interlayer

| | | |
|---|---|---|
| Gelatin | | 0.70 g |
| Additive P-2 | | 0.10 g |
| Dye D-5 | | 0.020 g |
| Dye D-9 | | 6.0 mg |
| Compound Cpd-I | | 0.010 g |
| Compound Cpd-M | | 0.040 g |
| Compound Cpd-O | | 3.0 mg |
| Compound Cpd-P | | 5.0 mg |
| High-boiling organic solvent Oil-6 | | 0.050 g |

8th layer: Interlayer

| | | |
|---|---|---|
| Yellow colloidal silver | silver | 0.020 g |
| Gelatin | | 1.00 g |
| Additive P-2 | | 0.05 g |
| Ultraviolet absorbent U-1 | | 0.010 g |
| Ultraviolet absorment U-3 | | 0.010 g |
| Compound Cpd-A | | 0.050 g |
| Compound Cpd-D | | 0.030 g |
| Compound Cpd-M | | 0.050 g |
| High-boiling organic solvent Oil-3 | | 0.010 g |
| High-boiling organic solvent Oil-6 | | 0.050 g |

9th layer: Low-speed green-sensitive emulsion layer

| | | |
|---|---|---|
| Emulsion G | silver | 0.25 g |
| Emulsion H | silver | 0.30 g |
| Emulsion I | silver | 0.25 g |
| Gelatin | | 1.30 g |
| Coupler C-4 | | 0.20 g |
| Coupler C-5 | | 0.050 g |
| Coupler C-6 | | 0.020 g |
| Compound Cpd-A | | 5.0 mg |
| Compound Cpd-B | | 0.030 g |
| Compound Cpd-D | | 5.0 mg |
| Compound Cpd-G | | 2.5 mg |
| Compound Cpd-F | | 0.010 g |
| Compound Cpd-K | | 2.0 mg |
| Ultraviolet absorbent U-6 | | 5.0 mg |
| High-boiling organic solvent Oil-2 | | 0.25 g |
| Additive P-1 | | 5.0 mg |

10th layer: Medium-speed green-sensitive emulsion layer

| | | |
|---|---|---|
| Emulsion I | silver | 0.30 g |
| Emulsion J | silver | 0.30 g |
| Silver bromide emulsion whose interior is fogged (cubic, equivalent sphere average grain size: 0.11 μm) | silver | 3.0 mg |
| Gelatin | | 0.70 g |
| Coupler C-4 | | 0.25 g |
| Coupler C-5 | | 0.050 g |
| Coupler C-6 | | 0.020 g |
| Compound Cpd-A | | 5.0 mg |
| Compound Cpd-B | | 0.030 g |
| Compound Cpd-F | | 0.010 g |
| Compound Cpd-G | | 2.0 mg |
| High-boiling organic solvent Oil-2 | | 0.20 g |
| High-boiling organic solvent Oil-9 | | 0.050 g |

11th layer: High-speed green-sensitive emulsion layer

| | | |
|---|---|---|
| Emulsion K | silver | 0.40 g |
| Gelatin | | 0.80 g |
| Coupler C-4 | | 0.30 g |
| Coupler C-5 | | 0.080 g |
| Coupler C-7 | | 0.050 g |
| Compound Cpd-A | | 5.0 mg |
| Compound Cpd-B | | 0.030 g |
| Compound Cpd-F | | 0.010 g |
| High-boiling organic solvent Oil-2 | | 0.20 g |
| High-boiling organic solvent Oil-9 | | 0.050 g |

12th layer: Yellow filter layer

| | | |
|---|---|---|
| Yellow Colloidal Silver | silver | 0.010 g |
| Gelatin | | 1.0 g |
| Compound Cpd-C | | 0.010 g |
| Compound Cpd-M | | 0.10 g |
| High-boiling organic solvent Oil-1 | | 0.020 g |
| High-boiling organic solvent Oil-6 | | 0.10 g |
| Fine crystal solid dispersion of dye E-2 | | 0.20 g |

13th layer: Interlayer

| | | |
|---|---|---|
| Gelatin | | 0.40 g |
| Compound Cpd-Q | | 0.20 g |
| Dye D-6 | | 3.0 mg |

14th layer: Low-speed blue-sensitive emulsion layer

| | | |
|---|---|---|
| Emulsion L | silver | 0.15 g |
| Emulsion M | silver | 0.20 g |
| Emulsion N | silver | 0.10 g |
| Gelatin | | 0.80 g |
| Coupler Cp-1 | | 0.22 g |
| Compound Cpd-B | | 0.10 g |
| Compound Cpd-I | | 8.0 mg |
| Compound Cpd-K | | 1.0 mg |
| Compound Cpd-M | | 0.010 g |
| Ultraviolet absorbent U-6 | | 0.010 g |
| High-boiling organic solvent Oil-2 | | 0.010 g |

15th layer: Medium-speed blue-sensitive emulsion layer

| | | |
|---|---|---|
| Emulsion N | silver | 0.20 g |
| Emulsion O | silver | 0.20 g |
| Silver bromide emulsion whose interior is fogged (cubic, equivalent sphere average grain size: 0.11 μm) | silver | 3.0 mg |
| Gelatin | | 0.80 g |
| Coupler Cp-1 | | 0.20 g |
| Compound Cpd-B | | 0.10 g |
| Compound Cpd-E | | 0.030 g |
| Compound Cpd-N | | 2.0 mg |
| High-boiling organic solvent Oil-2 | | 0.010 g |

16th layer: High-speed blue-sensitive emulsion layer

| | | |
|---|---|---|
| Emulsion P | silver | 0.20 g |
| Emulsion Q | silver | 0.25 g |
| Gelatin | | 2.00 g |
| Coupler C-3 | | 5.0 mg |
| Coupler Cp-1 | | 0.77 g |
| High-boiling organic solvent Oil-2 | | 0.10 g |
| High-boiling organic solvent Oil-3 | | 0.020 g |
| Ultraviolet absorbent U-6 | | 0.10 g |
| Compound Cpd-B | | 0.20 g |
| Compound Cpd-N | | 5.0 mg |

17th layer: 1st protective layer

| | | |
|---|---|---|
| Gelatin | | 1.00 g |

-continued

| | |
|---|---|
| Ultraviolet absorbent U-1 | 0.15 g |
| Ultraviolet absorbent U-2 | 0.050 g |
| Ultraviolet absorbent U-5 | 0.20 g |
| Compound Cpd-O | 5.0 mg |
| Compound Cpd-A | 0.030 g |
| Compound Cpd-H | 0.20 g |
| Dye D-1 | 8.0 mg |
| Dye D-2 | 0.010 g |
| Dye D-3 | 0.010 g |
| High-boiling organic solvent Oil-3 | 0.10 g |
| 18th layer: 2nd protective layer | |
| Colloidal silver  silver | 2.5 mg |
| Fine grain silver iodobromide emulsion (average grain diameter 0.06 μm, AgI content: 1 mol %)  silver | 0.10 g |
| Gelatin | 0.80 g |
| Ultraviolet absorbent U-1 | 0.030 g |
| Ultraviolet absorbent U-6 | 0.030 g |
| High-boiling organic solvent Oil-3 | 0.010 g |
| 19th layer: 3rd protective layer | |
| Gelatin | 1.00 g |

-continued

| | |
|---|---|
| Polymethylmethacrylate (average grain size 1.5 μm) | 0.10 g |
| 6:4 copolymer of methylmethacrylate and methacrylic acid (average grain size 1.5 μm) | 0.15 g |
| Silicone oil SO-1 | 0.20 g |
| Surfactant W-1 | 3.0 mg |
| Surfactant W-2 | 8.0 mg |
| Surfactant W-3 | 0.040 g |
| Surfactant W-7 | 0.015 g |

In addition to the above compositions, additives F-1 to F-9 were added to all emulsion layers. Also, a gelatin hardener H-1 and surfactants W-3, W-4, W-5, and W-6 for coating and emulsification were added to each layer.

Furthermore, phenol, 1,2-benzisothiazoline-3-one, 2-phenoxyethanol, phenethyl alcohol, and butyl p-benzoate were added as antiseptic and mildewproofing agents.

TABLE 1

Silver idobromide emulsions used in Sample 101

| Emulsion | Characteristics | Av. ESD (μm) | COV (%) | Av. AgI content (mol %) | Structure in halide composition of silver halide grains | AgI content at grain surface (mol %) | Other characteristics (1) | (2) | (3) | (4) | (5) |
|---|---|---|---|---|---|---|---|---|---|---|---|
| A | Monodispersed tetradecahedral grains | 0.24 | 9 | 3.5 | Triple structure | 1.5 | | ○ | | | |
| B | Monodispersed (111) tabular grains Av. aspect ratio 2.0 | 0.25 | 10 | 3.5 | Quadruple structure | 1.5 | ○ | | ○ | ○ | ○ |
| C | Monodispersed (111) tabular grains Av. aspect ratio 2.0 | 0.30 | 19 | 3.0 | Triple structure | 0.1 | ○ | ○ | | ○ | ○ |
| D | Monodispersed (111) tabular grains Av. aspect ratio 3.0 | 0.35 | 21 | 4.8 | Triple structure | 2.0 | ○ | ○ | | ○ | ○ |
| E | Monodispersed (111) tabular grains Av. aspect ratio 3.0 | 0.40 | 10 | 2.0 | Quadruple structure | 1.5 | | ○ | | | |
| F | Monodispersed (111) tabular grains Av. aspect ratio 4.5 | 0.55 | 12 | 1.6 | Triple structure | 0.6 | ○ | ○ | | | ○ |
| G | Monodispersed cubic grains | 0.15 | 9 | 3.5 | Quadruple structure | 2.0 | | | ○ | | |
| H | Monodispersed cubic grains | 0.24 | 12 | 4.9 | Quadruple structure | 0.1 | ○ | ○ | ○ | | |
| I | Monodispersed (111) tabular grains Av. aspect ratio 4.0 | 0.30 | 12 | 3.5 | Quintuple structure | 4.5 | ○ | ○ | | ○ | ○ |
| J | Monodispersed (111) tabular grains Av. aspect ratio 5.0 | 0.45 | 21 | 3.0 | Quadruple structure | 0.2 | ○ | ○ | | ○ | ○ |
| K | Monodispersed (111) tabular grains Av. aspect ratio 5.5 | 0.60 | 13 | 2.7 | Triple structure | 1.3 | ○ | ○ | | | ○ |
| L | Monodispersed tetradecahedral grains | 0.31 | 9 | 7.5 | Triple structure | 7.0 | | | | ○ | ○ |
| M | Monodispersed tetradecahedral grains | 0.31 | 9 | 7.5 | Triple structure | 5.0 | ○ | ○ | | ○ | ○ |
| N | Monodispersed (111) tabular grains Av. aspect ratio 3.0 | 0.33 | 13 | 2.1 | Quadruple structure | 4.0 | ○ | ○ | ○ | | |

TABLE 1-continued

Silver idobromide emulsions used in Sample 101

| Emulsion | Characteristics | Av. ESD (μm) | COV (%) | Av. AgI content (mol %) | Structure in halide composition of silver halide grains | AgI content at grain surface (mol %) | Other characteristics (1) | (2) | (3) | (4) | (5) |
|---|---|---|---|---|---|---|---|---|---|---|---|
| O | Monodispersed (111) tabular grains Av. aspect ratio 3.0 | 0.43 | 9 | 2.5 | Quadruple structure | 1.0 | ○ | ○ |  | ○ | ○ |
| P | Monodispersed (111) tabular grains Av. aspect ratio 6.0 | 0.75 | 21 | 2.8 | Triple structure | 0.5 | ○ | ○ |  |  | ○ |
| Q | Monodispersed (111) tabular grains Av. aspect ratio 6.0 | 0.90 | 8 | 1.0 | Quadruple structure | 0.5 | ○ | ○ |  |  | ○ |
| R | Monodispersed (111) tabular grains Av. aspect ratio 7.0 | 0.70 | 18 | 6.0 | Triple structure | 0.5 | ○ | ○ |  |  | ○ |

Av. ESD = Equivalent-sphere average grain size; COV = Coefficient of variation
(Other characteristics)
The mark "○" means each of the conditions set forth below is satisfied.
(1) A reduction sensitizer was added during grain formation;
(2) A selenium sensitizer was used as an after-ripening agent
(3) A rhodium salt was added during grain formation.
(4) A shell was provided subsequent to after-ripening by using silver nitrate in an amount of 10%, in terms of silver molar ratio, of the emulsion grains at that time, together with the equimolar amount of potassium bromide
(5) The presence of dislocation lines in an average number of ten or more per grain was observed by a transmission electron microscope.
Note that all the lightsensitive emulsion were after-ripped by the use of sodium thiosulfate, sodium thiocyanate, and sodium aurichloride.
Note, also, a iridium salt was appropriately added during grain formation.
Note, also, that chemically-modified gelatin whose amino groups were partially converted to phthalic acid amide, was added to emulsions B, C, E, H, J, N, and Q.

TABLE 2

Spectral sensitization of Emulsions A to E

| Emulsion | Spectral sensitizer added | Addition amount per mol of silver halide (g) | Timing of the addition of the spectral sensitizer |
|---|---|---|---|
| A | S-1 | 0.01 | Subsequent to after-ripening |
|  | S-2 | 0.35 | Prior to after-ripening |
|  | S-3 | 0.02 | Prior to after-ripening |
|  | S-8 | 0.03 | Prior to after-ripening |
|  | S-13 | 0.015 | Prior to after-ripening |
|  | S-14 | 0.01 | Prior to after-ripening |
| B | S-2 | 0.35 | Prior to after-ripening |
|  | S-3 | 0.02 | Prior to after-ripening |
|  | S-8 | 0.03 | Prior to after-ripening |
|  | S-13 | 0.015 | Prior to after-ripening |
|  | S-14 | 0.01 | Prior to after-ripening |
| C | S-2 | 0.45 | Prior to after-ripening |
|  | S-8 | 0.04 | Prior to after-ripening |
|  | S-13 | 0.02 | Prior to after-ripening |
| D | S-2 | 0.5 | Subsequent to after-ripening |
|  | S-3 | 0.05 | Subsequent to after-ripening |
|  | S-8 | 0.05 | Prior to after-ripening |
|  | S-13 | 0.015 | Prior to after-ripening |
| E | S-1 | 0.01 | Prior to after-ripening |
|  | S-2 | 0.45 | Prior to after-ripening |
|  | S-8 | 0.05 | Prior to after-ripening |
|  | S-13 | 0.01 | Subsequent to after-ripening |
| F | S-2 | 0.4 | Prior to after-ripening |
|  | S-3 | 0.04 | Prior to after-ripening |
|  | S-8 | 0.04 | Prior to after-ripening |
| G | S-4 | 0.3 | Subsequent to after-ripening |
|  | S-5 | 0.05 | Subsequent to after-ripening |
|  | S-12 | 0.1 | Subsequent to after-ripening |
| H | S-4 | 0.2 | Prior to after-ripening |
|  | S-5 | 0.05 | Subsequent to after-ripening |
|  | S-9 | 0.15 | Prior to after-ripening |
|  | S-14 | 0.02 | Subsequent to after-ripening |
| I | S-4 | 0.3 | Prior to after-ripening |
|  | S-9 | 0.2 | Prior to after-ripening |
|  | S-12 | 0.1 | Prior to after-ripening |
| J | S-4 | 0.35 | Prior to after-ripening |
|  | S-5 | 0.05 | Subsequent to after-ripening |
|  | S-12 | 0.1 | Prior to after-ripening |
| K | S-4 | 0.3 | Prior to after-ripening |
|  | S-9 | 0.05 | Prior to after-ripening |
|  | S-12 | 0.1 | Prior to after-ripening |
|  | S-14 | 0.02 | Prior to after-ripening |
| L, M | S-6 | 0.1 | Subsequent to after-ripening |
|  | S-10 | 0.2 | Subsequent to after-ripening |
|  | S-11 | 0.05 | Subsequent to after-ripening |
| N | S-6 | 0.05 | Subsequent to after-ripening |
|  | S-7 | 0.05 | Subsequent to after-ripening |
|  | S-10 | 0.25 | Subsequent to after-ripening |
|  | S-11 | 0.05 | Subsequent to after-ripening |
| O | S-10 | 0.4 | Subsequent to after-ripening |
|  | S-11 | 0.15 | Subsequent to after-ripening |
| P | S-6 | 0.05 | Subsequent to after-ripening |
|  | S-7 | 0.05 | Subsequent to after-ripening |
|  | S-10 | 0.3 | Prior to after-ripening |
|  | S-11 | 0.1 | Prior to after-ripening |
| Q | S-6 | 0.05 | Prior to after-ripening |
|  | S-7 | 0.05 | Prior to after-ripening |

TABLE 2-continued
Spectral sensitization of Emulsions A to E
| Emulsion | Spectral sensitizer added | Addition amount per mol of silver halide (g) | Timing of the addition of the spectral sensitizer |
|---|---|---|---|
| | S-10 | 0.2 | Prior to after-ripening |
| | S-11 | 0.25 | Prior to after-ripening |
| R | S-15 | 0.35 | Prior to after-ripening |
| | S-9 | 0.05 | Prior to after-ripening |
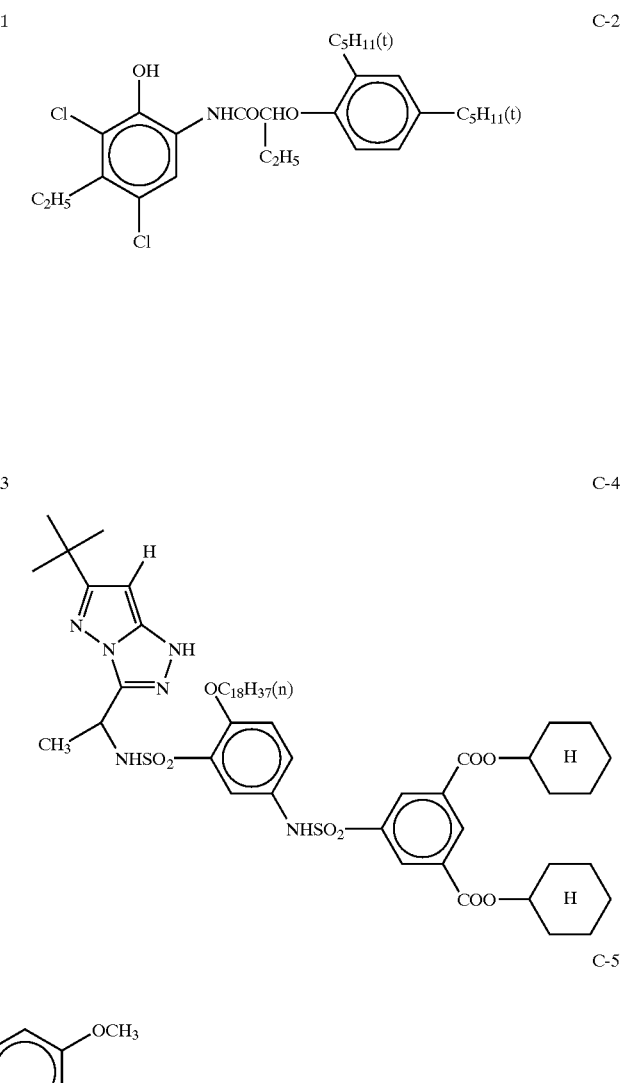
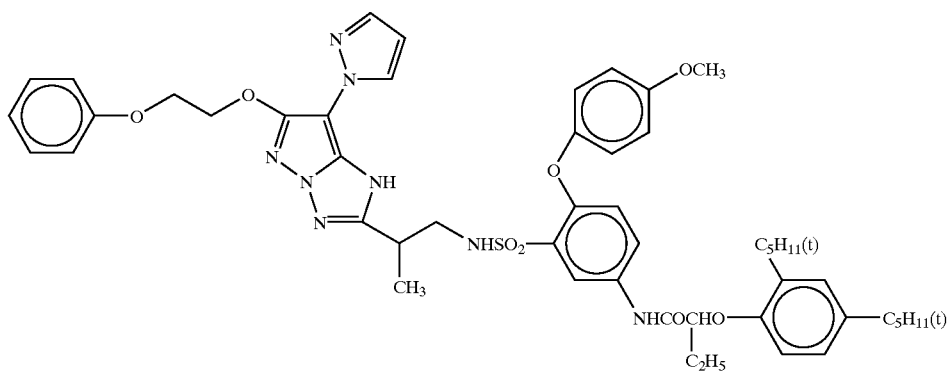

-continued

Oil-1 Tri-n-hexyl phosphate
Oil-2 Tricresyl phosphate

Oil-3

Oil-4 Tricyclohexyl phosphate
Oil-5 Bis(2-ethylhexyl)succinate

Cpd-A 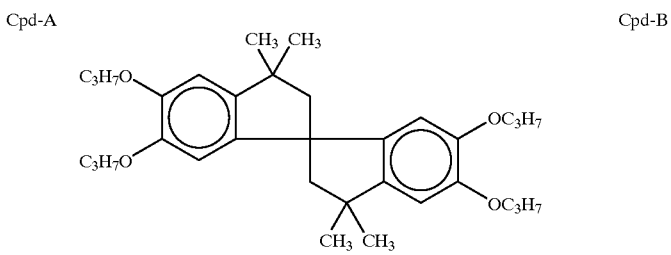
Cpd-B
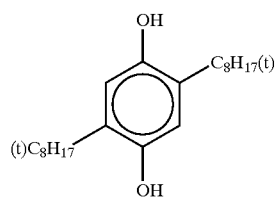
Cpd-C 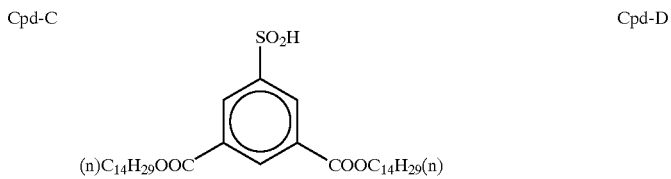
Cpd-D
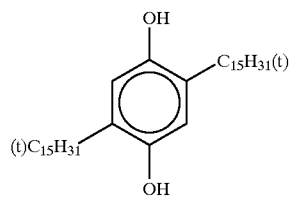
Cpd-E 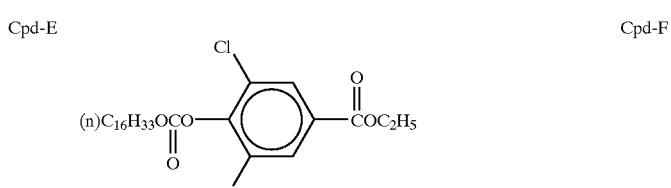
Cpd-F
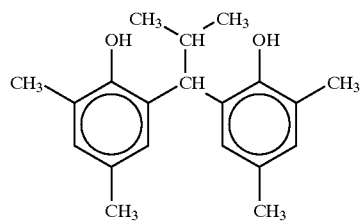
Cpd-G 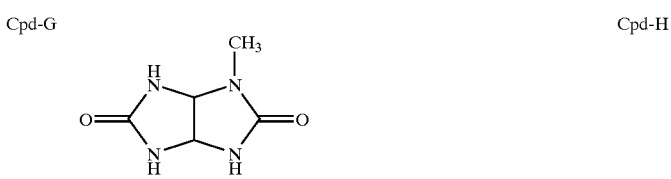
Cpd-H
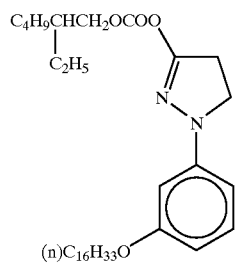
Cpd-I 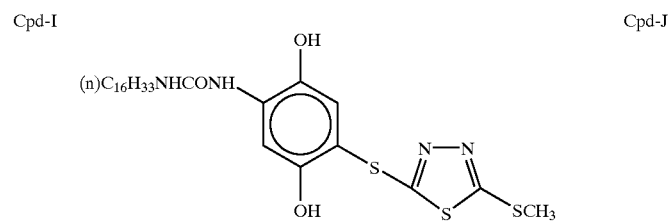
Cpd-J
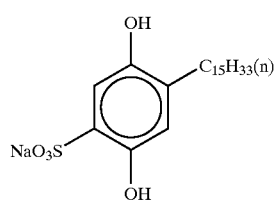
Cpd-K 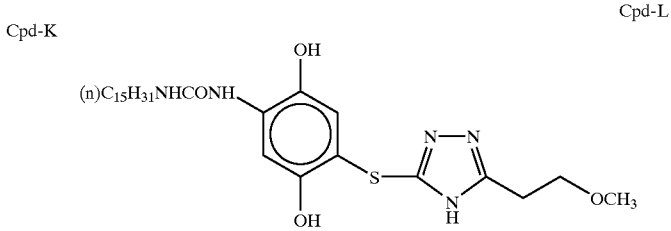
Cpd-L
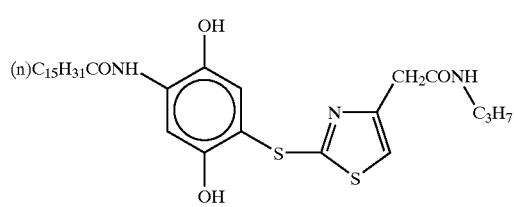
Cpd-M 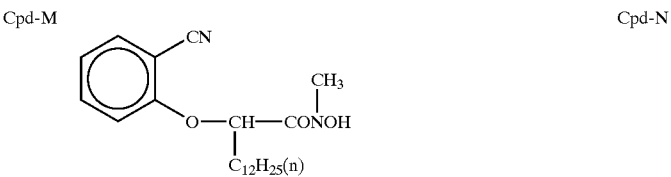
Cpd-N
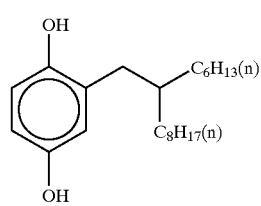

-continued
Cpd-O 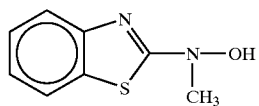
Cpd-P 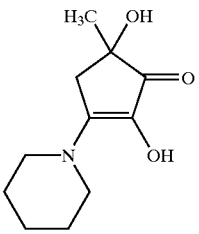
Cpd-Q 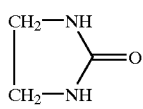
U-1 
U-2 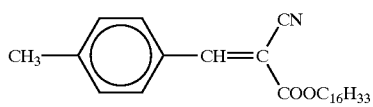
U-3 
U-4 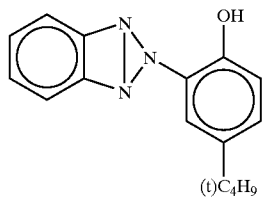
U-5 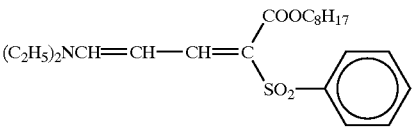
U-6 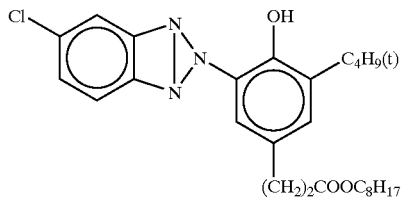
S-1 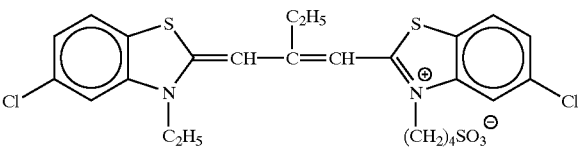
S-2 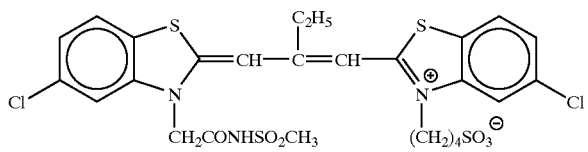
S-3 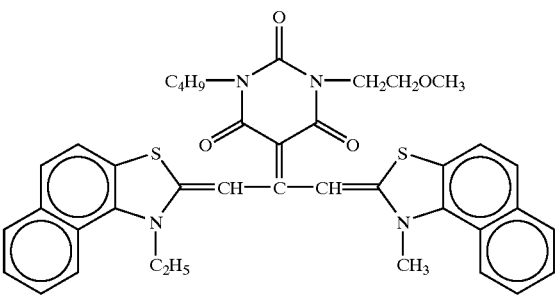
S-4 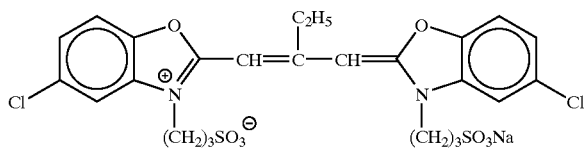
S-5 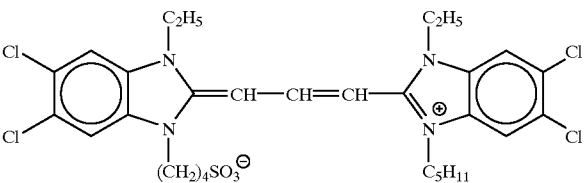

-continued
S-6
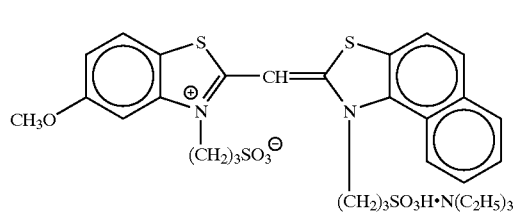
S-7
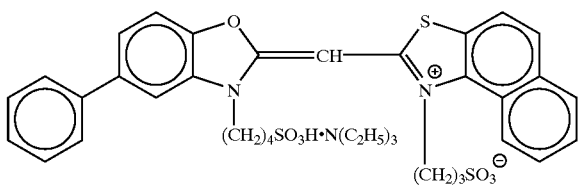
S-8
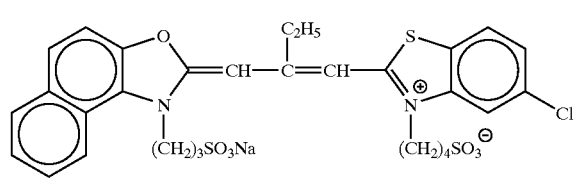
S-9
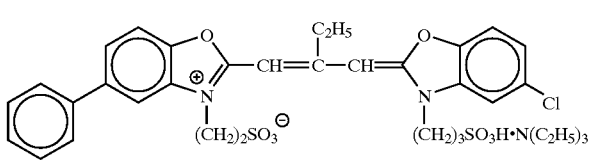
S-10
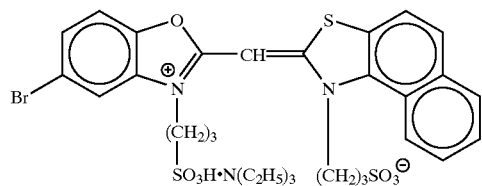
S-11
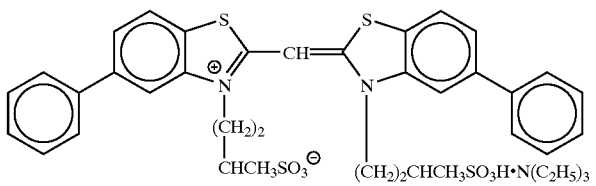
S-12
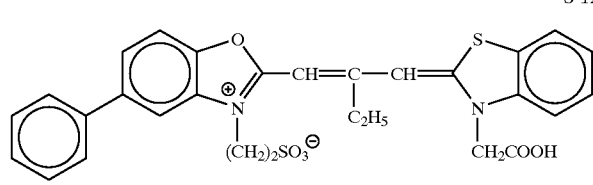
S-13
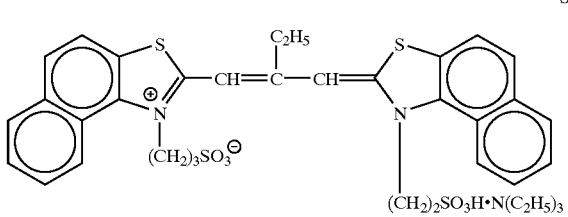
S-14
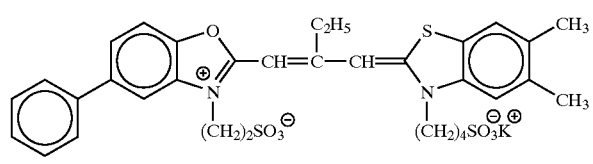
S-15
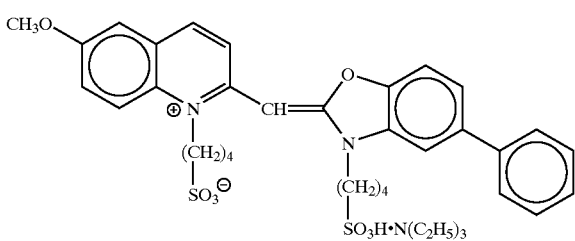
D-1
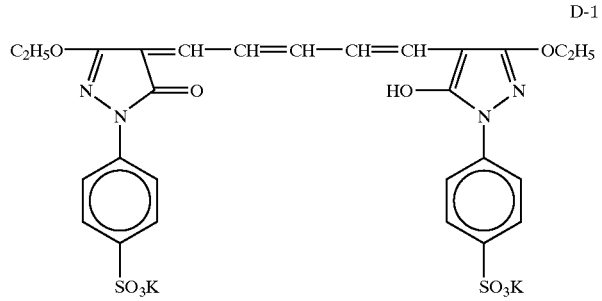
D-2
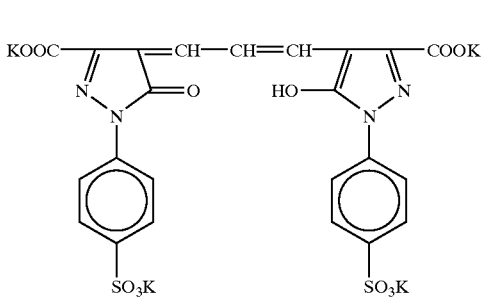

D-3
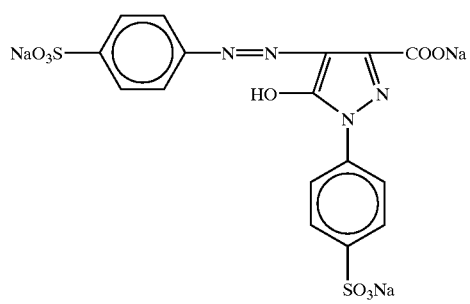
D-4
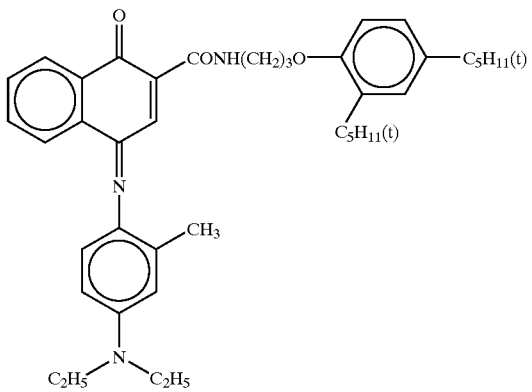
D-5
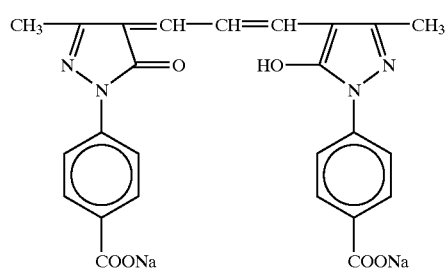
D-6
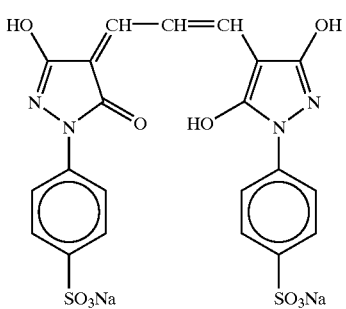
D-7
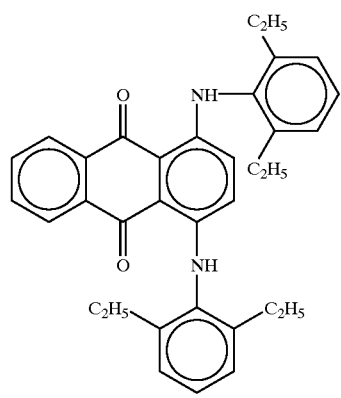
D-8
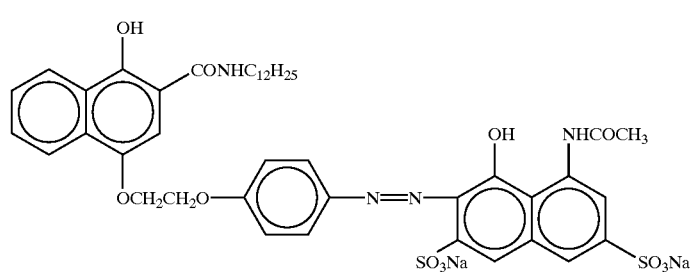

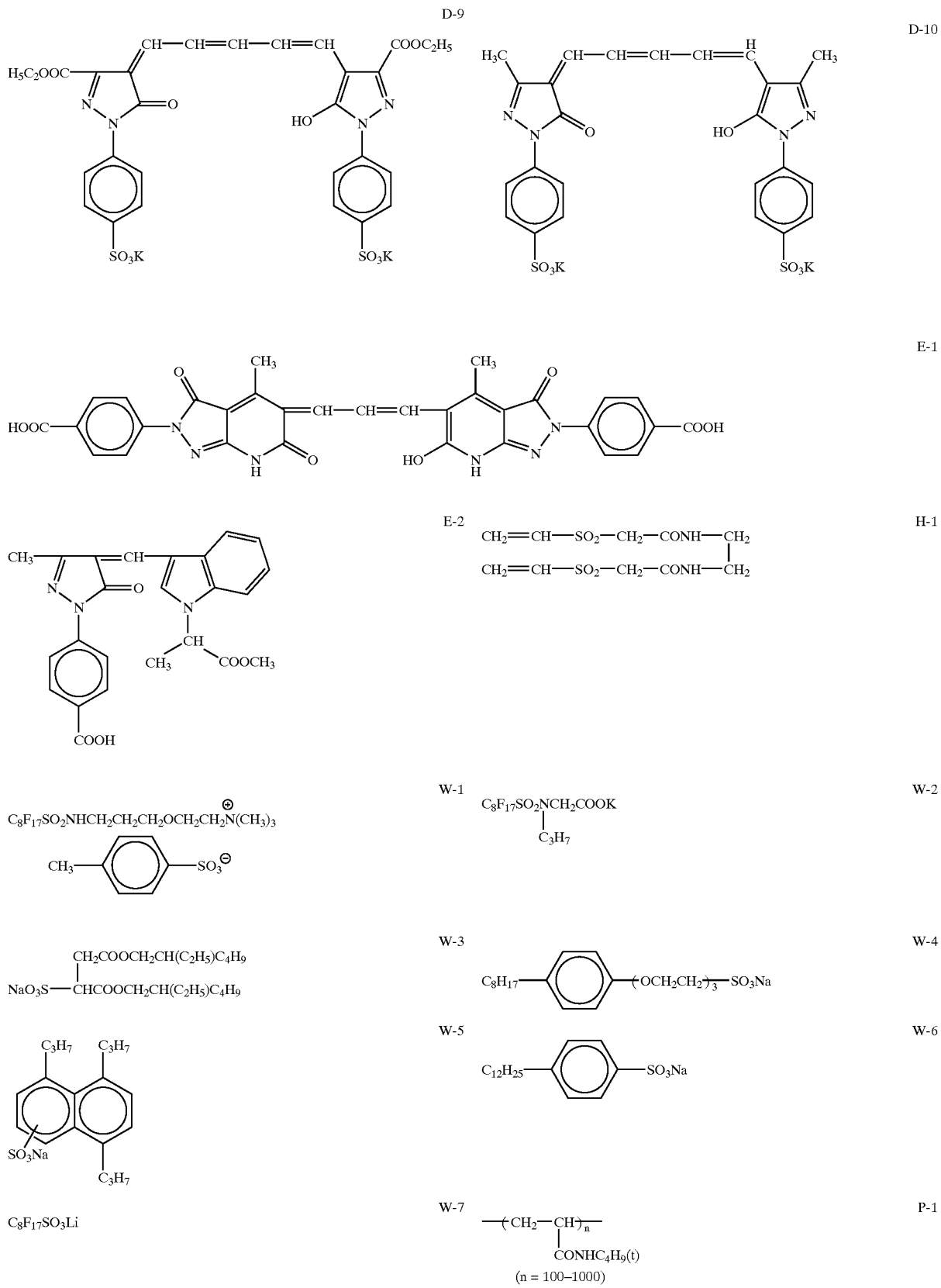

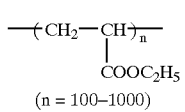
P-1
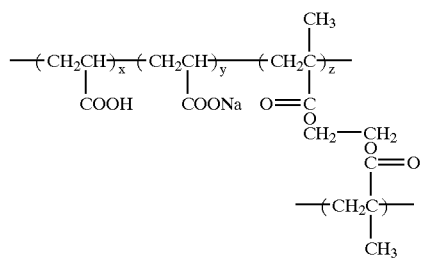
P-2
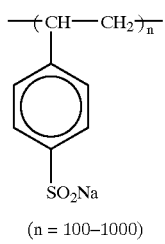
P-3
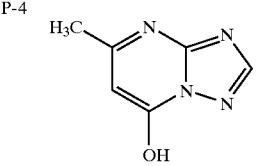
P-4
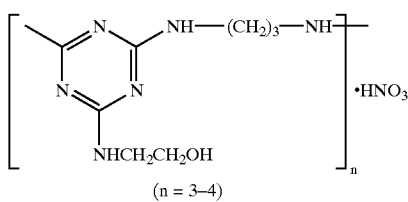
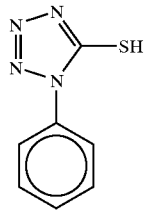
F-1
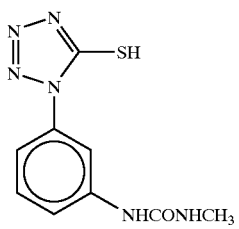
F-2
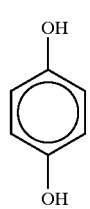
F-3
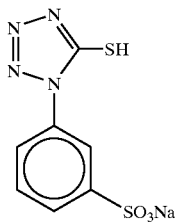
F-4
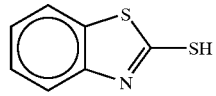
F-5
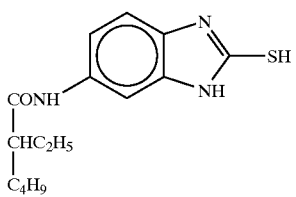
F-6
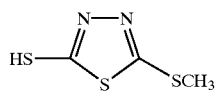
F-7

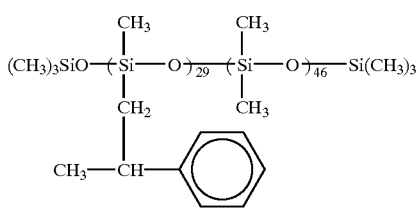

SO-1

Preparation of dispersions of organic solid dispersion dyes (Preparation of dispersion of dye E-1)

100 g of Pluronic F88 (an ethylene oxide-propylene oxide block copolymer) manufactured by BASF CORP. and water were added to a wet cake of the dye E-1 (the net weight of E-1 was 270 g), and the resultant material was stirred to make 4,000 g. Next, the Ultra Visco Mill (UVM-2) manufactured by Imex K.K. was filled with 1,700 mL of zirconia beads with an average grain size of 0.5 mm, and the slurry was milled through this UVM-2 at a peripheral speed of approximately 10 m/sec and a discharge rate of 0.5 L/min for 2 hr. The beads were filtered out, and water was added to dilute the material to a dye concentration of 3%. After that, the material was heated to 90° C. for 10 hr for stabilization. The average grain size of the obtained fine dye grains was 0.30 μm, and the grain size distribution (grain size standard deviation×100/average grain size) was 20%.

(Preparation of Solid Dispersion of Dye E-2).

Water and 270 g of W-4 were added to 1,400 g of a wet cake of E-2 containing 30 weight % of water, and the resultant material was stirred to form a slurry having an E-2 concentration of 40 weight %. Next, the Ultra Visco Mill (UVM-2) manufactured by Imex K.K. was filled with 1,700 mL of zirconia beads with an average grain size of 0.5 mm, and the slurry was milled through this UVM-2 at a peripheral speed of approximately 10 m/sec and a discharge rate of 0.5 L/min for 8 hr, thereby obtaining a solid fine-grain dispersion of E-2. The dispersion was diluted to 20 weight % by ion exchange water to obtain a solid fine grain dispersion. The average grain size of the prepared yellow coupler containing lipophilic fine grain dispersion was 0.10 to 0.20 μm.

Comparative Examples-2 to -7

Preparation of Samples 102 to 107

Sample 102 (using comparative coupler (Cp-2)), sample 103 (using comparative coupler (Cp-3)), sample 104 (using comparative coupler (Cp-4)), sample 105 (using comparative coupler (Cp-5), sample 106 (using comparative coupler (Cp-6), and sample 107 (using comparative coupler (Cp-7), were prepared in the same manner as in Comparative Example-1, except that the comparative coupler (Cp-1) in Comparative Example-1 was substituted by equimolar amounts of comparative coupler (Cp-2) (compound (A-2) in Synthesis Example 1 of the present specification), comparative coupler (Cp-3) (compound (B-3) in Synthesis Example 2 of the present specification), comparative coupler (Cp-4) (compound (C-3) in Synthesis Example 3 of the present specification), comparative coupler (Cp-5), comparative coupler (Cp-6) and comparative coupler (Cp-7), respectively. The average grain size of each of the prepared yellow coupler-containing lipophilic fine grain dispersions was within the range of 0.10 to 0.20 μm.

Comparative coupler (Cp-1)

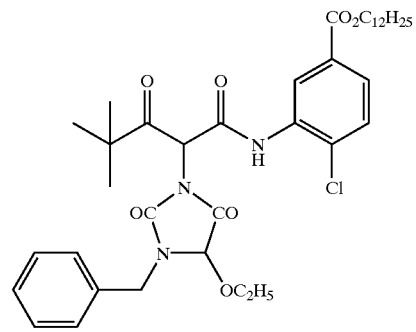

Comparative coupler (Cp-2)

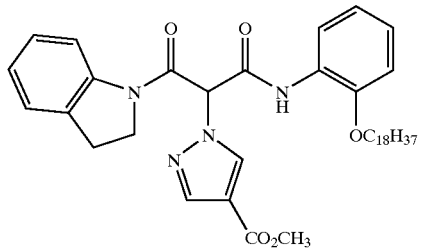

Comparative coupler (Cp-3)

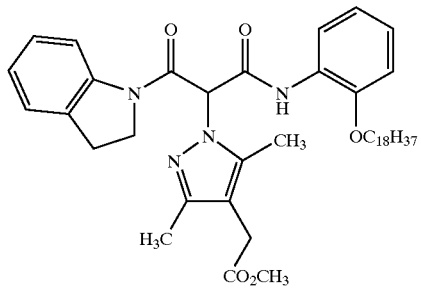

Comparative coupler (Cp-4)

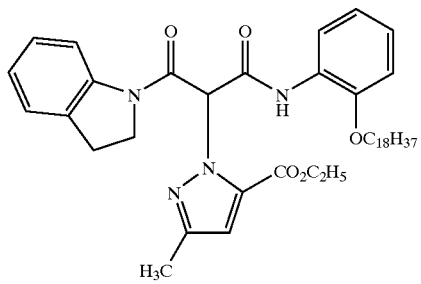

-continued

Comparative coupler (Cp-5)

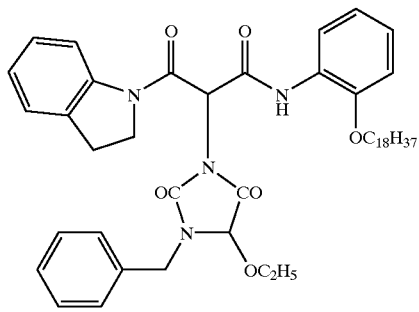

Comparative coupler (Cp-6)

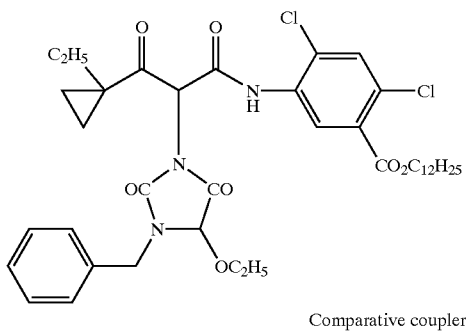

Comparative coupler (Cp-7)

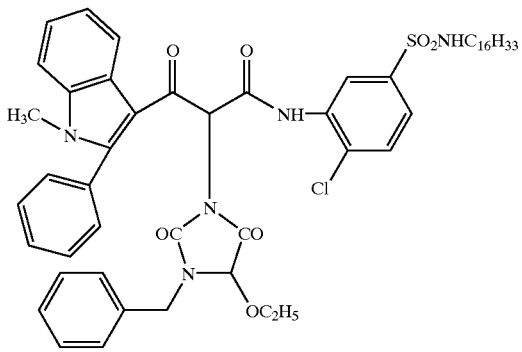

Examples 1-5

Preparation of Samples 108 to 112

Sample 108 (using Coupler (1)), sample 109 (using coupler (2)), sample 110 (using coupler (3)), sample 111 (using coupler (41)), and sample 112 (using coupler (59)) were prepared in the same manner as in Comparative Example-1, except that the comparative coupler (Cp-1) of Comparative Example-1 was substituted by equimolar amounts of Coupler (1), Coupler (2), Coupler (3), Coupler (41) and Coupler (59), respectively. The average grain size of each of the prepared yellow coupler-containing lipophilic fine grain dispersions was in the range of 0.10 to 0.20 μm.

<Color Generation Property Test>

Samples 101 to 112 obtained by the above Comparative Examples 1–7 and Examples 1–5 were subjected to exposure under conventional sensitometry conditions, and to the following development processing (development processing A).

At the time of processing, non-exposed samples and completely-exposed samples in the ratio of 1:1 for each of samples 101 to 107 were subjected to running processing until the replenishment amount reaches 4 times the tank volume, and thereafter subjected to processing for evaluation.

| Processing Step | Time | Temperature | Tank volume | Replenishment rate |
|---|---|---|---|---|
| 1st development | 6 min | 38° C. | 37 L | 2,200 mL/m² |
| 1st washing | 2 min | 38° C. | 16 L | 4,000 mL/m² |
| Reversal | 2 min | 38° C. | 17 L | 1,100 mL/m² |
| Color development | 6 min | 38° C. | 30 L | 2,200 mL/m² |
| Pre-bleaching | 2 min | 38° C. | 19 L | 1,100 mL/m² |
| Bleaching | 6 min | 38° C. | 30 L | 220 mL/m² |
| Fixing | 4 min | 38° C. | 29 L | 1,100 mL/m² |
| 2nd washing | 4 min | 38° C. | 35 L | 4,000 mL/m² |
| Final rinsing | 1 min | 25° C. | 19 L | 1,100 mL/m² |

The initial composition of each processing solution is that as set forth below.

| <1st developer> | <Tank solution> | <Replenisher> |
|---|---|---|
| Nitrilo-N,N,N-trimethylene phosphonic acid · pentasodium salt | 1.5 g | 1.5 g |
| Diethylenetriamine pentaacetic acid · pentasodium salt | 2.0 g | 2.0 g |
| Sodium sulfite | 30 g | 30 g |
| Hydroquinone · potassium monosulfonate | 20 g | 20 g |
| Potassium carbonate | 15 g | 20 g |
| Potassium bicarbonate | 12 g | 15 g |
| 1-phenyl-4-methyl-4-hydroxymethyl-3-pyrazolidone | 2.5 g | 3.0 g |
| Potassium bromide | 2.5 g | 1.4 g |
| Potassium thiocyanate | 1.2 g | 1.2 g |
| Potassium iodide | 2.0 mg | — |
| Diethyleneglycol | 13 g | 15 g |
| Water to make | 1,000 mL | 1,000 mL |
| pH | 9.60 | 9.60 |

The pH was adjusted by sulfuric acid or potassium hydroxide.

| <Reversal solution> | <Tank solution> | <Replenisher> |
|---|---|---|
| Nitrilo-N,N,N-trimethylene phosphonic acid · pentasodium salt | 3.0 g | the same as tank solution |
| Stannous chloride · dihydrate | 1.0 g | |
| p-aminophenol | 0.1 g | |
| Sodium hydroxide | 8 g | |
| Glacial acetic acid | 15 mL | |
| Water to make | 1,000 mL | |
| pH | 6.00 | |

The pH was adjusted by acetic acid or sodium hydroxide.

| <Color developer> | <Tank solution> | <Replenisher> |
|---|---|---|
| Nitrilo-N,N,N-trimethylene phosphonic acid · pentasodium salt | 2.0 g | 2.0 g |
| Sodium sulfite | 7.0 g | 7.0 g |
| Trisodium phosphate · | 36 g | 36 g |

-continued

| <Color developer> | <Tank solution> | <Replenisher> |
|---|---|---|
| dodecahydrate | | |
| Potassium bromide | 1.0 g | — |
| Potassium iodide | 90 mg | — |
| Sodium hydroxide | 12.0 g | 12.0 g |
| Citrazinic acid | 0.5 g | 0.5 g |
| N-ethyl-N-(β-methanesulfon amidoethyl)-3-methyl-4-aminoaniline · 3/2 sulfuric acid · monohydrate | 10 g | 10 g |
| 3,6-dithiaoctane-1,8-diol | 1.0 g | 1.0 g |
| Water to make | 1,000 mL | 1,000 mL |
| pH | 11.80 | 12.00 |

The pH was adjusted by sulfuric acid or potassium hydroxide.

| <Pre-bleaching solution> | <Tank solution> | <Replenisher> |
|---|---|---|
| Ethylenediaminetetraacetic acid · disodium salt · dihydrate | 8.0 g | 8.0 g |
| Sodium sulfite | 6.0 g | 8.0 g |
| 1-thioglycerol | 0.4 g | 0.4 g |
| Formaldehyde sodium bisulfite adduct | 30 g | 35 g |
| Water to make | 1,000 mL | 1,000 mL |
| pH | 6.3 | 6.10 |

The pH was adjusted by acetic acid or sodium hydroxide.

| <Bleaching solution> | <Tank solution> | <Replenisher> |
|---|---|---|
| Ethylenediaminetetraacetic acid.disodium salt.dihydrate dihydrate | 2.0 g | 4.0 g |
| Ethylenediaminetetraacetic acid.Fe (III).ammonium. dihydrate | 120 g | 240 g |
| Potassium bromide | 100 g | 200 g |
| Ammonium nitrate | 10 g | 20 g |
| Water to make | 1,000 mL | 1,000 mL |
| pH | 5.70 | 5.50 |

The pH was adjusted by nitric acid or sodium hydroxide.

| <Fixing solution> | <Tank solution> | <Replenisher> |
|---|---|---|
| Ammonium thiosulfate | 80 g | the same as tank solution |
| Sodium sulfite | 5.0 g | |
| Sodium bisulfite | 5.0 g | |
| Water to make | 1,000 mL | |
| pH | 6.60 | |

The pH was adjusted by acetic acid or ammonia water.

| <Stabilizer> | <Tank solution> | <Replenisher> |
|---|---|---|
| 1,2-benzoisothiazoline-3-one | 0.02 g | 0.03 g |
| Polyoxyethylene-p-monononyl phenylether | 0.3 g | 0.3 g |

-continued

| <Stabilizer> | <Tank solution> | <Replenisher> |
|---|---|---|
| (average polymerization degree = 10) Polymaleic acid (average molecular weight = 2,000) | 0.1 g | 0.15 g |
| Water to make | 1,000 mL | 1,000 mL |
| pH | 7.0 | 7.0 |

Note that in the development processing step, the solution of each bath was continuously circulated and stirred, and at the bottom of each tank was provided with a bubbling pipe having small apertures of 0.3 mm diameter in intervals of 1 cm, and nitrogen gas was continuously bubbled through the apertures to stir the solution.

Each of the processed samples generated yellow color. As shown in Table 3, $D_{max}$ values of samples 105 to 107 of the lightsensitive material of the present invention were higher than those of samples 101 to 104 of comparative lightsensitive materials. Further, the hue of each of samples 108 to 112 was sharper than those of Samples 101 to 107.

TABLE 3

| Sample No. | Coupler | $D_{max.}$ | Remarks |
|---|---|---|---|
| 101 | Comparative coupler (Cp-1) | 1.8 | Comp. |
| 102 | Comparative coupler (Cp-2) | 1.7 | Comp. |
| 103 | Comparative coupler (Cp-3) | 1.77 | Comp. |
| 104 | Comparative coupler (Cp-4) | 1.65 | Comp. |
| 105 | Comparative coupler (Cp-5) | 1.60 | Comp. |
| 106 | Comparative coupler (Cp-6) | 2.30 | Comp. |
| 107 | Comparative coupler (Cp-7) | 2.35 | Comp. |
| 108 | Coupler (1) | 2.84 | Inv. |
| 109 | Coupler (2) | 2.81 | Inv. |
| 110 | Coupler (3) | 2.83 | Inv. |
| 111 | Coupler (41) | 2.72 | Inv. |
| 112 | Coupler (59) | 2.88 | Inv. |

Example-6

A lightsensitive material was prepared in the same manner as sample 101 of JP-A-11-305396, except that each of ExY-2 and ExY-3 in the 13th and 14th layers of sample 101 of JP-A-11-305396 was substituted by equimolar amounts of the-dye-forming coupler (1) of the present invention. The lightsensitive material was subjected to exposure and development by the method described in Example 1 of JP-A-11-305396, and evaluated by the methods described in the Examples of the present specification, and results similar to those in Example 1 of the present specification were obtained.

Example-7

A lightsensitive material was prepared in the same manner as sample 107 of JP-A-11-84601, except that each of couplers C-5 and C-6 in the 13th and 14th layers and C-6 and C-10 in the 15th layers of sample 107 of JP-A-11-894601 was changed to equimolar amounts of the dye-forming coupler (1) of the present invention. The lightsensitive material was subjected to exposure and development by the method described in Example 1 of JP-A-11-84601, and evaluated by the methods described in the Examples of the present specification, and results similar to those in Example 1 of the present specification were obtained.

According to the present invention, a dye-forming coupler with high color generation property, which provides dye having excellent hue, large molar extinction coefficient, and good storage stability, can be manufactured by a shorter process and low cost. By adding the coupler into a light-sensitive material, it is possible to provide a silver halide photographic lightsensitive material that is excellent in color reproduction and sharpness, and has good image fastness.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A silver halide color photographic light sensitive material comprising at least one silver halide emulsion layer on a support, wherein the silver halide emulsion layer contains at least one yellow coupler selected from the group consisting of yellow couplers represented by the following formula (I), (II), (III) or (IV):

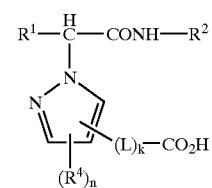

(I)

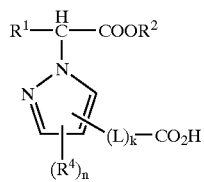

(II)

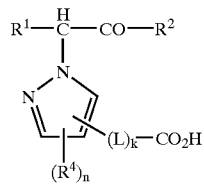

(III)

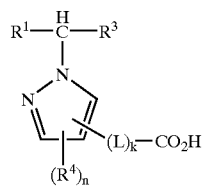

(IV)

wherein $R^1$ represents an acyl group, aryl group, heterocyclic residue, alkoxycarbonyl group, aryloxycarbonyl group, carbamoyl group, sulfamoyl group, alkylsulfonyl group, or arylsulfonyl group, each of which may have a substituent, or a cyano group or nitro group; $R^2$ represents an alkyl group, aryl group or heterocyclic residue, each of which may have a substituent; $R^3$ represents an aryl group or heterocyclic residue, each of which may have a substituent; $R^4$ represents a substituent; n represents an integer of 0 to 2, wherein when n is 2, a plurality of $R^4$'s may be the same or different from each other; L represents a divalent linking group; and k represents an integer of 0 or more, wherein when k is 2 or more, a plurality of L's may be the same linking groups or may be different from each other.

2. The silver halide color photographic lightsensitive material according to claim 1, wherein the coupler represented by the formula (III) is represented by the following formula (V):

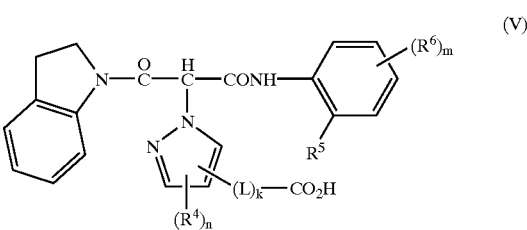

(V)

wherein $R^4$ represents a substituent; n represents an integer of 0 to 2, wherein when n is 2, a plurality of $R^4$'s may be the same or different from each other; $R^5$ represents a hydrogen atom or substituent; $R^6$ represents a substituent; m represents an integer of 0 to 4, wherein when m is 2 or more, a plurality of $R^6$'s may be the same or different from each other, and two of them may be bonded together to form a ring; L represents a divalent linking group; and k represents an integer of 0 or more, wherein when k is 2 or more, a plurality of L's may be the same or different from each other.

3. The silver halide color photographic lightsensitive material according to claim 1, wherein the coupler represented by the formula (I) is represented by the following formula (VI):

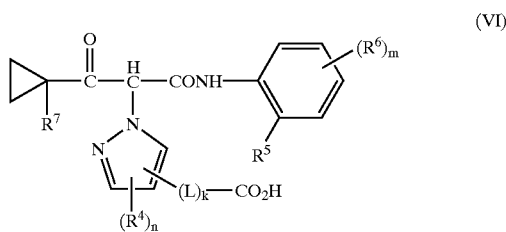

(VI)

wherein $R^4$ represents a substituent; n represents an integer of 0 to 2, wherein when n is 2 or more, a plurality of $R^4$'s may be the same or different from each other; $R^6$ represents a substituent; $R^5$ and $R^7$ independently represents a hydrogen atom or substituent; m represents an integer of 0 to 4, wherein when m is 2 or more, a plurality of $R^6$'s may be the same or different from each other, and two of them may be bonded together to form a ring; L represents a divalent linking group; k represents an integer of 0 or more, wherein when k is 2 or more, a plurality of L's may be the same or different from each other.

4. The silver halide color photographic lightsensitive material according to claim 1, wherein the coupler represented by the formula (III) is represented by the following formula (VII):

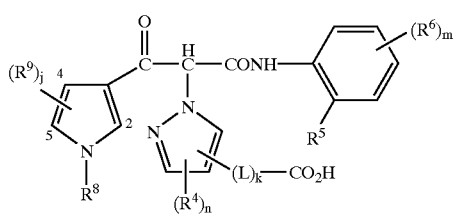

(VII)

wherein $R^4$ represents a substituent; n represents an integer of 0 to 2, wherein when n is 2 or more, a plurality of $R^4$'s may be the same or different from each other; $R^6$ and $R^9$ independently represents a substituent; $R^5$ and $R^8$ independently represents a hydrogen atom or substituent; m represents an integer of 0 to 4, wherein when m is 2 or more, a plurality of $R^6$'s may be the same or different from each other, and two of them may be bonded together to form a ring; L represents a divalent linking group; k represents an integer of 0 or more, wherein when k is 2 or more, a plurality of L's may be the same or different from each other; j represents an integer of 3 or less, wherein when j is 2 or more, a plurality of $R^9$'s may be the same or different from each other, and two of them may be bonded together to form a ring.

* * * * *